US008852916B2

(12) United States Patent
Hyde et al.

(10) Patent No.: US 8,852,916 B2
(45) Date of Patent: Oct. 7, 2014

(54) COMPOSITIONS AND METHODS FOR THERAPEUTIC DELIVERY WITH MICROORGANISMS

(75) Inventors: Roderick A. Hyde, Redmond, WA (US);
Edward K. Y. Jung, Bellevue, WA (US);
Royce A. Levien, Lexington, MA (US);
Robert W. Lord, Seattle, WA (US);
Mark A. Malamud, Seattle, WA (US);
John D. Rinaldo, Jr., Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 377 days.

(21) Appl. No.: 12/657,607

(22) Filed: Jan. 22, 2010

(65) Prior Publication Data
US 2011/0183347 A1   Jul. 28, 2011

(51) Int. Cl.
*C12N 1/20*  (2006.01)
*C12N 1/00*  (2006.01)
*A61K 38/20*  (2006.01)
*A61K 38/18*  (2006.01)
*C12N 1/36*  (2006.01)
*A61K 38/16*  (2006.01)
*A61K 35/74*  (2006.01)
*A61K 36/064*  (2006.01)
*C12N 15/63*  (2006.01)

(52) U.S. Cl.
CPC .......... *C12N 15/635* (2013.01); *A61K 38/2066* (2013.01); *A61K 38/1841* (2013.01); *C12N 1/36* (2013.01); *A61K 38/208* (2013.01); *A61K 38/2013* (2013.01); *A61K 38/162* (2013.01); *A61K 35/74* (2013.01); *A61K 35/747* (2013.01); *A61K 36/064* (2013.01)
USPC ........................................ 435/252.3; 435/243

(58) Field of Classification Search
None
See application file for complete search history.

(56) References Cited

U.S. PATENT DOCUMENTS

| 4,837,151 A | 6/1989 | Stocker |
| 5,017,373 A | 5/1991 | Herrnstadt et al. |
| 5,316,940 A | 5/1994 | Georgiou et al. |
| 5,643,771 A | 7/1997 | Stocker |
| 5,663,063 A | 9/1997 | Peoples et al. |
| 5,710,027 A | 1/1998 | Hauptmann et al. |
| 5,804,563 A | 9/1998 | Still et al. |
| 5,823,993 A | 10/1998 | Lemelson |
| 5,831,012 A | 11/1998 | Nilsson et al. |
| 5,888,396 A | 3/1999 | Perriello |
| 5,928,635 A | 7/1999 | Schmidt |
| 6,066,343 A | 5/2000 | Megeed et al. |
| 6,100,388 A | 8/2000 | Casas et al. |
| 6,242,194 B1 | 6/2001 | Kullen et al. |
| 6,254,832 B1 | 7/2001 | Rainin et al. |
| 6,416,754 B1 | 7/2002 | Brown et al. |
| 6,605,286 B2 | 8/2003 | Steidler et al. |
| 6,610,529 B1 | 8/2003 | Curtiss, III et al. |
| 6,652,849 B2 | 11/2003 | Brown et al. |
| 6,670,427 B1 | 12/2003 | Ulbricht et al. |
| 6,797,522 B1 | 9/2004 | Still et al. |
| 6,852,511 B2 | 2/2005 | Romano et al. |
| 6,875,356 B2 | 4/2005 | Perriello |
| 7,001,359 B2 | 2/2006 | Rogers |
| 7,220,418 B1 | 5/2007 | Hans et al. |
| 7,341,860 B2 | 3/2008 | Curtiss, III et al. |
| 7,344,710 B2 | 3/2008 | Dang et al. |
| 7,447,595 B1 | 11/2008 | Pohlschroder et al. |
| 7,462,708 B2 | 12/2008 | Singh et al. |
| 7,510,852 B2 | 3/2009 | Royer et al. |
| 7,550,558 B2 | 6/2009 | Leite et al. |
| 7,780,961 B2 | 8/2010 | Steidler |
| 2002/0137190 A1* | 9/2002 | Koffas et al. ............... 435/252.3 |
| 2003/0004403 A1 | 1/2003 | Drinan et al. |
| 2003/0064074 A1 | 4/2003 | Chang et al. |
| 2004/0018508 A1 | 1/2004 | Friedman |
| 2004/0043003 A1* | 3/2004 | Chen et al. ................... 424/93.2 |
| 2004/0241849 A1 | 12/2004 | Kapat |
| 2005/0031643 A1 | 2/2005 | Szalay et al. |
| 2005/0101005 A1* | 5/2005 | Steidler ........................ 435/252.3 |
| 2005/0112133 A1 | 5/2005 | Druilhe |
| 2005/0124010 A1* | 6/2005 | Short et al. .................... 435/7.23 |
| 2005/0137626 A1 | 6/2005 | Pastore et al. |
| 2005/0276788 A1 | 12/2005 | Steidler et al. |
| 2006/0121054 A1 | 6/2006 | Sun et al. |
| 2007/0110723 A1 | 5/2007 | Hans et al. |
| 2007/0122427 A1 | 5/2007 | Hans et al. |
| 2007/0213659 A1 | 9/2007 | Trovato et al. |
| 2008/0044900 A1 | 2/2008 | Mooney et al. |
| 2008/0253990 A1 | 10/2008 | Steidler et al. |
| 2008/0254014 A1 | 10/2008 | Rottiers et al. |
| 2009/0115603 A1* | 5/2009 | Tabe ............................ 340/540 |

(Continued)

FOREIGN PATENT DOCUMENTS

WO   WO 96/40947    * 12/1996   ............. C12N 15/64
WO   WO 01/24690 A2   4/2001
WO   WO 2005/041848 A2   5/2005

OTHER PUBLICATIONS

Qiu et al. Environment-sensitive hydrogels for drug delivery. 2001. Advanced Drug Delivery Reviews. vol. 53, pp. 321-329.*
Narvaez-Vasquez et al. Chapter 15 Systemins and AtPeps: Defense Related Peptide Signals. 2008. Induced Plant Resistance to Herbivory. pp. 313-328.*
Syto et al. Structural and biological stability of human interleukin 10 homodimer. Dec. 1998. Biochemistry. vol. 37, No. 48, pp. 16943-16951.*
Ui et al. The production of D-acetoin by a transgenic *Escherichia coli*. Letters in Applied Microbiology. 1998, vol. 26, pp. 275-278.*
Nichol et al.; "Effectiveness of Live, Attenuated Intranasal Influenza Virus Vaccine in Healthy, Working Adults"; JAMA; Jul. 14, 1999; pp. 137-144; vol. 281, No. 2; American Medical Association.

(Continued)

*Primary Examiner* — Anne Gussow
*Assistant Examiner* — Channing S Mahatan

(57) ABSTRACT

Certain embodiments disclosed relate to compositions, including therapeutic compositions, methods, devices, and systems that include modified microorganisms including at least one genetic element encoding at least one therapeutic agent or environmental treatment agent.

34 Claims, 44 Drawing Sheets

(56) References Cited

U.S. PATENT DOCUMENTS

2009/0162911 A1 6/2009 Larossa et al.
2010/0152880 A1 6/2010 Boyden et al.
2010/0292495 A1 11/2010 Schüler et al.
2011/0002892 A1* 1/2011 Galloway et al. ............ 424/93.7

OTHER PUBLICATIONS

The American Heritage® Dictionary of the English Language; "auxotrophic"; located at: http://www.credoreference.com/entry/hmdictenglang/auxotrophic ; bearing a date of 2007; © 2007, 2000 Houghton Mifflin Company.
The Columbia Encyclopedia; "Soil"; located at: http://www.credoreference.com/topic/soil; Aug. 24, 2012; 3 pages; Columbia University Press 2008.
The Columbia Encyclopedia; "Virus"; located at: http://www.credoreference.com/entry/columency/virus ; bearing a date of 2008; 1 page.
"Diatom"; The Columbia Encyclopedia; bearing a date of 2008; 2 pages; located at http://www.credoreference.com/topic/diatom.
"Eukaryotes"; Illustrated Dictionary of Science; bearing a date of 1988; 2 pages; located at: http://www.credoreference.com/topic/eukaryotic_cells.
"Prokaryotes"; Illustrated Dictionary of Science; bearing a date of 1988; 2 pages; located at: http://www.credoreference.com/topic/prokaryotes.
Hamilton, Kris; "Pseudomonas putida"; Microbe of the Week; Accessed Mar. 11, 2013 from http://web.mst.edu/~microbio/bio221_2007/P_putida.htm; pp. 1-3 ; Missouri Univeristy of Science and Technology.
Hazan et al.; "*Escherichia coli* mazEF-Mediated Cell Death Is Triggered by Various Stressful Conditions"; Journal of Bacteriology; bearing a date of Jun. 2004, accepted Feb. 23, 2004; pp. 3663-3669; vol. 186, No. 11; American Society for Microbiology.
Djeha et al.; "Combined Adenovirus-Mediated Nitroreductase Gene Delivery and CB1954 Treatment: A Well-Tolerated Therapy for Established Solid Tumors"; Molecular Therapy; bearing a date of Feb. 2001, accepted in revised form Dec. 21, 2000; pp. 233-240; vol. 3, No. 2; The American Society of Gene Therapy.
Chou et al.; "Characterization of a pH-Inducible Promoter System for High-Level Expression of Recombinant Proteins in *Escherichia coli*"; Biotechnology and Bioengineering; Jul. 20, 1995; pp. 186-192; vol. 47, No. 2; John Wiley & Sons, Inc.
Abosereh et al.; "Mutation Induction for Genetic Improvement of *Saccharomyces boulardii* Which Used as Probiotic Yeast"; Research Journal of Agriculture and Biological Sciences; 2006; pp. 478-482; vol. 2, No. 6; INSInet Publication.
Amitai et al.; "MazF-Mediated Cell Death in *Escherichia coli*: a Point of No Return"; Journal of Bacteriology; Dec. 2004; pp. 8295-8300; vol. 186, No. 24; American Society for Microbiology.
Andersson et al.; "Comparative Analysis of Human Gut Microbiota by Barcoded Pyrosequencing"; PLoS ONE; Jul. 2008; pp. 1-8; vol. 3, No. 7.
Applied BioSystems, ABI PRISM®, 3100 Genetic Analyzer; pp. 1-4; located at www.appliedbiosystems.com 2005.
Bääth, E.; "Measurement of protein synthesis by soil bacterial assemblages with the leucine incorporation technique"; Biol Fertil Soils; 1994; pp. 147-153; vol. 17; Abstract; 1 pg.; Springer-Verlag 1994.
Balagadde et al.; "A synthetic *Escherichia coli* predator-prey ecosystem"; Molecular Systems Biology; 2008; pp. 1-8; vol. 4, No. 187; EMBO and Nature Publishing Group.
Balan et al.; "A conditional suicide system for *Saccharomyces cerevisiae* relying on the intracellular production of the *Serratia marcescens* nuclease"; Yeast; 2005; pp. 203-212; vol. 22; John Wiley & Sons, Ltd.
Bermudez-Humaran et al.; "Current prophylactic and therapeutic uses of a recombinant *Lactococcus lactis* strain secreting biologically active interleukin-12"; J Mol Microbiol Biotechnol; 2008; pp. 80-89; vol. 14; Nos. 1-3; Abstract; 1 pg.

Biswas et al.; "High-Efficiency Gene Inactivation and Replacement System for Gram-Positive Bacteria"; Journal of Bacteriology; Jun. 1993; pp. 3628-3635; vol. 175, No. 11; American Society for Microbiology.
Blanquet et al.; "Recombinant *Saccharomyces cerevisiae* Expressing P450 in Artificial Digestive Systems: A Model for Biodetoxication in the Human Digestive Environment"; Applied and Environmental Microbiology; May 2003; pp. 2884-2892; vol. 69, No. 5; American Society for Microbiology.
Blevins et al.; "Metabolism of Propane, n-Propylamine, and Propionate by Hydrocarbon-Utilizing Bacteria"; Journal of Bacteriology; Oct. 1972; pp. 513-518; vol. 112, No. 1; American Society for Microbiology.
Boron et al., "Medical Physiology: A Cellular and Molecular Approach"; 2004; synopsis; 2 pgs.; Elsevier/Saunders.
Braat et al.; "A Phase I Trial With Transgenic Bacteria Expressing Interleukin-10 in Crohn's Disease"; Clinical Gastroenterology and Hepatology; 2006; pp. 754-759; vol. 4; American Gastroenterological Association Institute.
Brenner et al.; "Engineering microbial consortia: a new frontier in synthetic biology"; Trends in Biotechnology; pp. 483-489; vol. 26, No. 9; Elsevier Ltd., Jul. 31, 2008.
Brenner et al.; "Engineered bidirectional communication mediates a consensus in a microbial biofilm consortium"; PNAS; Oct. 30, 2007; pp. 17300-17304; vol. 104, No. 44; The National Academy of Sciences of the USA.
Buesing et al.; "Incorporation of Radiolabeled Leucine into Protein to Estimate Bacterial Production in Plant Litter, Sediment, Epiphytic Biofilms, and Water Samples"; Microbial Ecology; 2003; pp. 291-301; vol. 45; Springer-Verlag New York Inc.
Casson et al.; "The POLARIS Gene of *Arabidopsis* Encodes a Predicted Peptide Required for Correct Root Growth and Leaf Vascular Patterning"; The Plant Cell; Aug. 2002; pp. 1705-1721; vol. 14; American Society of Plant Biologists.
Contreras et al.; "Conditional-Suicide Containment System for Bacteria Which Mineralize Aromatics"; Applied and Environmental Microbiology; May 1991; pp. 1504-1508; vol. 57, No. 5; American Society for Microbiology.
Cotter et al.; "Surviving the Acid Test: Responses of Gram-Positive Bacteria to Low pH"; Microbiology and Molecular Biology Reviews; Sep. 2003; pp. 429-453; vol. 67, No. 3; American Society for Microbiology.
Crawford et al.; "Effects of a Lignin Peroxidase-Expressing Recombinant, *Streptomyces lividans* TK23.1 on Biogeochemical Cycling and the Numbers and Activities of Microorganisms in Soil"; Applied and Environmental Microbiology; Feb. 1993; pp. 508-518; vol. 59, No. 2; American Society for Microbiology.
Dethlefsen et al.; "The Pervasive Effects of an Antibiotic on the Human Gut Microbiota, as Revealed by Deep 16S rRNA Sequencing"; PLoS Biology; Nov. 2008; pp. 2383-2400; vol. 6, No. 11.
Dueber et al.; "Synthetic protein scaffolds provide modular control over metabolic flux"; Nature Biotechnology; Aug. 2009; pp. 753-759; vol. 27, No. 8; Nature America, Inc.
Engelberg-Kulka et al.; "Bacterial Programmed Cell Death and Multicellular Behavior in Bacteria"; PLoS Genetics; Oct. 2006; pp. 1518-1526; vol. 2, No. 10.
Eschenfeldt et al.; "Transformation of Fatty Acids Catalyzed by Cytochrome P450 Monooxygenase Enzymes of *Candida tropicalis*"; Applied and Environmental Microbiology; Oct. 2003; pp. 5992-5999; vol. 69, No. 10; American Society for Microbiology.
Felfoul et al.; "Magnetic Resonance Imaging of Fe3O4 Nanoparticles Embedded in Living Magnetotactic Bacteria for Potential Use as Carriers for In Vivo Applications"; Engineering in Medicine and Biology Society, 2007, EMBS 2007—29th Annual International Conference of the IEEE; Aug. 22-26, 2007; pp. 1463-1466; Abstract, 2 pgs.
Friedland et al.; "Synthetic Gene Networks That Count"; Science; May 29, 2009; pp. 1199-1202; vol. 324.
Garrait et al.; "Recombinant *Saccharomyces cerevisiae* Strain Expressing a Model Cytochrome P450 in the Rat Digestive Environment: Viability and Bioconversion Activity"; Applied and Environmental Microbiology; Jun. 2007; pp. 3566-3574; vol. 73, No. 11; American Society for Microbiology.

(56) References Cited

OTHER PUBLICATIONS

Glazer et al; "Microbial Biotechnology: Fundamentals of Applied Microbiology", Sep. 2007; 2$^{nd}$ edition; Table of Contents; 9 pgs.; Cambridge University Press..

Grangette et al.; "Enhanced Mucosal Delivery of Antigen with Cell Wall Mutants of Lactic Acid Bacteria"; Infection and Immunity; May 2004; pp. 2731-2737; vol. 72, No. 5; American Society for Microbiology.

Hagenbeek et al.; "Trivalent Ions Activate Abscisic Acid-Inducible Promoters through an ABII-Dependent Pathway in Rice Protoplasts"; Plant Physiology; Aug. 2000; pp. 1553-1560; vol. 123; American Society of Plant Physiologists.

Hanniffy et al.; "Potential and Opportunities for Use of Recombinant Lactic Acid Bacteria in Human Health"; Advances in Applied Microbiology; 2004; pp. 1-64; vol. 56; Elsevier, Inc.

Hansen et al.; "Detection of Oxytetracycline Production by *Streptomyces rimosus* in Soil Microcosms by Combining Whole-Cell Biosensors and Flow Cytometry"; Applied and Environmental Microbiology; Jan. 2001; pp. 239-244; vol. 67, No. 1; American Society for Microbiology.

Harlow & Lane: "Antibodies: A Laboratory Manual": 1988; 1$^{st}$ edition; Cold Spring Harbor Laboratory Press.

Hoensch et al.; "Monooxygenase enzyme activity in alcoholics with varying degrees of liver damage"; Gut; 1979; pp. 666-672; vol. 20.

Jensen et al.; "A Substrate-Dependent Biological Containment System for *Pseudomonas putida* Based on the *Escherichia coli gef* Gene"; Applied and Environmental Microbiology; Nov. 1993; pp. 3713-3717; vol. 59, No. 11; American Society for Microbiology.

Kambris et al.; "Immune Activation by Life-Shortening *Wolbachia* and Reduced Filarial Competence in Mosquitoes"; Science; Oct. 2, 2009; pp. 134-136; vol. 326.

Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.

Knudsen et al.; "Development of Efficient Suicide Mechanisms for Biological Containment of Bacteria"; Applied and Environmental Microbiology; Jan. 1991; pp. 85-92; vol. 57, No. 1; American Society for Microbiology.

Kojima et al.; "Carbon source nutrition of rapamycin biosynthesis in *Streptomyces hygroscopicus*"; Journal of Industrial Microbiology; 1995; pp. 436-439; Abstract; I pg.; vol. 14; Society for Industrial Microbiology.

Kupper et al.; "Generation of human antibody fragments against *Streptococcus mutans* using a phase display chain shuffling approach"; BMC Biotechnology; 2005; pp. 1-12; vol. 5, No. 4; BioMed Central Ltd.

Lee et al.; "A Propionate-Inducible Expression System for Enteric Bacteria"; Applied and Environmental Microbiology; Nov. 2005; pp. 6856-6862; vol. 71, No. 11; American Society for Microbiology.

Lee et al.; "A Type I-Secreted, Sulfated Peptide Triggers XA21-Mediated Innate Immunity"; Science; Nov. 6, 2009; pp. 850-853.

Maassen et al.; "Instruments for oral disease-intervention strategies: recombinant *Lactobacillus casei* expressing tetanus toxin fragment C for vaccination or myelin proteins for oral tolerance induction in multiple sclerosis"; Vaccine; Apr. 23, 1999; pp. 2117-2128; vol. 17, No. 17; Abstract; 1 pg.

Madsen et al.; "Two acid-inducible promoters from *Lactococcus lactis* require the *cis*-acting ACiD-box and the transcription regulator RcfB"; Molecular Biology; May 2005; pp. 735-746; vol. 56, No. 3; Abstract, 2 pgs.; Blackwell Publishing.

Maillard et al.; "Structural diversity in twin-arginine signal peptide-binding proteins"; PNAS; Oct. 2, 2007; pp. 15641-15646; vol. 104, No. 40; The National Academy of Sciences of the USA.

Mallonee et al.; "Cloning and Sequencing of a Bile Acid-Inducible Operon from *Eubacterium* sp. Strain VP1 12708"; Journal of Bacteriology; Dec. 1990; pp. 7011-7019; vol. 172, No. 12; American Society for Microbiology.

Marx, Christopher J.; "Getting in Touch with Your Friends"; Science; May 29, 2009; pp. 1150-1151; vol. 324, No. 5931; Abstract, 1 pg.

Müller et al., "Microbial Degradation of Halogenated Hydrocarbons: A Biological Solution to Pollution Problems?"; Angewandt Chemie Int Ed English, Dec. 22, 2003; pp. 779-789; vol. 25, No. 9; Abstract, 2 pgs.; Wiley-VCH Verlag GmbH, Weinheim.

Myers et al.; "MtrB Is Required for Proper Incorporation of the Cytochromes OmcA and OmcB into the Outer Membrane of *Shewanella putrefaciens* MR-1"; Applied and Environmental Microbiology; Nov. 2002; pp. 5585-5594; vol. 68, No. 11; American Society for Microbiology.

Myles et al.; "An assessment of the portability of ancestry informative markers between human populations"; BMC Medical Genomics; 2009; pp. 1-10, vol. 2, No. 45; BioMed Central Ltd.

National Center Biotechnology Information (NCBI) Single Nucleotide Polymorphisms, on the worldwide web at ncbi.nlm.nih.gov/projects/SNP/; 2 pgs. Oct. 2009.

O'Hara et al.; "The gut flora as a forgotten organ"; EMBO reports; 2006; pp. 688-693; vol. 7, No. 7; European Molecular Biology Organization.

Peppas et al.; "Polymers and Gels as Molecular Recognition Agents"; Pharmaceutical Research; May 2002; pp. 578-587; vol. 19, No. 5; Plenum Publishing Corporation.

Pinkel et al.; "Array comparative genomic hybridization and its applications in cancer"; Nature Genetics Supplement; Jun. 2005; pp. S11-S17; vol. 37; Nature Publishing Group.

Ramos et al.; "The behavior of bacteria designed for biodegradation."; Biotechnology; Dec. 1994; pp. 1349-1356; vol. 12, No. 13; Abstract; 1 pg.

Rao et al.; "Toward a live microbial microbicide for HIV: Commensal bacteria secreting an HIV fusion inhibitor peptide"; PNAS: Aug. 23, 2005; pp. 11993-11998; vol. 102, No. 34.

Richter et al.; "Determination of the minimal acid-inducible promoter region of the *lipF* gene from *Mycobacterium tuberculosis*"; Gene; 2006; Abstract; 2 pgs.; Elsevier B.V.

Ryu et al.; "Bacterial volatiles promote growth in *Arabidopsis*"; PNAS; Apr. 15, 2003; pp. 4927-4932; vol. 100, No. 8.

Sambrook et al.; "Molecular Cloning: A Laboratory Manual"; 2$^{nd}$ ed.; 1989; 2 pgs.; Cold Spring Harbor Laboratory Press, N.Y.

Sargent et al.; "Studies on Foliar Penetration; VI. Factors Controlling the Penetration of 4-Amino-3,5,6-Tri-Chloropicolinic Acid (Picloram) into the Leaves of *Phaseolus vulgaris*"; Journal of Experimental Botany; 1970; pp. 219-227; vol. 21, No. 1; Abstract, 2 pgs.; Oxford University Press.

Shim et al.; "Rhizosphere Competitiveness of Trichloroethylene-Degrading, Poplar-Colonizing Recombinant Bacteria"; Applied and Environmental Microbiology; Nov. 2000; pp. 4673-4678; vol. 66, No. 11; American Society for Microbiology.

Shou et al.; "Synthetic cooperation in engineered yeast populations"; PNAS; Feb. 6, 2007; pp. 1877-1882; vol. 104, No. 6; The National Academy of Sciences of the USA.

Smith et al.; "Functional expression of plant acetolactate synthase genes in *Escherichia coli*"; Genetics; Jun. 1989; pp. 4179-4183; vol. 86; PNAS USA.

Steidler et al.; "Biological containment of genetically modified *Lactococcus lactis* for intestinal delivery of human interleukin 10"; Nature Biotechnology; Jul. 2003; pp. 785-789; vol. 21, No. 7; Nature Publishing Group.

Steidler et al.; "Mucosal Delivery of Murine Interleukin-2 (IL-2) and IL-6 by Recombinant Strains of *Lactococcus lactis* Coexpressing Antigen and Cytokine"; Infection and Immunity; Jul. 1998; pp. 3183-3189; vol. 66, No. 7; American Society for Microbiology.

Stritzker et al.; "Tumor-specific colonization, tissue distribution, and gene induction by probiotic *Escherichia coli* Nissle 1917 in live mice"; International Journal of Medical Microbiology; 2007; pp. 151-162; vol. 297; Elsevier GmbH.

Suyama et al.; "Phylogenetic Affiliation of Soil Bacteria That Degrade Aliphatic Polyesters Available Commercially as Biodegradable Plastics"; Applied and Environmental Microbiology; Dec. 1998; pp. 5008-5011; vol. 64, No. 12; American Society for Microbiology.

Swindell et al.; "Genetic Manipulation of the Pathway for Diacetyl Metabolism in *Lactococcus lactis*"; Applied and Environmental Microbiology; Jul. 1996; pp. 2641-2643; vol. 62, No. 7; American Society for Microbiology.

(56) References Cited

OTHER PUBLICATIONS

Syvänen, Ann-Christine; "Toward genome-wide SNP genotyping"; Nature Genetics Supplement; Jun. 2005; pp. S5-S10; vol. 37; Nature Publishing Group.

Taghavi et al.; "Genome Survey and Characterization of Endophytic Bacteria Exhibiting a Beneficial Effect on Growth and Development of Poplar Trees"; Applied and Environmental Microbiology; Feb. 2009; pp. 748-757; vol. 75, No. 3; American Society for Microbiology.

Tawata et al.; "Screening for Genetic Mutations. A Review"; Combinatorial Chemistry & High Throughput Screening; 2000; pp. 1-9; vol. 3; Bentham Science Publishers B.V.

Taylor et al.; "Transcription from a heat-inducible promoter causes heat shock regulation of the sigma subunit of *E. coli* RNA polymerase"; Cell; Sep. 1984; pp. 371-381; vol. 38, No. 2; Abstract; 1 pg.

The International Hapmap Consortium; "A second generation human haplotype map of over 3.1 million SNPs"; Nature; Oct. 18, 2007; pp. 851-861; vol. 449; Nature Publishing Group.

Theys et al.; "Tumor-Specific Gene Delivery Using Genetically Engineered Bacteria"; Current Gene Therapy; Jun. 2003; pp. 207-221; vol. 3, No. 3; Abstract; 1 pg.

Wadolkowski et al.; "Colonization of the Streptomycin-Treated Mouse Large Intestine by a Human Fecal *Escherichia coli* Strain: Role of Growth in Mucus"; Infection and Immunity; May 1988; pp. 1030-1035; vol. 56, No. 5; American Society for Microbiology.

Wang et al.: "Cloning and expression of a lignin peroxidase gene from *Streptomyces viridosporus* in *Streptomyces lividans*"; Journal of Biotechnology; 1990; pp. 131-144; vol. 13; Elsevier Science Publishers B.V.

Wang et al.; "Characterization of two temperature-inducible promoters newly isolated from *B. subtillis*"; Biochemical and biophysical research communications; 2007; pp. 1148-1153; vol. 358, No. 4; Abstract; 1 pg.

Widdick et al.; "The twin-arginine translocation pathway is a major route of protein export in *Streptomyces coelicolor*"; PNAS; Nov. 21, 2006; pp. 17927-17932; vol. 103, No. 47.

Wilson et al.; "Species-specific detection of hydrocarbon-utilizing bacteria"; Journal of Microbiological Methods; Dec. 1999; pp. 59-78; vol. 39, No. 1; Abstract; pp. 1-4; Elsevier Science B.V.

Ye et al.; "Molecularly imprinted polymers as antibody and receptor mimics for assays, sensors and drug discovery"; Anal Bioanal Chem; 2004; pp. 1887-1897; vol. 378; Springer-Verlag.

Zhang et al.; "The histidine utilization (hut) genes of *Pseudomonas fluorescens* SBW25 are active on plant surfaces, but are not required for competitive colonization of sugar beet seedlings"; Microbiology; 2006; pp. 1867-1875; vol. 152; SGM.

Remington: The Science and Practice of Pharmacy; $21^{st}$ Edition; Cover page and Table of Contents (3 pgs.); Lippincott Williams & Wilkins, Baltimore, Maryland, Dec. 2000.

Win et al.; "Higher-Order Cellular Information Processing with Synthetic RNA Devices"; Science; Oct. 17, 2008; pp. 456-460; vol. 322, No. 5900.

Zhang et al.; "Human gut microbiota in obesity and after gastric bypass"; PNAS; Feb. 17, 2009; pp. 2365-2370; vol. 106, No. 7; The National Academy of Sciences of the USA.

\* cited by examiner

FIG. 5

500 A delivery device, comprising:

505 a housing including at least one reservoir containing at least one composition, the at least one composition including at least one first constituent including at least one auxotrophic microorganism including at least one pH inducible promoter operably coupled to at least one heterologous genetic element encoding at least one therapeutic agent, and at least one genetic element inducible to initiate death of the at least one auxotrophic microorganism;

515 and at least one second constituent including at least one metabolite required by the at least one auxotrophic microorganism;

520 the reservoir configured to receive, retain, and dispense at least a portion of the at least one composition;

530 and at least one component configured to administer the at least one composition to at least one biological tissue

FIG. 6

| |
|---|
| 600 wherein the at least one composition further includes at least one pharmaceutically-acceptable carrier or excipient |
| 610 wherein the at least one first constituent of the composition and the at least one second constitutent of the composition are located in different reservoirs of the delivery device |
| 620 wherein the device is implantable |
| 630 wherein the device is implanted into a subject |
| 640 wherein the device is external to a subject |
| 650 wherein at least one component configured to administer the at least one composition to at least one biological tissue includes one or more ports |
| 660 wherein at least one of the one or more ports includes at least one outlet port or at least one inlet port |
| 670 wherein each reservoir includes at least one separate port |
| 680 wherein the delivery device includes at least one reservoir including at least one inducer formulated to induce at least one promoter operably coupled to the at least one genetic element inducible to initiate death of the at least one auxotrophic microorganism |

FIG. 7

700 further comprising one or more controllable output mechanisms operably linked to the one or more ports to control dispensing of at least a portion of the at least one composition from the at least one reservoir 710 wherein the at least one controllable output mechanism includes at least one of a micropump, valve, injector, or actuator 720 wherein the valve includes at least one of a one-way valve, or pressure settable valve 730 wherein the actuator includes at least one of a piezoelectric actuator, electrostatic actuator, thermal actuator, shape-memory alloy actuator, bioactuator, or magnetic actuator 740 wherein the at least one controllable output mechanism includes at least one thermal or nonthermal gate in communication with the at least one outlet of the at least one reservoir 750 further comprising at least one control circuitry configured to control the at least one controllable output mechanism 760 wherein the at least one control circuitry is configured to control the release of the at least two constituents of the composition 770 wherein at least one of the rate of release, amount of release, or time of release of the at least two constituents of the composition are different for each constituent 780 wherein the at least one control circuitry is configured to generate and transmit an electromagnetic control signal configured to control the at least one controllable output mechanism 790 wherein the at least one control circuitry is configured to control the at least one controllable output mechanism for time-release of at least a portion of the at least one composition from the at least one reservoir

FIG. 8

| |
|---|
| 800 wherein the at least one control circuitry is configured for variable programming control of the at least one controllable output mechanism |
| 810 wherein the at least one control circuitry is configured to control release of at least a portion of the composition |
| 815 wherein the at least one control circuitry is configured to control release of at least a portion of the composition in response to a signal from a sensor |
| 820 wherein the at least one control circuitry is configured to control release of at least one inducer formulated to activate at least one promoter operably coupled to the at least one genetic element inducible to initiate death of the at least one auxotrophic microorganism |
| 830 further comprising at least one injector |
| 840 further comprising at least one transducer |
| 850 further comprising at least one receiver |
| 860 wherein the at least one receiver is configured to receive information from at least one distal or remote sensor |
| 870 wherein the receiver is configured to obtain release instructions or authorization to release the at least one composition |
| 875 wherein the receiver is configured to receive programming instructions or data for the controller |
| 880 further comprising at least one transmitter |
| 885 wherein the at least one transmitter is configured to transmit information regarding one or more of the date, time, presence or approximate quantity of one or more of at least a portion of the at least one composition, at least one constituent thereof, or at least one product thereof; at least one cell or substance associated with the at least one biological tissue; at least one metabolite associated with the at least one biological tissue; or at least one microorganism associated with the at least one biological tissue |
| 890 further comprising at least one circuit |

FIG. 9

900 further comprising at least one power source 910 further comprising at least detection material 915 further comprising at least one reservoir for controlled release of the at least one detection material 920 wherein the at least one detection material includes at least one of a radioactive, luminescent, colorimetric or odorous substance 930 wherein the at least one detection material includes at least one of a taggant, contrast agent, sensor, or electronic identification device 940 wherein the at least one electronic identification device includes at least one radio frequency identification device 950 wherein the at least one sensor includes at least one biosensor 960 wherein the at least one biosensor includes at least one modified microorganism 970 wherein the at least one sensor receives information associated with at least one of temperature, pH, inflammation, presence of at least one inducer, amount of at least one inducer, presence of at least one repressor, amount of at least one repressor, or biological response to administration of the at least one composition 980 wherein the at least one detection material includes at least one of a diamagnetic particle, ferromagnetic particle, paramagnetic particle, super paramagnetic particle, particle with altered isotope, or other magnetic particle 990 wherein the at least one detection material is responsive to the presence of at least one of the at least one composition, at least one constituent thereof, or at least one product thereof; at least one cell or substance associated with the at least one biological tissue; the at least one metabolite, or at least one product thereof, or the at least one therapeutic agent, or a by-product thereof

FIG. 10

1000 wherein the at least one detection material is responsive to the approximate quantity of at least one of the at least one composition, at least one constituent thereof, or at least one product thereof; at least one cell or substance associated with the at least one biological tissue; or the at least one metabolite, or at least one product thereof 1010 wherein the at least one detection material is responsive to the approximate number of microorganisms producing the at least one therapeutic agent 1020 wherein the at least one detection material is responsive to at least one of: enzyme, acid, amino acid, peptide, polypeptide, protein, oligonucleotide, nucleic acid, ribonucleic acid, oligosaccharide, polysaccharide, glycopeptide, glycolipid, lipoprotein, sphingolipid, glycosphingolipid, glycoprotein, peptidoglycan, lipid, carbohydrate, metalloprotein, proteoglycan, chromosome, adhesion molecule, cytokine, chemokine, immunoglobulin, antibody, antigen, platelet, extracellular matrix, blood plasma, cell wall, hormone, organic compound, inorganic compound, salt, or cell ligand 1030 wherein the at least one detection material is responsive to at least one of: glucose, lactate, urea, uric acid, glycogen, oxygen, carbon dioxide, carbon monoxide, ketone, nitric oxide, nitrous oxide, alcohol, alkaloid, opioid, cannabinol, endorphin, epinephrine, dopamine, serotonin, nicotine, amphetamine, methamphetamine, anabolic steroid, hydrocodone, hemoglobin, heparin, clotting metabolite, tumor antigen, pH, albumin, ATP, NADH, FADH$_2$, pyruvate, sulfur, mercury, lead, creatinine, cholesterol, alpha-fetoprotein, chorionic gonadotropin, estrogen, progesterone, testosterone, thyroxine, melatonin, calcitonin, antimullerian hormone, adiponectin, angiotensin, cholecystokinin, corticotrophin-releasing hormone, erythropoietin, bilirubin, creatine, follicle-stimulating hormone, gastrin, ghrelin, glucagon, gonadotropin-releasing hormone, inhibin, growth hormone, growth hormone-releasing hormone, insulin, human placental lactogen, oxytocin, orexin, luteinizing hormone, leptin, prolactin, somatostatin, thrombopoietin, cortisol, aldosterone, estradiol, estriol, estrone, leukotriene, brain natriuretic peptide, neuropeptide Y, histamine, vitamin, mineral, endothelin, renin, enkephalin, DHEA, DHT, alloisoleucine, toxic substance, illegal substance, therapeutic agent, or any metabolite thereof

FIG. 11

1100 further comprising at least one memory mechanism for storing instructions for generating and transmitting an electromagnetic control signal 1110 further comprising at least one imaging apparatus capable of imaging the approximate quantity within a treatment region of one or more of the at least one composition, at least one constituent thereof, or at least one product thereof; at least one cell or substance associated with the at least one biological tissue; or the at least one metabolite, or at least one product thereof 1120 further comprising at least one reservoir for controlled release of at least one inducer or repressor of the at least one heterologous genetic element encoding at least one therapeutic agent.

1130 further comprising at least one reservoir for controlled release of at least one inducer or repressor of the at least one genetic element inducible to initiate death of the at least one modified microorganism 1140 further comprising at least one memory location for recording information 1150 wherein the at least one memory location is configured to record information regarding at least one sensor 1160 wherein the at least one memory location is configured to record information regarding at least one of a sensed condition, history, or performance of the device 1170 wherein the at least one memory location is configured to record information regarding one or more of the date, time, presence or approximate quantity of at least one of the administered composition, constituent thereof, or product thereof; the at least one administered metabolite, or product thereof; or at least one cell or substance associated with the at least one biological tissue

FIG. 12

1200 wherein the at least one cell or substance associated with the at least one biological tissue includes at least one of an organic or inorganic small molecule, nucleic acid, amino acid, peptide, polypeptide, protein, glycopeptide, glycoprotein, glycolipid, lipopolysaccharide, peptidoglycan, proteoglycan, lipid, lipoprotein, sphingolipid, glycospingolipid, metalloprotein, metal, liposome, chromosome, nucleus, acid, base, buffer, protic solvent, aprotic solvent, carbohydrate, energy, arabinose, lactose, maltose, sucrose, glucose, xylose, xylan, nisin, L-arabinose, allolactose, D-glucose, D-xylose, D-galactose, ampicillin, tetracycline, penicillin, pristinamycin, retinoic acid, interferon, galactose, rhamnose, fructose, melibiose, starch, inunlin, lipopolysaccharide, arsenic, cadmium, hydrocarbon, chromium, mercury, antibiotic, oxygen, carbon dioxide, carbon monoxide, nitrogen, nitric oxide, vitamin, mineral, nitrous oxide, nitric oxide synthase, sulfur, gas, cytokine, chemokine, immunoglobulin, antibody, antigen, extracellular matrix, cell ligand, zwitterionic material, cationic material, oligonucleotide, nanotube, piloxymer, transfersome, gas, element, contaminant, radioactive particle, hormone, virus, enzyme, oligonucleotide, ribonucleic acid, oligosaccharide, polysaccharide, adhesion molecule, platelet, blood plasma, whole blood, cell wall, salt, cell ligand, lactate, urea, uric acid, glycogen, ketone, alcohol, alkaloid, opioid, cannabinol, endorphin, epinephrine, dopamine, serotonin, nicotine, amphetamine, methamphetamine, anabolic steroid, hydrocodone, hemoglobin, heparin, clotting metabolite, tumor antigen, pH, albumin, ATP, NADH, FADH$_2$, pyruvate, mercury, lead, creatinine, cholesterol, alpha-fetoprotein, chorionic gonadotropin, estrogen, progesterone, testosterone, thyroxine, melatonin, calcitonin, antimullerian hormone, adiponectin, angiotensin, cholecystokinin, corticotrophin-releasing hormone, erythropoietin, bilirubin, creatine, follicle-stimulating hormone, gastrin, ghrelin, glucagon, gonadotropin-releasing hormone, inhibin, growth hormone, growth hormone-releasing hormone, insulin, human placental lactogen, oxytocin, orexin, luteinizing hormone, leptin, prolactin, somatostatin, thrombopoietin, cortisol, aldosterone, estradiol, estriol, estrone, leukotriene, brain natriuretic peptide, neuropeptide Y, histamine, vitamin, mineral, endothelin, renin, enkephalin, DHEA, DHT, alloisoleucine, toxic substance, illegal substance, agent, hydrocarbon, arsenic, gold, silver, cadmium, strontium, mercury, lead, other heavy metals, chromium, antibiotic, gas, or any by-products thereof, plant cell, animal cell, fungal cell, blood cell, muscle cell, nerve cell, fibroblast, adipose cell, stem cell, pluripotent cell, epithelial cell, skin cell, neoplastic cell, tumor cell, cell mass, or other biological tissue or organ cell

FIG. 13

1300 further comprising at least one information transmission mechanism configured to transmit information recorded by the at least one electronic memory location 1310 wherein the device is located in or is substantially in the form of one or more of a spray apparatus, pump apparatus, bioreactor, or drilling apparatus 1320 wherein the device is located in or is substantially in the form of one or more of a patch, oral inhaler, nasal spray or other orifice spray, orifice insert, chewing gum, iontophoretic apparatus, oral consumable, ocular or otic dropper or spray, stent, shunt, consumer product, food product, food package, lip balm, lotion, ointment, sunscreen or sunblock, perfume, aftershave, shampoo or other hair products, nail polish, dentures or other oral implants, contact lens or other ocular implants, orifice insert, orifice spray or inhaler, sutures, surgical staples, dental floss, stents, shunts, bandages, absorbable mesh, or oral consumable 1330 further comprising at least one reservoir for controlled release of at least one inducer or repressor of the at least one heterologous genetic element encoding at least one therapeutic agent 1340 further comprising at least one reservoir for controlled release of at least one inducer or repressor of the at least one genetic element inducible to initiate death of the at least one modified microorganism 1350 further comprising a controller configured to respond to the at least one sensor 1360 wherein the at last one sensor is configured to sense information related to at least one of the at least one biological tissue, the therapeutic agent, or the composition or a constituent thereof 1370 wherein the information related to the at least one biological tissue includes at least one of temperature, pH, inflammation, or other characteristic

FIG. 14

1400 A delivery device, comprising:

1410 a housing including at least one reservoir containing at least one composition, the at least one composition including at least one modified microorganism including at least one heterologous genetic element encoding at least one environmental medium treatment agent, and at least one genetic element inducible to initiate death of the at least one modfiied microorganism;

1420 the reservoir configured to receive, retain, and dispense at least a portion of the at least one composition;

1430 and at least one component configured to administer the at least one composition to at least one environmental medium

FIG. 15

1500 wherein the at least one composition further comprises at least one metabolite required by the at least one modified microorganism 1510 wherein at least one component configured to administer the at least one composition includes one or more ports 1520 wherein at least one of the one or more ports includes at least one outlet port or at least one inlet port 1530 wherein each reservoir includes at least one separate port 1535 wherein the delivery device includes at least one reservoir including at least one inducer formulated to induce at least one promoter operably coupled to the at least one genetic element inducible to initiate death of the at least one modified microorganism 1538 further comprising one or more controllable output mechanisms operably linked to the one or more ports to control dispensing of at least a portion of the at least one composition from the at least one reservoir 1540 wherein the at least one controllable output mechanism includes at least one of a micropump, valve, injector, or actuator 1550 wherein the valve includes at least one of a one-way valve, or pressure settable valve 1560 wherein the actuator includes at least one of a piezoelectric actuator, electrostatic actuator, thermal actuator, shape-memory alloy actuator, bioactuator, or magnetic actuator 1570 wherein the at least one controllable output mechanism includes at least one thermal or nonthermal gate in communication with the at least one outlet of the at least one reservoir 1580 further comprising at least one control circuitry configured to control the at least one controllable output mechanism

FIG. 16

| 1600 wherein the at least one control circuitry is configured to control the at least one controllable output mechanism for time-release of at least a portion of the at least one composition from the at least one reservoir |
|---|

| 1610 wherein the at least one control circuitry is configured for variable programming control of the at least one controllable output mechanism |
|---|

| 1620 wherein the at least one control circuitry is configured to control the release of at least a portion of the composition |
|---|

| 1625 wherein the at least one control circuitry is configured to control the release of at least a portion of the composition in response to a signal from a sensor |
|---|

| 1628 wherein the at least one control circuitry is configured to control release of at least one inducer formulated to activate at least one promoter operably coupled to the at least one genetic element inducible to initiate death of the at least one modified microorganism |
|---|

| 1630 further comprising at least one reservoir for controlled release of at least one inducer or repressor of the at least one heterologous genetic element encoding at least one environmental medium treatment agent |
|---|

| 1650 further comprising at least one transducer |
|---|

| 1660 further comprising at least one receiver |
|---|

| 1670 wherein the receiver is configured to obtain release instructions or authorization to release the at least one composition |
|---|

| 1680 wherein the receiver is configured to receive programming instructions or data for the controller |
|---|

| 1685 wherein the receiver is configured to receive information from at least one distal or remote sensor |
|---|

| 1690 further comprising at least one transmitter |
|---|

FIG. 17

1700 wherein the at least one transmitter is configured to transmit information regarding one or more of the date, time, presence or approximate quantity of one or more of the at least one composition, at least one constituent thereof, or at least one product thereof; at least one cell or substance associated with the at least one environmental medium; at least one metabolite associated with the at least one environmental medium; or at least one organism associated with the at least one environmental medium 1710 wherein the delivery device includes at least one reservoir including at least one inducer formulated to induce at least one promoter operably coupled to the at least one genetic element inducible to initiate death of the at least one modified microorganism 1720 further comprising at least one power source 1730 further comprising at least one detection material 1740 further comprising at least one reservoir for controlled release of the at least one detection material 1750 wherein the at least one detection material includes at least one of a taggant, contrast agent, sensor, or electronic identification device 1760 wherein the at least one electronic identification device includes at least one radio frequency identification device 1770 wherein the at least one sensor includes at least one biosensor 1780 wherein the at least one biosensor includes at least one modified microorganism 1790 wherein the at least one sensor receives information associated with at least one of temperature, pH, presence of at least one inducer, amount of at least one inducer, presence of at least one repressor, amount of at least one repressor, or environmental response to administration of the at least one composition

FIG. 18

1800 wherein the at least one sensor is configured to sense information related to at least one of the environmental medium, the environmental treatment medium agent, or the composition or a constituent thereof 1810 wherein the information related to the at least one environmental medium includes at least one of temperature, pH, soil content, water content, mineral content, organic or inorganic matter content, or other characteristic 1820 further comprising a controller configured to respond to the at least one sensor 1830 wherein the at least one detection material includes at least one of a radioactive, luminescent, colorimetric or odorous substance 1840 wherein the at least one detection material includes at least one of a diamagnetic particle, ferromagnetic particle, paramagnetic particle, super paramagnetic particle, particle with altered isotope, or other magnetic particle 1850 wherein the at least one detection material is responsive to the presence of at least one of the at least one composition, at least one constituent thereof, or at least one product thereof; at least one cell or substance associated with the at least one environmental medium; at least one metabolite associated with the environmental medium; or at least one organism associated with the at least one environmental medium 1860 wherein the at least one organism associated with the at least one environmental medium includes at least one of a plant, animal, fungus, or microorganism 1870 wherein the at least one detection material is responsive to the approximate quantity of one or more of the at least one composition, at least one constituent thereof, or at least one product thereof; at least one cell or substance associated with the at least one environmental medium; at least one metabolite associated with the at least one environmental medium; or at least one organism associated with the at least one environmental medium

FIG. 19

1900 wherein the at least one organism associated with the at least one environmental medium includes at least one of a plant, animal, fungus, or microorganism 1910 wherein the at least one detection material is responsive to the approximate number of microorganisms producing the at least one treatment agent, or an environmental medium substance 1920 wherein the environmental medium substance includes one or more of an enzyme, acid, amino acid, peptide, polypeptide, protein, oligonucleotide, nucleic acid, ribonucleic acid, oligosaccharide, polysaccharide, glycopeptide, glycolipid, lipoprotein, sphingolipid, glycosphingolipid, glycoprotein, peptidoglycan, lipid, carbohydrate, metalloprotein, proteoglycan, chromosome, adhesion molecule, cytokine, chemokine, immunoglobulin, antibody, antigen, extracellular matrix, cell wall, hormone, organic compound, inorganic compound, salt, cell ligand, glucose, lactate, urea, uric acid, glycogen, oxygen, carbon dioxide, carbon monoxide, ketone, nitric oxide, nitrous oxide, alcohol, alkaloid, opioid, cannabinol, endorphin, epinephrine, dopamine, serotonin, nicotine, amphetamine, methamphetamine, pH, albumin, ATP, NADH, $FADH_2$, pyruvate, sulfur, mercury, lead, creatinine, cholesterol, estrogen, progesterone, testosterone, calcitonin, ghrelin, glucagon, inhibin, growth hormone, growth hormone-releasing hormone, insulin, vitamin, mineral, DHEA, DHT, alloisoleucine, toxic substance, illegal substance, hydrocarbon, arsenic, gold, silver, cadmium, strontium, mercury, lead, other heavy metals, chromium, antibiotic, gas, or any by-products thereof, a microorganism, plant cell, animal cell, fungal cell, plant, animal, fungus, or other organism 1925 wherein the at least one detection material is responsive to the approximate number of microorganisms producing the at least one environmental medium treatment agent 1930 further comprising at least one memory mechanism for storing instructions for generating and transmitting an electromagnetic control signal 1940 further comprising at least one imaging apparatus capable of imaging the approximate quantity within a treatment region of one or more of the at least one composition, at least one constituent thereof, or at least one product thereof; at least one organism associated with the at least one environmental medium; at least one metabolite associated with the at least one environmental medium; or at least one cell or substance associated with the at least one environmental medium

FIG. 20

| |
|---|
| 2000 further comprising at least one memory location for recording information |
| 2010 wherein the at least one memory location is configured to record information regarding the at least one sensor |
| 2020 wherein the at least one memory location is configured to record information regarding at least one of a sensed condition, history, or performance of the device |
| 2030 wherein the at least one memory location is configured to record information regarding one or more of the date, time, presence or approximate quantity of dispensing of one or more of the at least one composition, at least one constituent thereof, or at least one product thereof; at least one cell or substance associated with the at least one environmental medium; at least one organism associated with the at least one environmental medium; or at least one metabolite associated with the at least one environmental medium |
| 2040 further comprising at least one information transmission mechanism configured to transmit information recorded by the at least one electronic memory location |
| 2050 wherein the device is located in or is substantially in the form of one or more of a patch or tarp, insert, mesh or netting, or at least one disposable or biodegradable product |
| 2060 wherein the device is located in or is substantially in the form of one or more of a food package, disposable package, bioreactor, spray apparatus, pump apparatus, or drilling apparatus |
| 2070 further comprising at least one reservoir for controlled release of at least one inducer or repressor of the at least one heterologous genetic element encoding at least one environmental medium treatment agent |
| 2080 further comprising at least one reservoir for controlled release of at least one inducer or repressor of the at least one genetic element inducible to initiate death of the at least one modified microorganism |

FIG. 21

2100 A system, comprising 2105 at least one computing device 2110 at least one delivery device configured to retain and dispense at least a portion of at least one composition to at least one biological tissue 2115 and a recordable medium including one or more instructions that when executed on the computing device cause the computing device to regulate dispensing of at least a portion of the at least one composition 2120 wherein the at least one composition includes at least one first constituent including at least one auxotrophic microorganism including at least one pH inducible promoter operably coupled to at least one heterologous genetic element encoding at least one therapeutic agent, and including at least one genetic element inducible to initiate death of the at least one auxotrophic microorganism; and at least one second constituent including at least one metabolite required by the at least one auxotrophic microorganism

FIG. 22

2200 wherein the at least one computing device includes at least one computing device located on or in the at least one delivery device 2210 wherein the at least one computing device includes at least one computing device located remotely from the at least one delivery device 2220 wherein the at least one computing device includes one or more of a desktop computer, workstation computer, or computing system 2230 wherein the at least one computing system includes one or more of a cluster of processors, a networked computer, a tablet personal computer, a laptop computer, a mobile device, a mobile telephone, or a personal digital assistant computer 2240 further comprising one or more instructions that when executed on the at least one computing device cause the at least one computing device to generate at least one output to a user 2250 wherein the at least one output includes at least one graphical illustration of one or more of the at least one composition, at least one constituent thereof, or at least one product thereof; at least one cell or substance associated with the at least one biological tissue; the at least one metabolite, or at least one product thereof; at least one property of the delivery device; or at least one property of dispensing the at least one delivery device 2260 wherein the at least one output includes at least one protocol for generating the at least one auxotrophic microorganism 2270 wherein the at least one output includes at least one protocol for making the at least one composition 2280 wherein the at least one output includes at least one protocol for administering the at least one composition to the at least one biological tissue

FIG. 23

2300 wherein the user includes at least one entity 2310 wherein the entity includes at least one person, or computer 2320 wherein the output includes output to a user readable display 2340 wherein the user readable display includes a human readable display 2350 wherein the user readable display includes one or more active displays 2360 wherein the user readable display includes one or more passive displays 2370 wherein the user readable display includes one or more of a numeric format, graphical format, or audio format 2380 further comprising one or more instructions for making the at least one composition 2390 further comprising one or more instructions for inducing the at least one pH inducible promoter operably coupled to at least one heterologous genetic element encoding at least one therapeutic agent 2395 further comprising one or more instructions for inducing the at least one genetic element inducible to initiate death of the at least one auxotrophic microorganism 2398 wherein the composition further comprises at least one repressor operably coupled to the at least one heterologous genetic element encoding at least one therapeutic agent

FIG. 24

2400 further comprising one or more instructions for selecting the composition, or a constituent thereof 2420 further comprising one or more instructions for administering the at least one composition or a constituent thereof to at least one biological tissue 2430 further comprising one or more instructions for receiving information related to one or more biological tissue indicators prior to, during, or subsequent to administering the at least one composition to the at least one biological tissue 2440 wherein the information related to one or more biological tissue indicators includes information from at least one of an assay, image, or gross assessment of the at least one biological tissue prior to, during, or subsequent to administering the at least one composition 2450 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 2460 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or *in silico* generation

FIG. 25

2500 further comprising one or more instructions for receiving information related to one or more biological tissue indicators relate to one or more of: administration of the at least one therapeutic agent, or a constituent thereof, or a product thereof; administration of the at least one composition, or a constituent thereof, or a product thereof; administration of the at least one metabolite; administration of the at least one auxotrophic microorganism; cell or tissue formation; cell or tissue growth; cell or tissue apoptosis; cell or tissue necrosis; cell division; cytoskeletal rearrangement; cell or tissue secretion; cell or tissue differentiation; status of the at least one auxotrophic microorganism of the at least one composition; status of the at least one composition; status of the at least one therapeutic agent; status of the at least one metabolite; or depletion of the at least one metabolite 2510 wherein the at least one biological tissue is located in at least one of *in situ, in vitro, in vivo, in utero, in planta, in silico,* or *ex vivo*

2520 wherein the at least one biological tissue is at least partially located in at least one subject 2530 wherein the at least one subject includes at least one of an invertebrate or vertebrate animal 2540 wherein the at least one subject includes at least one of a reptile, mammal, amphibian, bird, or fish 2550 wherein the at least one subject includes at least one human 2560 wherein the at least one subject includes at least one plant 2570 further comprising one or more instructions for obtaining genetic sequence information from at least one microorganism isolated from the at least one biological tissue

FIG. 26

2600 further comprising one or more instructions for modifying the at least one microorganism isolated from the at least one biological tissue 2610 further comprising one or more instructions for amplifying the at least one microorganism isolated from the at least one biological tissue 2620 further comprising one or more instructions for reinstating the at least one microorganism isolated from the at least one biological tissue subsequent to modification 2630 further comprising one or more instructions for predetermining at least one microorganism type for modifying to produce at least one therapeutic agent based on at least one feature of the at least one biological tissue 2640 wherein the at least one feature of the at least one biological tissue includes at least one property of one or more microorganism populations associated with the at least one biological tissue

FIG. 27

2700 A computer-implemented method, comprising:

2710 one or more instructions for regulating dispensing at least one composition from at least one delivery device to at least one biological tissue, the at least one composition including at least one auxotrophic microorganism including at least one pH inducible heterologous genetic element encoding at least one therapeutic agent formulated for at least one biological tissue, and including at least one genetic element inducible to initiate death of the at least one auxotrophic microorganism; and at least one metabolite required by the at least one auxotrophic microorganism 2720 further comprising generating at least one output to a user 2730 wherein the at least one output includes at least one graphical illustration of one or more of the at least one composition, at least one constituent thereof, or at least one product thereof; the at least one metabolite, or at least one product thereof; at least one cell or substance associated with the at least one biological tissue; at least one property of the at least one delivery device; or at least one property of dispensing the at least one delivery device 2740 wherein the at least one output includes at least one protocol for generating the at least one auxotrophic microorganism 2750 wherein the at least one output includes at least one protocol for making the at least one composition 2760 wherein the at least one output includes at least one protocol for administering the at least one composition to the at least one biological tissue

FIG. 28

- 2800 wherein the user includes at least one entity
- 2810 wherein the entity includes at least one person, or computer
- 2820 wherein the at least one output includes at least one output to a user readable display
- 2830 wherein the user readable display includes a human readable display
- 2840 wherein the user readable display includes one or more active displays
- 2850 wherein the user readable display includes one or more passive displays
- 2860 wherein the user readable display includes one or more of a numeric format, graphical format, or audio format
- 2870 further comprising one or more instructions for making the at least one composition
- 2880 further comprising one or more instructions to dispense the at least one composition or a constituent thereof to at least one biological tissue

FIG. 29

| |
|---|
| 2900 further comprising one or more instructions for dispensing at least one inducer formulated to induce the at least one genetic element inducible to initiate death of the at least one auxotrophic microorganism |
| 2910 further comprising receiving information related to one or more biological tissue indicators prior to, during, or subsequent to administering the at least one composition or a constituent thereof, to the at least one biological tissue |
| 2920 further comprising one or more instructions for dispensing the at least one composition or a constituent thereof, to the at least one biological tissue in response to the one or more biological tissue indicators |
| 2930 further comprising one or more instructions for dispensing at least one inducer formulated to induce the at least one genetic element inducible to initiate death of the at least one auxotrophic microorganism, to the at least one biological tissue in response to the one or more biological tissue indicators |
| 2940 wherein the receiving information related to one or more biological tissue indicators includes information from at least one of an assay, image, or gross assessment of the at least one biological tissue prior to, during, or subsequent to administering the at least one composition |
| 2950 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay |
| 2960 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or *in silico* generation |

FIG. 30

3000 wherein the one or more biological tissue indicators relate to one or more of: administration of the at least one therapeutic agent, or constituent thereof, or product thereof; administration of the at least one composition, or constituent thereof, or product thereof; administration of the at least one metabolite; administration of the at least one auxotrophic microorganism; cell or tissue formation; cell or tissue growth; cell or tissue apoptosis; cell or tissue necrosis; cell division; cytoskeletal rearrangement; cell or tissue secretion; cell or tissue differentiation; status of the at least one auxotrophic microorganism of the at least one composition; status of the at least one composition; status of the at least one therapeutic agent; status of the at least one metabolite; or depletion of the at least one metabolite 3010 wherein the at least one biological tissue is located in at least one of *in situ, in vitro, in vivo, in utero, in planta, in silico,* or *ex vivo*

3020 wherein the at least one biological tissue is at least partially located in at least one subject 3030 wherein the at least one subject includes at least one of an invertebrate or vertebrate animal 3040 wherein the at least one subject includes at least one of a reptile, mammal, amphibian, bird, or fish 3050 wherein the at least one subject includes at least one human 3060 wherein the at least one subject includes at least one plant 3070 further comprising obtaining genetic sequence information from at least one microorganism isolated from the at least one biological tissue

FIG. 31

| |
|---|
| 3100 further comprising one or more instructions for modifying the at least one microorganism isolated from the at least one biological tissue |

| |
|---|
| 3110 further comprising one or more instructions for amplifying the at least one microorganism isolated from the at least one biological tissue |

| |
|---|
| 3120 further comprising one or more instructions for replacing the at least one microorganism isolated from the at least one biological tissue subsequent to modification |

| |
|---|
| 3130 further comprising one or more instructions for predetermining at least one microorganism type for modifying to produce at least one therapeutic agent based on at least one feature of the at least one biological tissue |

| |
|---|
| 3140 wherein the at least one feature of the at least one biological tissue includes at least one property of one or more microorganism populations associated with the at least one biological tissue |

FIG. 32

3200 A computer program product, comprising:

3210 a recordable medium bearing one or more instructions for regulating dispensing of at least one delivery device, wherein the delivery device includes at least one composition, wherein the at least one composition includes at least one auxotrophic microorganism including at least one pH inducible heterologous genetic element encoding at least one therapeutic agent formulated for at least one biological tissue, and including at least one genetic element inducible to initiate death of the at least one auxotrophic microorganism; at least one metabolite required by the at least one auxotrophic microorganism; and generating at least one output 3220 wherein the recordable medium includes a computer-readable medium 3230 wherein the recordable medium includes a communications medium 3240 further comprising one or more instructions for receiving information related to one or more biological tissue indicators prior to, during, or subsequent to administering the at least one composition 3250 wherein the one or more biological tissue indicators include one or more of: delivery of the at least one therapeutic agent, delivery of the at least one composition, delivery of the at least one metabolite, delivery of the at least one auxotrophic microorganism, cell or tissue formation, cell or tissue growth, cell or tissue apoptosis, cell or tissue necrosis, cell division, cytoskeletal rearrangement, cell or tissue secretion, cell or tissue differentiation, status of the at least one microorganism of the at least one composition, status of the at least one composition, status of the at least one therapeutic agent, status of the at least one metabolite, or depletion of the at least one metabolite 3260 further comprising one or more instructions for obtaining genetic sequence information from at least one microorganism isolated from the at least one biological tissue

FIG. 33

| |
|---|
| 3300 further comprising one or more instructions for modifying the at least one microorganism isolated from the at least one biological tissue |
| 3310 further comprising one or more instructions for amplifying the at least one microorganism isolated from the at least one biological tissue |
| 3320 further comprising one or more instructions for reinstating the at least one microorganism isolated from the at least one biological tissue subsequent to modification |
| 3330 further comprising one or more instructions for predetermining at least one microorganism type for modifying to produce at least one therapeutic agent based on at least one feature of the at least one biological tissue |
| 3340 wherein the at least one feature of the at least one biological tissue includes at least one property of one or more microorganism populations associated with the at least one biological tissue |
| 3350 wherein the output includes at least one protocol for making the at least one composition |
| 3360 wherein the output includes at least one protocol for generating the at least one auxotrophic microorganism |
| 3370 wherein the output includes at least one protocol for administering the at least one composition to at least one biological tissue |
| 3380 wherein the output includes at least one the output includes at least one graphical illustration of one or more of the at least one composition, at least one constituent thereof, or at least one product thereof; the at least one metabolite, or at least one product thereof; at least one cell or substance associated with the at least one biological tissue; at least one property of the at least one delivery device; or at least one property of dispensing the at least one delivery device.graphical description of one or more of the at least one composition, a constituent thereof, or product thereof; information related to at least one microorganism associated with the at least one biological tissue; or information related to at least one cell or substance associated with the at least one biological tissue |
| 3390 further comprising one or more instructions for displaying results of the processing |

FIG. 34

3400 A system, comprising:

3405 at least one computing device;

3410 at least one delivery device configured to retain and dispense at least one composition to at least one environmental medium;

3415 and a recordable medium including one or more instructions that when executed on the computing device cause the computing device to regulate dispensing of at least a portion of the at least one composition, 3420 wherein the at least one composition includes at least one modified microorganism including at least one heterologous genetic element encoding at least one environmental medium treatment agent; and at least one genetic element inducible to initiate death of the at least one modified microorganism.

FIG. 35

3500 wherein the at least one computing device includes at least one computing device located on or in the at least one delivery device 3510 wherein the at least one computing device includes at least one computing device located remotely from the at least one delivery device 3520 wherein the at least one computing device includes one or more of a desktop computer, workstation computer, or computing system 3530 wherein the at least one computing system includes one or more of a cluster of processors, a networked computer, a tablet personal computer, a laptop computer, a mobile device, a mobile telephone, or a personal digital assistant computer 3540 further comprising one or more instructions that when executed on the at least one computing device cause the at least one computing device to generate at least one output to a user 3550 wherein the at least one output includes at least one graphical illustration of one or more of the at least one composition, at least one constituent thereof, or at least one product thereof; at least one cell or substance associated with the at least one biological tissue; the at least one metabolite, or at least one product thereof; at least one property of the delivery device; or at least one property of dispensing the at least one delivery device 3560 wherein the at least one output includes at least one protocol for generating the at least one modified microorganism 3570 wherein the at least one output includes at least one protocol for making the at least one composition 3580 wherein the at least one output includes at least one protocol for administering the at least one composition to the at least one environmental medium

FIG. 36

3600 wherein the user includes at least one entity 3610 wherein the entity includes at least one person, or computer 3620 wherein the output includes output to a user readable display 3640 wherein the user readable display includes a human readable display 3650 wherein the user readable display includes one or more active displays 3660 wherein the user readable display includes one or more passive displays 3670 wherein the user readable display includes one or more of a numeric format, graphical format, or audio format 3680 wherein the at least one environmental medium includes at least one of water, soil, food product, or air or other gas 3690 wherein the at least one environmental medium includes at least one of ground water, surface water, effluent, or wastewater 3695 wherein the water includes at least one of a lake, river, stream, sewage, sludge, slurry, sediment, ocean, fountain, or other water 3696 wherein the at least one environmental medium includes at least one of metal, concrete, cement, textiles, fabric, wood, mineral ore, or rock 3697 wherein the at least one environmental medium treatment agent includes at least one plant hormone 3698 wherein the at least one plant hormone includes at least one of an auxin, abscisic acid, cytokinin, ethylene, gibberellin, brassinolide, salicyclic acid, jasmonate, polyamine, plant peptide hormone, nitric oxide, stigolactone, or other compound

FIG. 37

3700 further comprising one or more instructions for obtaining genetic sequence information from at least one microorganism isolated from the at least one environmental medium 3710 further comprising one or more instructions for modifying the at least one microorganism isolated from the at least one environmental medium 3720 further comprising one or more instructions for amplifying the at least one microorganism isolated from the at least one environmental medium 3730 further comprising one or more instructions for reinstating the at least one microorganism isolated from the at least one environmental medium subsequent to modification 3740 further comprising one or more instructions for predetermining at least one microorganism type for modifying to produce at least one environmental treatment agent based on at least one feature of the environmental medium 3750 wherein the at least one feature of the at least one environmental medium includes at least one property of one or more microorganism populations associated with the at least one environmental medium 3760 further comprising one or more instructions for making the at least one composition 3770 further comprising one or more instructions for inducing at least one inducible promoter operably coupled to at least one heterologous genetic element encoding at least one environmental medium treatment agent 3780 further comprising one or more instructions for inducing the at least one genetic element inducible to initiate death of the at least one modified microorganism 3790 further comprising one or more instructions for selecting the composition, or a constituent thereof 3795 further comprising one or more instructions for administering the at least one composition or a constituent thereof to at least one environmental medium

FIG. 38

3800 A computer-implemented method, comprising:

3810 one or more instructions for regulating dispensing at least one composition from at least one delivery device to at least one environmental medium, the at least one composition including at least one modified microorganism including at least one heterologous genetic element encoding at least one environmental medium treatment agent; and at least one genetic element inducible to initiate death of the at least one modified microorganism

3900 wherein the user includes at least one entity 3910 wherein the entity includes at least one person, or computer 3920 wherein the at least one output includes at least one output to a user readable display 3930 wherein the user readable display includes a human readable display 3940 wherein the user readable display includes one or more active displays 3950 wherein the user readable display includes one or more passive displays 3960 wherein the user readable display includes one or more of a numeric format, graphical format, or audio format 3970 further comprising one or more instructions for making the at least one composition 3980 further comprising one or more instructions to dispense the at least one composition or a constituent thereof to at least one environmental medium

FIG. 40

| |
|---|
| 4000 further comprising one or more instructions for dispensing at least one inducer formulated to induce the at least one genetic element inducible to initiate death of the at least one modified microorganism |
| 4010 further comprising receiving information related to one or more environmental medium indicators prior to, during, or subsequent to administering the at least one composition or a constituent thereof, to the at least one environmental medium |
| 4020 further comprising one or more instructions for dispensing the at least one composition or a constituent thereof, to the at least one environmental medium in response to the one or more environmental medium indicators |
| 4030 further comprising one or more instructions for dispensing at least one inducer formulated to induce the at least one genetic element inducible to initiate death of the at least one modified microorganism, to the at least one environmental medium in response to the one or more environmental medium indicators |
| 4040 wherein the receiving information related to one or more environmental medium indicators includes information from at least one of an assay, image, or gross assessment of the at least one environmental medium prior to, during, or subsequent to administering the at least one composition |
| 4050 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay |
| 4060 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or *in silico* generation |

FIG. 41

4100 wherein the one or more environmental medium indicators relate to one or more of: administration of the at least one composition, or a constituent thereof, or a product thereof; administration of at least one metabolite utilizable by the at least one modified microorganism; administration of the at least one modified microorganism; status of the at least one modified microorganism of the at least one composition; status of the at least one composition; status of the at least one environmental medium treatment agent; status of at least one metabolite utilizable by the modified microorganism; or depletion of at least one metabolite utilizable by the at least one modified microorganism 4110 further comprising obtaining genetic sequence information from at least one microorganism isolated from the at least one environmental medium 4120 further comprising one or more instructions for modifying the at least one microorganism isolated from the at least one environmental medium 4130 further comprising one or more instructions for amplifying the at least one microorganism isolated from the at least one environmental medium 4140 further comprising one or more instructions for reinstating the at least one microorganism isolated from the at least one environmental medium subsequent to modification 4150 further comprising one or more instructions for predetermining at least one microorganism type for modifying to produce at least one environmental medium treatment agent based on at least one feature of the at least one environmental medium 4160 wherein the at least one feature of the at least one environmental medium includes at least one property of one or more microorganism populations associated with the at least one environmental medium

FIG. 42

4200 A computer program product, comprising:

4210 a recordable medium bearing one or more instructions for regulating dispensing of at least one delivery device, wherein the delivery device includes at least one composition, wherein the at least one composition includes at least one modified microorganism including at least one heterologous genetic element encoding at least one environmental medium treatment agent; at least one genetic element inducible to initiate death of the at least one modified microorganism; and generating at least one output 4220 wherein the recordable medium includes a computer-readable medium 4230 wherein the recordable medium includes a communications medium 4233 further comprising one or more instructions for obtaining genetic sequence information from at least one microorganism isolated from the at least one environmental medium 4235 further comprising one or more instructions for displaying results of the processing 4240 further comprising one or more instructions for receiving information related to one or more environmental medium indicators prior to, during, or subsequent to administering the at least one composition 4250 wherein the one or more environmental medium indicators include one or more of: administration of the at least one composition, or constituent thereof, or product thereof; administration of at least one metabolite utilizable by the modified microorganism; administration of the at least one modified microorganism; status of the at least one modified microorganism of the at least one composition; status of the at least one composition; status of the at least one environmental medium treatment agent; status of at least one metabolite utilizable by the modified microorganism; or depletion of at least one metabolite utilizable by the modified microorganism

FIG. 43

| 4300 wherein the output includes at least one protocol for making the at least one composition |

| 4310 wherein the output includes at least one protocol for generating the at least one modified microorganism |

| 4320 wherein the output includes at least one protocol for administering the at least one composition to at least one environmental medium |

| 4330 wherein the output includes at least one graphical description of one or more of the at least one composition, constituent thereof, or product th

COMPOSITIONS AND METHODS FOR THERAPEUTIC DELIVERY WITH MICROORGANISMS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application is related to U.S. patent application Ser. No. 12/657,606, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr., and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application is related to U.S. patent application Ser. No. 12/657,608, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr., and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application is related to U.S. patent application Ser. No. 12/657,604, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr., and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application is related to U.S. patent application Ser. No. 12/657,609, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr., and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application is related to U.S. patent application Ser. No. 12/657,605, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr., and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,605, Docket No. 0905-002-030E-000000, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr., and Lowell L. Wood, Jr. as inventors, filed 22 Jan. 2010, which is currently co-pending, or is an application of which a currently co-pending application is entitled to the benefit of the filing date.

SUMMARY

Particular embodiments disclosed herein relate to various compositions, methods of administering, computer systems, computer-implemented methods, and associated products related to compositions including modified microorganisms modified to produce particular agents for at least one substrate.

In an embodiment, a composition comprises: at least one auxotrophic microorganism including at least one pH inducible promoter operably coupled to at least one heterologous genetic element encoding at least one therapeutic agent for at least one biological tissue, and including at least one genetic element inducible to initiate death of the at least one auxotrophic microorganism; and wherein the at least one composition includes at least one metabolite required by the at least one auxotrophic microorganism.

In an embodiment, a composition comprises: at least one auxotrophic microorganism including at least one temperature inducible promoter operably coupled to at least one heterologous genetic element encoding at least one therapeutic agent for at least one biological tissue, and including at least one genetic element inducible to initiate death of the at least one auxotrophic microorganism; and wherein the at least one composition includes at least one metabolite required by the at least one auxotrophic microorganism.

In an embodiment, a composition comprises: at least one auxotrophic microorganism including at least one temperature inducible repressor operably coupled to at least one heterologous genetic element encoding at least one therapeutic agent for at least one biological tissue, and including at least one genetic element inducible to initiate death of the at least one auxotrophic microorganism; and wherein the at least one composition includes at least one metabolite required by the at least one auxotrophic microorganism.

In an embodiment, a composition comprises: at least one auxotrophic microorganism including at least one pH inducible repressor operably coupled to at least one heterologous genetic element encoding at least one therapeutic agent for at least one biological tissue, and including at least one genetic element inducible to initiate death of the at least one auxotrophic microorganism; and wherein the at least one composition includes at least one metabolite required by the at least one auxotrophic microorganism.

In an embodiment, a method of administering at least one therapeutic agent to at least one biological tissue comprises: providing a composition to at least one biological tissue; wherein the composition includes at least one auxotrophic microorganism including at least one pH inducible heterologous genetic element encoding at least one therapeutic agent formulated for at least one biological tissue, and including at least one genetic element inducible to initiate death of the at least one auxotrophic microorganism; and the composition further including at least one metabolite required by the at least one auxotrophic microorganism.

In an embodiment, a composition comprises: at least one modified microorganism including at least one heterologous genetic element encoding at least one environmental medium treatment agent; and at least one genetic element inducible to initiate death of the at least one modified microorganism.

In an embodiment, a method of administering at least one environmental medium treatment agent to at least one environmental medium comprises: providing at least one composition to at least one environmental medium; wherein the at least one composition includes at least one modified microorganism including at least one heterologous genetic element encoding at least one environmental medium treatment agent, and at least one genetic element inducible to initiate death of the at least one modified microorganism.

In an embodiment, a delivery device comprises: a housing including at least one reservoir containing at least one composition, the at least one composition including at least one first constituent including at least one auxotrophic microorganism including at least one pH inducible promoter operably coupled to at least one heterologous genetic element encoding at least one therapeutic agent, and at least one genetic element inducible to initiate death of the at least one auxotrophic microorganism; and at least one second constituent including at least one metabolite required by the at least one auxotrophic microorganism; the reservoir configured to receive, retain, and dispense the at least one composition; and at least one constituent configured to administer the at least one composition to at least one biological tissue.

In an embodiment, a delivery device comprises: a housing including at least one reservoir containing at least one composition, the at least one composition including at least one modified microorganism including at least one heterologous genetic element encoding at least one environmental medium treatment agent, and at least one genetic element inducible to initiate death of the at least one modified microorganism, the reservoir configured to receive, retain, and dispense at least a portion of the at least one composition; and at least one component configured to administer the at least one composition to at least one environmental medium.

In an embodiment, a system comprises: at least one computing device; at least one delivery device configured to retain and dispense at least one composition to at least one biological tissue; and a recordable medium including one or more instructions that when executed on the computing device cause the computing device to regulate dispensing of at least a portion of the at least one composition, wherein the at least one composition includes at least one first constituent including at least one auxotrophic microorganism including at least one pH inducible promoter operably coupled to at least one heterologous genetic element encoding at least one therapeutic agent, and including at least one genetic element inducible to initiate death of the at least one auxotrophic microorganism; and at least one second constituent including at least one metabolite required by the at least one auxotrophic microorganism.

In an embodiment, a computer-implemented method comprises: one or more instructions for regulating dispensing at least one composition from at least one delivery device to at least one biological tissue, the at least one composition including at least one auxotrophic microorganism including at least one pH inducible heterologous genetic element encoding at least one therapeutic agent formulated for at least one biological tissue, and including at least one genetic element inducible to initiate death of the at least one auxotrophic microorganism; and at least one metabolite required by the at least one auxotrophic microorganism.

In an embodiment, a computer program product comprises: a recordable medium bearing one or more instructions for regulating dispensing of at least one delivery device, wherein the delivery device includes at least one composition, wherein the at least one composition includes at least one auxotrophic microorganism including at least one pH inducible heterologous genetic element encoding at least one therapeutic agent formulated for at least one biological tissue, and including at least one genetic element inducible to initiate death of the at least one auxotrophic microorganism; and at least one metabolite required by the at least one auxotrophic microorganism.

In an embodiment, a system comprises: at least one computing device; at least one delivery device configured to retain and dispense at least one composition to at least one environmental medium; and a recordable medium including one or more instructions that when executed on a computing device cause the computing device to regulate dispensing of at least a portion of the at least one composition, wherein the at least one composition includes at least one modified microorganism including at least one heterologous genetic element encoding at least one environmental medium treatment agent; and at least one genetic element inducible to initiate death of the at least one modified microorganism.

In an embodiment, a computer-implemented method comprises: one or more instructions for regulating dispensing of at least one composition from at least one delivery device to at least one environmental medium, the at least one composition including at least one modified microorganism including at least one heterologous genetic element encoding at least one environmental medium treatment agent; and at least one genetic element inducible to initiate death of the at least one modified microorganism.

In an embodiment, a computer program product comprises: a recordable medium bearing one or more instructions for regulating dispensing of at least one delivery device, wherein the delivery device includes at least one composition, wherein the at least one composition includes at least one modified microorganism including at least one heterologous genetic element encoding at least one environmental medium treatment agent; and at least one genetic element inducible to initiate death of the at least one modified microorganism.

In an embodiment, a computer-implemented method, system, or computer program product thereof, relates to making or administering the compositions described.

BRIEF DESCRIPTION OF THE FIGURES

FIG. 5 illustrates a partial view of a particular embodiment of a delivery device disclosed herein.

FIG. 6 illustrates a partial view of various embodiments of the device of FIG. 5.

FIG. 7 illustrates a partial view of various embodiments of the device of FIG. 5.

FIG. 8 illustrates a partial view of various embodiments of the device of FIG. 5.

FIG. 9 illustrates a partial view of various embodiments of the device of FIG. 5.

FIG. 10 illustrates a partial view of various embodiments of the device of FIG. 5.

FIG. 11 illustrates a partial view of various embodiments of the device of FIG. 5.

FIG. 12 illustrates a partial view of various embodiments of the device of FIG. 5.

FIG. 13 illustrates a partial view of various embodiments of the device of FIG. 5.

FIG. 14 illustrates a partial view of a particular embodiment of a delivery device disclosed herein.

FIG. 15 illustrates a partial view of various embodiments of the device of FIG. 14.

FIG. 16 illustrates a partial view of various embodiments of the device of FIG. 14.

FIG. 17 illustrates a partial view of various embodiments of the device of FIG. 14.

FIG. 18 illustrates a partial view of various embodiments of the device of FIG. 14.

FIG. 19 illustrates a partial view of various embodiments of the device of FIG. 14.

FIG. 20 illustrates a partial view of various embodiments of the device of FIG. 14.

FIG. 21 illustrates a partial view of a particular embodiment of a system disclosed herein.

FIG. 22 illustrates a partial view of various embodiments of the system of FIG. 21.

FIG. 23 illustrates a partial view of various embodiments of the system of FIG. 21.

FIG. 24 illustrates a partial view of various embodiments of the system of FIG. 21.

FIG. 25 illustrates a partial view of various embodiments of the system of FIG. 21.

FIG. 26 illustrates a partial view of various embodiments of the system of FIG. 21.

FIG. 27 illustrates a partial view of a particular embodiment of a computer-implemented method disclosed herein.

FIG. 28 illustrates a partial view of various embodiments of the computer-implemented method of FIG. 27.

FIG. 29 illustrates a partial view of various embodiments of the computer-implemented method of FIG. 27.

FIG. 30 illustrates a partial view of various embodiments of the computer-implemented method of FIG. 27.

FIG. 31 illustrates a partial view of various embodiments of the computer-implemented method of FIG. 27.

FIG. 32 illustrates a partial view of a particular embodiment of a computer program product disclosed herein.

FIG. 33 illustrates a partial view of various embodiments of the computer program product of FIG. 32.

FIG. 34 illustrates a partial view of a particular embodiment of a system disclosed herein.

FIG. 35 illustrates a partial view of various embodiments of the system of FIG. 33.

FIG. 36 illustrates a partial view of various embodiments of the system of FIG. 33.

FIG. 37 illustrates a partial view of various embodiments of the system of FIG. 33.

FIG. 38 illustrates a partial view of a particular embodiment of a computer-implemented method disclosed herein.

FIG. 39 illustrates a partial view of various embodiments of the computer-implemented method of FIG. 38.

FIG. 40 illustrates a partial view of various embodiments of the computer-implemented method of FIG. 38.

FIG. 41 illustrates a partial view of various embodiments of the computer-implemented method of FIG. 38.

FIG. 42 illustrates a partial view of a particular embodiment of a computer program product disclosed herein.

FIG. 43 illustrates a partial view of various embodiments of the computer program product of FIG. 42.

DETAILED DESCRIPTION

Figure 1:
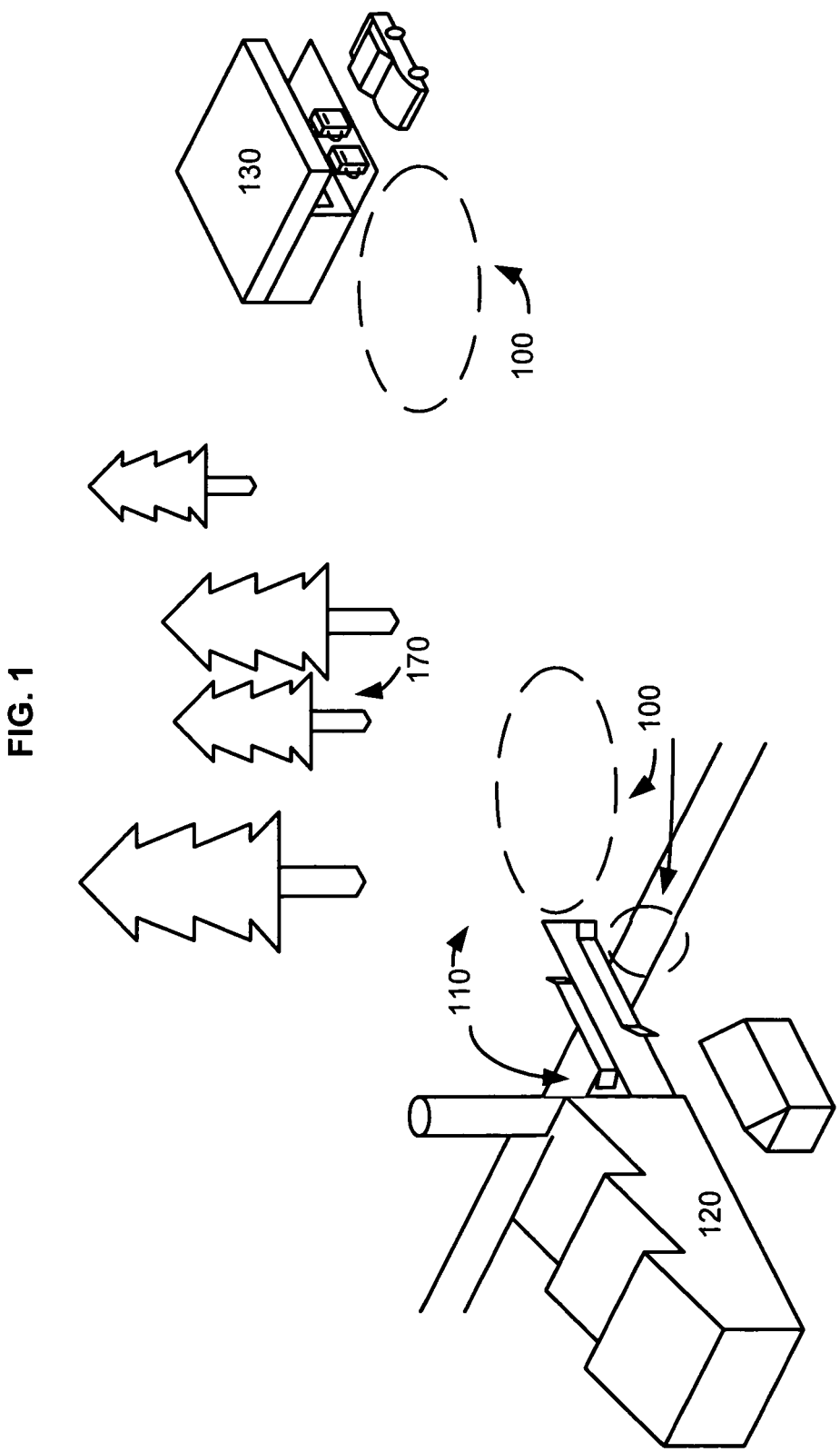
FIG. 1 illustrates a partial view of various embodiments disclosed herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

Modified Microorganisms

The compositions, methods, devices, and systems described herein relate to at least one modified microorganism (e.g., an auxotrophic microorganism) that is configured or modified to produce or deliver at least one agent (e.g., a therapeutic agent, environmental medium treatment agent, etc.) to at least one substrate (e.g., biological tissue, environmental medium, etc.).

For example, in an embodiment, a composition comprises at least one auxotrophic microorganism including at least one pH inducible promoter operably coupled to at least one heterologous genetic element encoding at least one therapeutic agent for at least one biological tissue, and including at least one genetic element inducible to initiate death of the at least one auxotrophic microorganism; and wherein the at least one composition includes at least one metabolite required by the at least one auxotrophic microorganism. In an embodiment, a composition comprises at least one auxotrophic microorganism including at least one temperature inducible promoter operably coupled to at least one heterologous genetic element encoding at least one therapeutic agent for at least one biological tissue, and including at least one genetic element inducible to initiate death of the at least one auxotrophic microorganism; and wherein the at least one composition includes at least one metabolite required by the at least one auxotrophic microorganism.

In an embodiment, a composition comprises at least one auxotrophic microorganism including at least one temperature inducible repressor operably coupled to at least one heterologous genetic element encoding at least one therapeutic agent for at least one biological tissue, and including at least one genetic element inducible to initiate death of the at least one auxotrophic microorganism; and wherein the at least one composition includes at least one metabolite required by the at least one auxotrophic microorganism.

In an embodiment, a composition comprises at least one auxotrophic microorganism including at least one pH inducible repressor operably coupled to at least one heterologous genetic element encoding at least one therapeutic agent for at least one biological tissue, and including at least one genetic element inducible to initiate death of the at least one auxotrophic microorganism; and wherein the at least one composition includes at least one metabolite required by the at least one auxotrophic microorganism.

In an embodiment, a composition comprises at least one modified microorganism including at least one heterologous genetic element encoding at least one environmental medium treatment agent; and at least one genetic element inducible to initiate death of the at least one modified microorganism.

In an embodiment, the modified microorganism includes at least one genetic element (e.g., heterologous genetic element) encoding the at least one agent. In an embodiment, the composition further comprises at least one metabolite utilizable or required by the at least one modified microorganism. In an embodiment, the at least one modified microorganism includes at least one inducible genetic element configured to initiate death of the modified microorganism. In an embodiment, the metabolite includes the at least one therapeutic agent or environmental treatment agent produced by the modified microorganism. In an embodiment, the metabolite is provided by the at least one biological tissue or environmental medium.

In an embodiment, a modified microorganism includes a microorganism that has been chemically, physically, or genetically modified from a naturally occurring microorganism, or a microorganism that has been artificially synthesized. In an embodiment, the modified microorganism includes an auxotrophic microorganism. For example, in an embodiment, an auxotrophic microorganism includes at least one modification that renders it dependent on at least one metabolite for maintenance of physiological processes (e.g., metabolism, reproduction, sporulation, etc.). In an embodiment, the modified microorganism is unable to manufacture the metabolite itself, and instead must receive the metabolite from the environment. In particular instances, the metabolite acts as at least one of a repressor or inducer of the at least one genetic element inducible to initiate death of the at least one modified microorganism. Examples of particular metabolites are described herein, and include but are not limited to, energy sources or nutrients for metabolic pathways.

In an embodiment, the metabolite is utilizable but not required by the modified microorganism. For example, in an embodiment an auxotrophic microorganism may require one metabolite but also be able to utilize other metabolites (whether or not such metabolites can replace the required metabolite).

In an embodiment, the at least one metabolite includes at least one promoter operably coupled to at least one heterologous genetic element encoding the at least one therapeutic agent or at least one environmental medium treatment agent. In an embodiment, the at least one metabolite includes a time-release formulation. In an embodiment, the wherein the metabolite is formulated for pH-dependent release or activation.

In an embodiment, the pH level of the release or activation of the at least one pH dependent metabolite is different than the pH level of the pH inducible promoter operably coupled to the at least one heterologous genetic element encoding at least one therapeutic agent or at least one environmental medium treatment agent.

In an embodiment, the administered microorganism remains relatively localized. For example, by utilizing a microorganism including at least one genetic element that allows for controlled growth, the microorganism can be directed toward or away from a particular location. In one example, by allowing selective growth of the microorganism, or selective agent production (e.g., lactic acid suppressor gene), the microorganism can be directed or controlled. In another example, the modified microorganism includes a recombinant microorganism with a mutation that renders the microorganism dependent on an external factor for survival (e.g., thymidylate synthase gene). In another example, the modified microorganism contains an essential gene and a control sequence that regulates expression of the lethal gene such that an essential gene is expressed in a permissive environment and not expressed in a nonpermissive environment. In another example, the modified microorganism contains a lethal gene and a control sequence that regulates expression such that the lethal gene is expressed in a nonpermissive environment, and not expressed when in a permissive environment. See, for example, U.S. Patent Application Publication No. 20080253990, and U.S. Patent Application Publication No. 20080254014, each of which is incorporated herein by reference.

In an embodiment, the microorganism includes at least one genetic element inducible to initiate death in the at least one microorganism. In this manner, the microorganism includes suicide genetic elements that are inducible to initiate death in the microorganism upon encountering at least one inducer that regulates the genetic elements. In an embodiment, the genetic elements inducible to initiate death in the microorganism include at least one of an inducible promoter, inducible enhancer, or inducible repressor, any of which is operably coupled to the genetic element that encodes the particular suicide gene or other death-initiating gene. In an embodiment, the genetic elements that regulate the induction of death of the microorganism are incorporated as part of the microoganisms' own chromosomal or genetic constitution. In an embodiment, the genetic elements that regulate the induction of death of the microorganism are included as part of a vector (e.g., plasmid, cosmid, etc.). See, for example, U.S. Patent Application No. 20050276788, which is incorporated herein by reference.

In an embodiment, at least one of the promoter, enhancer, or repressor operably coupled to the heterologous genetic element encoding the at least one therapeutic agent or the at least one environmental medium treatment agent is an epigenetic element.

In an embodiment, at least one of the promoter, enhancer, or repressor operably coupled to the at least one heterologous genetic element encoding the at least one therapeutic agent or the at least one environmental medium treatment agent is an epigenetic element.

Many standard lethal genes or lethal gene systems are known. For example, in an embodiment, a conditional lethal system for eukaryotic cells (e.g., fungal cells such as yeast, or other eukaryotic cells) is utilized by providing intracellular production of the *Serratia marcescens* nuclease in the cell, which destroys the genetic material in the cell. See, for example, Balan and Schenberg, Yeast, vol. 22, pp. 203-212 (2005), which is incorporated herein by reference. As reported, under normal conditions, the nuclease, encoded by the nucA gene, is secreted into the extracellular medium. Cloning it without the signal sequence, however, results in killing the yeast cell upon glucose depletion from the medium. Id. The conditional lethal system also disfavors horizontal gene transfer from recombinant yeast cells to other microorganisms found in the environment. Id.

In an embodiment, a lac-hok cassette is utilized for inducing death, wherein the hok gene from plasmid R1 belongs to a family of genes encoding small polypeptides (about 50 amino acids) which, when overexpressed, collapse the membrane potential and lead to cell death. See, for example, Contreras, et al., App. Env. Microbiol. vol. 57, no. 5, pp. 1504-1508 (1991), which is incorporated herein by reference. In an embodiment, a gef system, a chromosomally encoded *E. coli* gene highly homologous to hok, is utilized for inducing death in the modified microorganism. For example, the modified microorganism survives only in the presence of effectors of the meta-cleavage pathway encoded by the TOL plasmid of *P. putida*. Id. For example, in an embodiment, microorganisms modified to degrade substituted benzoates utilize a LacI protein (Lac repressor) expressed from a Pm::lacI fusion represses transcription from a Ptac::gef cassette in the presence of XylS effectors (coding for the regulator necessary to activate transcription from Pm, in the presence of an effector such as 3-methylbenzoate, in this example), whereas in the absence of XylS effectors, expression of the gef gene is no longer repressed, leading to cell killing. Id. Substitution of XylS for another protein expands the range of response. Id. Thus, in an embodiment, a similar construct is developed for regulation of production of a particular therapeutic or environmental medium treatment agent in a modified microorganism, as described herein.

In an embodiment, the at least one modified microorganism includes at least one genetic element inducible to initiate death of the at least one microorganism. In an embodiment, the inducible genetic element includes at least one secretory signal sequence. Various mechanisms can be employed to initiate death of the microorganism. For example, the genetic element inducible to initiate death can include a genetic element inducible to initiate at least one of programmed cell death, to initiate autophagocytosis of the at least one microorganism, to lyse the at least one microorganism, or by other means.

In an embodiment, the at least one genetic element inducible to initiate death of the at least one modified microorganism includes at least one genetic element inducible to initiate programmed cell death. In an embodiment, the genetic element inducible to initiate death of the at least one modified microorganism includes at least one of programmed cell death 1 gene (PDCD1), programmed cell death 2 gene (PDCD2), programmed cell death 3 gene (PDCD3), programmed cell death 4 gene (PDCD4), programmed cell death 5 gene (PDCD5), programmed cell death 6 gene (PDCD6), programmed cell death 7 gene (PDCD7), programmed cell death 8 gene (PDCD8), programmed cell death 9 gene (PDCD9), programmed cell death 10 gene (PDCD10), programmed cell death 11 gene (PDCD11), programmed cell death 12 gene (PDCD12), caspase gene, rel gene, hok gene, sok gene, diaminopimelate gene, nuclease gene, methylase gene, DNA ligase gene, DNA gyrase gene, toxin-antitoxin module, relF gene, triclosan, lysine, or lysine-holin. In an embodiment, the toxin-antitoxin module includes at least one of masEF, chpBIK, relBE, yefM-yoeB, dinJ-yafl, or ecnA-ecnB. In an embodiment, the at least one inducible genetic element configured to lyse the at least one auxotrophic microorganism includes at least one of a nuclease gene, or lysis gene E.

In an embodiment, the at least one inducible genetic element configured to initiate death of the modified microorganism includes at least one toxin-antitoxin. Toxin-antitoxin modules are generally gene pairs specifying for a toxin and its antitoxin, and are found on the chromosomes of many bacteria. For example, in *E. coli*, mazF encodes a stable toxin (MazF), and mazE encodes a labile antitoxin (mazE) which prevents the lethal effect of MazF. See, for example, J. Bacteriol., vol. 186, no. 24, pp. 8295-8300, (2004), which is incorporated herein by reference. As published, the quorum sensing peptide, Extracellular Death Factor, is a signal molecule required for mazEF-mediated cell death. Id.

In an embodiment, the at least one genetic element inducible to initiate death of the modified microorganism includes at least one genetic element inducible to interfere with the utilization of the at least one metabolite (e.g., by encoding a peptide or protein that interferes with the microorganism's metabolism, etc.).

Figure 3:
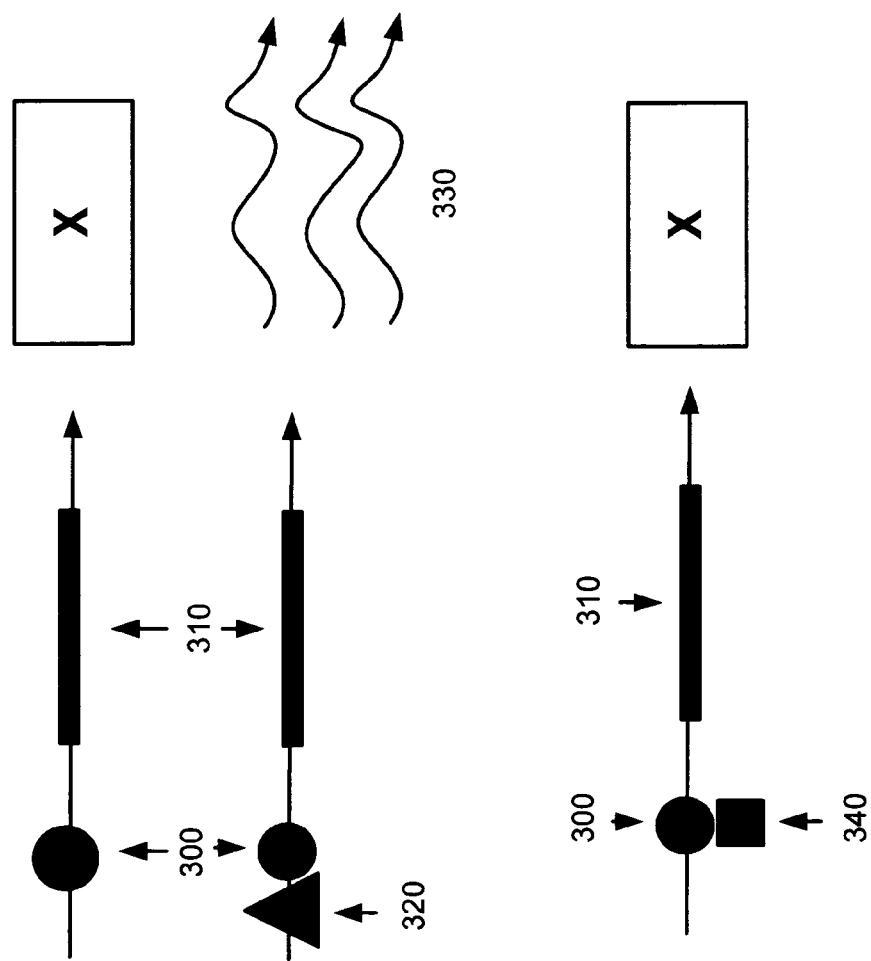
FIG. 3 illustrates a partial view of particular genetic elements utilized in various embodiments disclosed herein.

In an embodiment, the at least one inducible genetic element configured to initiate death of the modified microorganism includes at least one of extracellular death factor, mazF, or mazEF. As illustrated in FIG. 3, an example of an inducible genetic element, including an inducible promoter 300 is capable of regulating expression of at least one gene 310. In the absence of an inducer 320, the gene 310 is not transcribed (as indicated by the "X"). However, in the presence of the inducer 320, the promoter 300 directs transcription of the gene 310, resulting in production of at least one transcript 330. Likewise, in the presence of a repressor 340, the promoter 300 does not support gene transcription of the gene 310 (as indicated by the "X"). In an embodiment, the at least one genetic element inducible to initiate death of the at least one modified microorganism includes at least one genetic element inducible to initiate autophagocytosis of the at least one modified microorganism.

As described herein, in an embodiment the at least one composition includes at least one metabolite that is required by the at least one modified microorganism. In an embodiment, the modified microorganism has a strict requirement for at least one metabolite that is not present or is present at low concentrations in the external environment (e.g., auxotrophic). For example, the at least one metabolite includes, but is not limited to, at least one of an organic or inorganic small molecule, nucleic acid, amino acid, peptide, polypeptide, protein, glycopeptide, glycoprotein, glycolipid, lipopolysaccharide, peptidoglycan, proteoglycan, lipid, metalloprotein, metal, liposome, carbohydrate, or radiation. In an embodiment, the at least one metabolite includes at least one of arabinose, lactose, maltose, sucrose, glucose, xylose, galactose, rhamnose, fructose, melibiose, starch, inunlin, lipopolysaccharide, arsenic, cadmium, hydrocarbon, chromium, ultra-violet radiation, infrared radiation, electromagnetic radiation, visible radiation, antibiotic, oxygen, carbon dioxide, nitrogen, xylan, or nisin. Other non-limiting examples of metabolites include at least one of L-arabinose, allolactose, D-glucose, D-xylose, D-galactose, ampicillin, tetracycline, penicillin, pristinamycin, retinoic acid, or interferon. In an embodiment, the at least one metabolite includes the at least one therapeutic or environmental medium treatment agent, or at least one component thereof. In certain instances, the at least one metabolite is provided or produced by the at least one biological tissue or environmental medium. In an embodiment, the at least one metabolite utilizable by the modified microorganism is the same as at least one inducer capable of inducing at least one inducible genetic element of the modified microorganism.

In an embodiment, the at least one metabolite includes at least one repressor of the at least one inducible genetic element configured to initiate death of the at least one auxotrophic or modified microorganism. In an embodiment, the at least one inducible genetic element configured to initiate death of the at least one auxotrophic or modified microorganism includes at least one inducible promoter. In an embodiment, the at least one inducible genetic element configured to initiate death of the at least one auxotrophic or modified microorganism includes at least one regulatory sequence. In an embodiment, the at least one regulatory sequence includes at least one terminator fragment, enhancer sequence, or marker sequence.

In an embodiment, the at least one metabolite is provided by at least one modified biological cell. The modified biological cell can include, for example, at least one of bacteria, protozoa, rotifers, algae, archaeon, or fungi. In an embodiment, the modified biological cell includes at least one prokaryote cell or eukaryote cell. In an embodiment, the modified biological cell includes at least one modified microorganism (e.g., an auxotrophic microorganism). In an embodiment, the modified biological cell includes at least one blood cell, muscle cell, nerve cell, fibroblast, adipose cell, stem cell, pluripotent cell, epithelial cell, skin cell, neoplastic cell, or other biological tissue or organ cell. In an embodiment, the modified biological cell includes at least one autologous cell or modified autologous cell. In an embodiment, the modified biological cell is at least part of at least one cell mass. In an embodiment, the at least one cell mass includes at least one tumor, scar, pore, pit, eschar, granuloma, keloid, artheromatous plaque, abscess, pustule, scaling (e.g., psoriasis or eczema), infected tissue, hair follicle, necrotic tissue, stratum corneum, wrinkle, wound, tumor, skin structure, nevus, cyst, lesion, callus, neoplastic tissue, gangrenous tissue, fetal tissue, placental tissue, or cellular deposit.

In an embodiment, the modified biological cell is positioned for at least one of a commensal or cooperative relationship with the at least one modified microorganism. In an embodiment, the modified biological cell is positioned for obligatory cooperation with the at least one modified microorganism.

Developing a modified biological cell that is formulated to coexist in a cooperative relationship with another cell is conducted using routine laboratory procedures. For example, populations of *Saccharomyces cerevisiae* have been modified to create obligatory cooperation by mutating each strain in such a manner as to render each strain nutritionally deficient without the other. See, for example, Shou, et al. PNAS, vol. 104, no. 6, pp. 1877-1882 (2007), which is incorporated herein by reference. For example, a first *S. cerevisiae* strain was modified in order to require adenine to grow and overproduce lysine, while a second *S. cerevisiae* strain was modified to require lysine to grow and overproduce adenine. Id. These modified, nonmating yeast strains compose a synthetic obligatory cooperative system, termed COSMO (cooperation that is synthetic and mutually obligatory) by providing an essential metabolite to the other strain. Id. As published, persistent cooperation can be established with the modified yeast strains, and is mathematically and experimentally shown to be viable over a wide range of initial conditions, with oscillating population ratio settling to a value predicted by nutrient supply and consumption. Id.

Furthermore, even in the absence of explicitly engineered mechanisms to stabilize cooperation, the system can consistently develop increased ability to survive reductions in population density. Id. For example, members of a microorganism consortium can exert both positive and negative control over one another's activities by exchanging metabolic intermediates that either assist or compromise the growth of their neighbors. In one example, engineered acyl-HSL communication has been used in biological "circuits" that coordinate population-wide behaviors ranging from population density dependent fluorescence, cell suicide, and invasion of cancer cells, to pattern formation. Id. In one example, upon induction of the biological circuit that encodes the communication and the programmed cellular response, one population ("predator") dies out in the absence of the other ("prey") population. Communication between the two populations directs the "prey" to rescue the predator, but once the "predator" recovers to a sufficiently high density, it begins to kill the "prey". Id.

In an embodiment, a cooperative relationship includes, but is not limited to biofilm formation, colonization, virulence, proliferation, communication, and other activities. See, for example, Brenner, et al., Trends Biotech. vol. 26, no. 9, pp. 483-489 (2008), which is incorporated herein by reference. For example, the at least one modified microorganism can participate in at least one microbial consensus consortium for cross-talk and cell-cell signaling. See, for example, Brenner, et al., PNAS, vol. 104, no. 44, pp. 17300-17304 (2007), which is incorporated herein by reference.

Published studies describe synthetic ecosystems of at least one microbial population capable of communicating bi-directionally through quorum sensing and regulating gene expression and survival of other population members, by way of engineered gene circuits. See, for example, Balagadde, et al., Mol. Sys. Biol. vol. 4, no. 187, pp. 1-8 (2008), which is incorporated herein by reference. As discussed herein, in an embodiment, the "predator cells" kill the "prey" by inducing expression of a killer protein in the "prey," while the "prey" rescues the "predators" by eliciting expression of an antidote protein in the "predator". Thus, extinction, coexistence and oscillatory dynamics of the "predator" and "prey" populations are possible depending on the operating conditions, which can be determined mathematically. Id. In an embodiment, the "predator" includes the at least one modified biological cell, and the "prey" includes the at least one modified microorganism. In an embodiment, the "predator" includes the at least one modified microorganism, and the "prey" includes the at least one modified biological cell.

In an embodiment, the at least one modified microorganism is in a syntrophic relationship with at least one other modified microorganism. See, for example, Marx, Science vol. 324, pp. 1150-1151 (2009), which is incorporated herein by reference. For example, one modified microorganism may convert the primary resource to an intermediate that can be used by another modified microorganism. In an embodiment, one modified microorganism provides motility for another modified microorganism, which may in turn provide a nutrient source. Id.

In an embodiment, the modified microorganism includes at least one nucleic acid construct, including a heterologous genetic element that includes at least one artificial operon. In an embodiment, the at least one artificial operon encodes at least one polycistronic mRNA transcript.

In an embodiment, the modified microorganism includes at least one heterologous genetic element encoding at least one agent. In an embodiment, the heterologous genetic element includes at least one of an inducible promoter, enhancer, or repressor operably coupled to the heterologous gene. In an embodiment, the at least one inducible promoter includes at least one neutral, base or acid inducible promoter. In an embodiment, the genetic element inducible to initiate death of the at least one modified microorganism includes at least one of an inducible promoter, enhancer, or repressor operably coupled to the suicide or other death-inducing gene. In an embodiment, at least one inducer for one or more various inducible promoters, enhancers, or repressors is located in the biological tissue or environmental medium to which the composition is administered or is to be administered.

In an embodiment, at least one of the inducible promoter, inducible enhancer, or inducible repressor includes at least one pH or temperature inducible promoter, enhancer, or repressor. In an embodiment, the inducible promoter, enhancer, or repressor includes an acid inducible promoter, enhancer, or repressor. In an embodiment, the inducible promoter, enhancer, or repressor includes a base inducible promoter, enhancer, or repressor. In an embodiment, the inducible promoter, enhancer, or repressor includes a neutral inducible promoter, enhancer, or repressor.

Examples of acid inducible promoters include, but are not limited to HVA1 promoter (plant cells), P170, P1, or P3 (*Lactococcus*), baiA1, baiA3 (Eubacteria), lipF promoter (Mycobacteria), $F_1F_0$-ATPase promoter (*Lactobacillus, Streptococcus*, or *Enterococcus*), gadC, gad D (*Lactococcus, Shignella*), glutamate decarboxylase promoter (Mycobacteria, *Clostridium, Listeria, Lactobacillus*), or similar operons. See, for example, Cotter and Hill, Microbiol. and Mol. Biol. Rev. vol. 67, no. 3, pp. 429-453 (2003); Hagenbeek, et al., Plant Phys., vol. 123, pp. 1553-1560 (2000); Madsen, et al., Abstract, Mol. Microbiol. vol. 56, no. 3, pp. 735-746 (2005); U.S. Pat. No. 6,242,194; Richter, et al., Abstract, Gene, vol. 395, no. 1-2, pp. 22-28 (2007), Mallonee, et al., J. Bacteriol., vol. 172, no. 12, pp. 7011-7019 (1990); each of which is incorporated herein by reference. Examples of base inducible promoters include, but are not limited to, alkaline phosphatase promoters.

In an embodiment, the acid inducible promoter, enhancer, or repressor is inducible at a pH of approximately 0.0, approximately 0.5, approximately 1.0, approximately 1.5, approximately 2.0, approximately 2.5, approximately 3.0, approximately 3.5, approximately 4.0, approximately 4.5, approximately 5.0, approximately 5.5, approximately 6.0, approximately 6.5, approximately 6.6, approximately 6.7, approximately 6.8, approximately 6.9, or any value therebetween or less.

In an embodiment, the base inducible promoter, enhancer, or repressor is inducible at a pH of approximately 7.1, approximately 7.5, approximately 8.0, approximately 8.5, approximately 9.0, approximately 9.5, approximately 10.0, approximately 10.5, approximately 11.0, approximately 11.5, approximately 12.0, approximately 12.5, approximately 13.0, approximately 13.5, approximately 14.0, or any value therebetween or greater.

In an embodiment, the neutral inducible promoter, enhancer, or repressor is inducible at a pH of approximately 7.0.

The pH level of a particular biological tissue can affect the inducibility of the pH inducible promoter. For example, the gastric pH of humans is between 1.5 (fasting state), and 3.0-5.0 (following feeding). Id. Likewise, human urine has a pH of approximately 6.0, human skin has a pH of approximately 5.5, human ear canal has a pH of approximately 4.5, while blood and cerebrospinal fluid tend to have a pH of approximately 7.3-7.4. See, for example, Boron, et al., Medical Physiology: A Cellular and Molecular Approach. Elsevier/Saunders. (2004), ISBN 1-4160-2328-3, which is incorporated herein by reference. Furthermore, dental caries and tooth demineralization is initiated at a pH of approximately 5.2. Cotter and Hill, Ibid. Thus, a composition that is activated at various pH levels is useful for particular embodiments. In an embodiment, the pH inducible promoter is induced at a particular pH (e.g., chewing gum containing the composition described herein which is inducible at low pH in the mouth). The pH level of plant leaves is approximately 4.2. See, for example, Sargent and Blackman, Abstract, J. Exp. Botany, vol. 21, no. 1, pp. 219-227 (2005), which is incorporated herein by reference. In an embodiment, the at least one inducible promoter or inducible enhancer facilitates transcription of the genetic element encoding the environmental medium treatment agent, or therapeutic agent, or the genetic element inducible to initiate death in the modified microorganism.

As described herein for various inducible genetic elements, the inducible genetic elements can include at least one inducible promoter, inducible repressor, or inducible enhancer. Examples of inducers include, but are not limited to, at least one of radiation, temperature change, alcohol, antibiotic, steroid, metal, salicylic acid, ethylene, benzothiadiazole, or other compound. In an embodiment, the at least one inducer includes at least one of arabinose, lactose, maltose, sucrose, glucose, xylose, galactose, rhamnose, fructose, melibiose, starch, inunlin, lipopolysaccharide, arsenic, cadmium, chromium, temperature, light, antibiotic, oxygen level, xylan, nisin, L-arabinose, allolactose, D-glucose, D-xylose, D-galactose, ampicillin, tetracycline, penicillin, pristinamycin, retinoic acid, or interferon. Other examples of inducers include, but are not limited to, at least a portion of one of an organic or inorganic small molecule, clathrate or caged compound, protocell, coacervate, microsphere, Janus particle, proteinoid, laminate, helical rod, liposome, macroscopic tube, niosome, sphingosome, vesicular tube, vesicle, small unilamellar vesicle, large unilamellar vesicle, large multilamellar vesicle, multivesicular vesicle, lipid layer, lipid bilayer, micelle, organelle, nucleic acid, peptide, polypeptide, protein, glycopeptide, glycolipid, lipoprotein, lipopolysaccharide, sphingolipid, glycosphingolipid, glycoprotein, peptidoglycan, lipid, carbohydrate, metalloprotein, proteoglycan, chromosome, nucleus, acid, buffer, protic solvent, aprotic solvent, nitric oxide, vitamin, mineral, nitrous oxide, nitric oxide synthase, amino acid, micelle, polymer, copolymer, monomer, prepolymer, cell receptor, adhesion molecule, cytokine, chemokine, immunoglobulin, antibody, antigen, extracellular matrix, cell ligand, zwitterionic material, cationic material, oligonucleotide, nanotube, piloxymer, transfersome, gas, element, contaminant, radioactive particle, radiation, hormone, virus, quantum dot, temperature change, thermal energy, or contrast agent. See, for example, Theys, et al., Abstract, Curr. Gene Ther. vol. 3, no. 3 pp. 207-221 (2003), which is incorporated herein by reference. In an embodiment, the at least one inducer is produced by at least one microorganism.

In an embodiment, the at least one inducible genetic element is temperature inducible. For example, various heat shock protein promoters have been isolated from microorganisms, animal and plant cells (including maize and soybeans), and other temperature inducible promoters have been isolated from various organisms and microorganisms. Some non-limiting examples of promoters induced by a change in temperature include hsp70 (e.g., animal cells, maize), Gmhsp17.5-E (e.g., soybeans), Gmhsp17.6-L, HS6871 (e.g., soybeans), HSP18.2 (*Arabidopsis*), HSP18.1 (*Arabidopsis*), Hsp70B, P2 (*Bacillus*), P7 (*Bacillus*), PhS (*E. coli*), *Tetrahymena therophila* promoter (protozoan), *Hansenula polymorpha* promoter (yeast), *Schizosaccharomyces pombe* promoters (yeast), or $P_L$ (lambda phage). See, for example, Taylor, et al, Cell, Abstract, vol. 38, no. 2, pp. 371-381 (1984); U.S. Pat. No. 6,852,511, Wang, et al., Biochem. and Biophys. Res. Commun. Abstract, vol. 358, no. 4, pp. 1148-1153 (2007), U.S. Pat. No. 7,462,708, each of which is incorporated herein by reference.

In an embodiment, the at least one modified microorganism includes at least one of a prokaryote or a eukaryote. In an embodiment, the at least one modified microorganism includes at least one of bacteria, protozoa, rotifers, algae, archaeon, or fungi. In an embodiment, the at least one modified microorganism includes at least one of a non-pathogenic strain, transgenic microorganism, magnetotactic microorganism, anaerobic or aerobic microorganism, food grade strain, obligate microorganism, attenuated microorganism strain, facultative anaerobe, non-invasive strain, probiotic, colonizing microorganism, element-modifying microorganism, or photosynthetic microorganism. In an embodiment, the at least one element-modifying microorganism includes at least one of a nitrogen-fixing microorganism, nitrifying microorganism, denitrifying microorganism, hydrocarbon-utilizing microorganism, dechlorinating microorganism, or a sulfate-reducing microorganism.

In an embodiment, the at least one auxotrophic or modified microorganism includes at least one of *Bifidobacterium, Lactococcus, Lactobacillus, Salmonella, Clostridium, Escherichia, Listeria, Streptococcus, Staphlococcus, Bacillus, Marinobacter, Micrococcus, Dietzia, Oceanobacillus, Citriococcus, Georgenia, Microbacterium, Stappia, Isoptericola, Cellulomonas, Rhizobia, Frankia, Klebsiella, Nocardioform Actinomycetes, Cytophagacia, Corynebacterium, Vibrionacia, Cyanobacteria, Pseudomonas, Rhastonia, Sphaerotilus, Shewanella, Wolbachia,* or *Azotobacter, Azospirillum*. In an embodiment, the at least one auxotrophic microorganism includes at least one of *Saccharomyces, Candida, Brettanomyces, Zygosaccharomyces, Yarrowia, Schizosaccharomyces, Torulaspora, Neotyphodium,* or *Cryptococcus*.

Some non-limiting examples of microorganisms that can be modified according to various embodiments described herein include: *Lactococcus garvieae, Lactococcus lactis, Lactococcus lactis* subsp. *cremoris, Lactococcus lactis* subsp. *hordniae, Lactococcus lactis, Lactococcus lactis* subsp. *Lactis, Lactococcus piscium, Lactococcus plantarum, Lactococcus raffinolactis, Lactobacillus acetotolerans, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarius, Lactobacillus aviarius* subsp. *araffinosus, Lactobacillus aviarius* subsp. *aviarius, Lactobacillus bavaricus, Lactobacillus bifermentans, Lactobacillus brevis, Lactobacillus buchneri, Lactobacillus bulgaricus, Lactobacillus carnis, Lactobacillus casei, Lactobacillus casei* subsp. *alactosus, Lactobacillus casei* subsp. *casei, Lactobacillus casei* subsp. *pseudoplantarum, Lactobacillus casei* subsp. *rhamnosus, Lactobacillus casei* subsp. *tolerans, Lactobacillus catenaformis, Lactobacillus cellobiosus, Lactobacillus collinoides, Lactobacillus confusus, Lactobacillus coryniformis, Lactobacillus coryniformis* subsp. *coryniformis, Lactobacillus coryniformis* subsp. *torquens, Lactobacillus crispatus, Lactobacillus curvatus, Lactobacillus curvatus* subsp. *curvatus, Lactobacillus curvatus* subsp. *melibiosus, Lactobacillus delbrueckii, Lactobacillus delbrueckii* subsp. *bulgaricus, Lactobacillus delbrueckii* subsp. *delbrueckii, Lactobacillus delbrueckii* subsp. *lactis, Lactobacillus divergens, Lactobacillus farciminis, Lactobacillus fermentum, Lactobacillus fornicalis, Lactobacillus fructivorans, Lactobacillus fructosus, Lactobacillus gallinarum, Lactobacillus gasseri, Lactobacillus graminis, Lactobacillus halotolerans, Lactobacillus hamsteri, Lactobacillus helveticus, Lactobacillus heterohiochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefiranofaciens, Lactobacillus kefirgranum, Lactobacillus kunkeei, Lactobacillus lactis, Lactobacillus leichmannii, Lactobacillus lindneri, Lactobacillus malefermentans, Lactobacillus mali, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus paracasei* subsp. *paracasei, Lactobacillus paracasei* subsp. *tolerans, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus reuteri, Lactobacillus rhamnosus, Lactobacillus rimae, Lactobacillus rogosae, Lactobacillus ruminis, Lactobacillus sakei, Lactobacillus sakei* subsp. *carnosus, Lactobacillus sakei* subsp. *sakei, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis, Lactobacillus yamanashiensis* subsp. *mall, Lactobacillus yamanashiensis* subsp. *Yamanashiensis, Lactobacillus zeae, Clostridium novyi, Clostridium sordellii, Bifidobacterium longum, Escherichia coli, Salmonella typhimurium, Salmonella paratyphi, Salmonella pneumoniae, Salmonella enterica, Streptococcus pneumoniae, Streptococcus pyogenes, Streptococcus* group B, *Streptococcus mutans, Streptococcus sobrinus, Streptococcus equi, Staphylococcus* ssp., *Erysipelothrix rhusiopathiae, Bacillus anthracis, Listeria monocytogenes, Mycobactterium leprae, Mycobactterium tuberculosis, Clostridium tetani, Clostridium botulinum, Clostridium difficile, Clostridium perfringens, Corynebacterium diphtheriae, Mycoplasma* ssp., *Rhodococcus, Nocardia, Gordona, Jensenia, Shewanella, Shewandella oneidensis, Dehalococcoides, Burkholderia zenovorans, Comamonas, Cupriavidus, Sphingomonas, Acidovorax, Desulfovibrio, Anabaena cylindrica, Plectonema, Nostoc commune, Rhodobacter sphaeroides, Rhodopseudomonas palustris,* or *Rhodobacter capsulatus, Escherichia coli* Nissle 1917, *Salmonella typhimurium* 14028, *Salmonella typhimurium* SL1344, *Salmonella typhi, Salmonella abortus-ovi, Salmonella abortus-equi, Salmonella* Dublin, *Salmonella gallinarum, Salmonella pullorum, Shigella fexneri, Shigella sonnei, Haemophilus influenzae, Bordetella pertussis, Nisseria meningitides, Nisseria gonorrohia, Pasteuralla multocida, Yersinia pestis, Escherichia coli* 4608-58, *Salmonella flexneri* 2a SC602, *Escherichia coli* CFT073, *Escherichia coli* Top10, *Escherichia coli* MC1000, *Escherichia coli* NF1815, *Escherichia coli* NF1830, *Escherichia coli* HB101, *Escherichia coli* BD3364, *Escherichia coli* BD3364, *Escherichia coli* HfrC, *Escherichia coli* BD3342, *Escherichia coli* BD3346, *Escherichia coli* XAC, *Escherichia coli* BD71, *Escherichia coli* BD76, *Escherichia coli* S17.1, *Lactococcus lactis* MG1363, *Lactococcus lactis*-Thy12, *Clostridium novyi*-NT, *Lactobacillus plantarum* NCIMB8826, *Lactobacillus plantarum* NCIMB8826Intl, *Lactobacillus fermentum* KLD, *Lactobacillus plantarum* MD007, *Lactobacillus plantarum* MD007Int6, *Lactococcus lactis* NZ3900, MC-1 magnetotactic bacteria, *Lactococcus lactis* PH3960, *Streptococcus gordonii, Lactobacillus zeae, Streptococcus mutans, Bacteroides ovatus, Bacteroides fragilis, Prevotella, Saccharomyces boulardii, Firmicutes, Gammaproteobacteria, Prevotellaceae, Archaea, Listeria innocua, Staphylococcus xylosus, Staphylococcus carnosus, Listeria monocytogenes, Klebsiella pneumoniae, Azotobacter vinlandii, Anabaena cylindrica, Plectonema, Nostoc commune, Rhodobacter sphaeroides, Rhodopseudomonas palustris, Rhodobacter capsulatus, Clavibacter, Alcaligenes, Sphingobacterium, Phyllobacterium, Aeromonas, Stenotro-*

*phomonas, Acidovorax, Comamonas, Desulfovibrio, Stentrophomonas, Serratia, Pseudomonas aeruginosa, Stentrophomonas maltophilia, Serratia marsescens, Variovorax, Chryseobacterium, Comamonas, Acidovorax, Stenotrophomonas, Sphingobacterium, Xanthomonas, Frateuria, Zoogloea, Alcaligenes, Flavobacterium, Derxia, Lampropedia, Brucella, Xanthobacter, Thermus, Thermomicrobium, Halomonas, Alteromonas, Serpens, Janthinobacterium, Bordetella, Paracoccus, Beijerinckia, Francisella,* Eubacteria, *Actinomycetes, Nocardia, Rhodococcus, Gordona, Nocardioides, Saccharopolyspora, Micropolyspora, Promicromonospora, Intrasporangium, Pseudonocardia, Oerskovia, Stomatococcus, Planococcus, Aerococcus, Peptococcus, Peptostreptococcus, Coprococcus, Gemella, Pediococcus, Leuconostoc, Ruminococcus, Sarcina, Aeromonas, Photobacterium, Vibrio, Plesiomonas, Zymomonas, Chromobacterium, Cardiobacterium, Calymmatobacterium, Streptobacillus, Eikenella, Gardnerella, Phyllobacterium, Rhizobium, Bradyrhizobium, Agrobacterium, Cytophaga, Flexibacter, Saprospira, Flexithrix, Herpetosiphon, Capnocytophaga, Sporocytophaga, Aureobacterium, Agromyces, Arachnia, Rothia, Acetobacterium, Actinomyces, Arthrobactera, Arcanobacterium, Lachnospira, Propionibacterium,* Eubacterium, *Butyrivibria, Brevibacterium, Bifidobacterium, Microbacterium, Caseobacter,* or *Thermoanaerobacter, Enterobacter* sp. 638, or *Burkholderia cepacia* BU72, or other strain.

In an embodiment, the at least one modified microorganism includes MC-1 magnetotactic bacteria. For example, magnetotactic bacteria have flagella that provide for mobilization, and can be combined with nanoparticles of magnetite or magnetosome chains embedded in the bacteria for directing the microbes. See, for example, Felfoul, et al., IEEE Xplore Abstract, issue 22-26, pp. 1463-1466 (2007), which is incorporated herein by reference.

In an embodiment, the modified microorganism includes at least one microorganism with the designation of "generally regarded as safe" (GRAS) status in the food industry.

Many microorganism strains are registered with the American Type Culture Collection (ATCC, Rockville, Md., USA), and can be adapted for use with various embodiments described herein.

In an embodiment, any microorganism for which at least a portion of the genome has been sequenced can be utilized in compositions described herein. For example, by sequencing the genome of a particular microorganism, regulatory elements and sites for chromosomal insertion can be identified. Furthermore, bioinformatics and promoter-trapping strategies can assist in locating endogenous promoters to further regulate production of the at least one therapeutic or environmental medium treatment agent.

In an embodiment, at least one modified microorganism includes a microorganism that is isolated from at least one biological tissue, environmental medium, a subject, or other substrate. The microorganism is modified, and placed into at least one biological tissue, environmental medium, subject, or other substrate (which may be the same or different substrate as the source of the microorganism).

Selection of the particular microorganism can be based on calculations of particular sub-populations in a larger population, a particular subject, a particular state of health of the subject, a particular organ, a particular biological tissue, or a particular biological cell type. For example, the intestinal microflora can contribute to pathogenesis in susceptible subjects, or it can contribute to the metabolism and overall health of the subject. See, for example, O'Hara and Shanahan, EMBO reports, vol. 7, no. 7, pp. 688-693 (2006), which is incorporated herein by reference. Microorganism populations vary according to age, disease state or health state, and diet. Id. For example, *Lactobacilli* are dominant among microflora associated with the urogenital tract of healthy women but are almost completely absent in patients who develop most forms of urinary tract infections. See, for example, Hanniffy, et al., Adv. Applied Microbiol., vol. 56, pp. 1-64 (2004), which is incorporated herein by reference.

Published reports indicate that the human gut microbiota affects nutrition, development, metabolism, pathogen resistance, and regulation of immune responses; and the microbiota community also changes with antibiotic use. See, Dethlefsen, et al., PLOS Biol., vol. 6, no. 11, pp. 2383-2400 (2008), which is incorporated herein by reference. For example, as published, approximately 3300-5700 bacterial taxa were identified as accounting for over 99% of the variable region sequence tags obtained. Id. Also as published, antibiotic use of ciprofloxacin influences about one third of the bacterial taxa in the gut. Id.

Other published studies have found that *Lactococcus* lactis is well adapted to deliver medical proteins to the mucosal immune system, and is capable of delivery proteins that elicit both systemic and mucosal immune responses. For example, *L. lactis* has been used as a live vector for in situ delivery of biologically active IL-12. See, for example, Bermudez-Humaran, et al., J. Mol. Microbiol. Biotechnol. Abstract. Vol 14 (1-3), pp. 80-89 (2008), which is incorporated herein by reference.

Further published reports indicate high diversity of microorganisms located in the human mouth, with a small majority in common amongst any particular geographical region group. See, for example, Myles, et al., Abstract, BMC Med. Gen. vol. 2, no. 45 (2009), which is incorporated herein by reference. For example, the populations of individual groups of bacteria located in the saliva of one person tested were not largely common with other people located in a similar geographical region. Id.

In an embodiment, at least one microorganism (or a population thereof) is obtained from at least one subject, modified, and returned to the at least one subject, and possibly others (e.g., members of a household). In an embodiment, the at least one modified microorganism (or a population thereof) is returned to approximately the same location of the subject from which it was extracted. In an embodiment, the at least one modified microorganism (or a population thereof) is returned to a different location in the subject source. For example, at least one microorganism can be extracted from the intestine of a subject, modified, and returned to the oral cavity, otic cavity, stomach, or intestine of that same subject. In an embodiment, at least one microorganism is extracted, modified, and returned to the subject at approximately the same location from where it was extracted, and the modified microorganism is able to translocate to another location within the subject or to another subject (e.g., maternal transfer, peristalsis through the digestive tract, etc.). In an embodiment, at least some genetic sequence information from the microorganism is obtained prior to or subsequent to modifying the microorganism. In an embodiment, the at least one modified microorganism is amplified prior to reinstating it in the at least one biological tissue, or subject.

Published studies indicate that the human gut contains distinct differences in the microflora of obese subjects, normal weight subjects, and subjects who have undergone gastric bypass surgery. See, for example, Zhang, et al., PNAS, pp. 1-6; available online at 10.10973/pnas.0812600106 (printed 2009, available 2008), which is incorporated herein by reference. Further, these studies indicate a shift in microbiota populations following gastric bypass surgery. Id.

In an embodiment, a microorganism is selected from at least one subject based on a desired state of health, modified to produce at least one therapeutic agent, and placed in the same or different subject. Selection of a particular microorganism can be conducted utilizing conventional techniques, including but not limited to barcoded 16S pyrosequencing. See, for example, Andersson, et al., PLOS One vol. 3, no. 7, pp. 1-8 (2008), which is incorporated herein by reference. The relatively small genome size of microorganisms and the availability of high-throughput sequencing facilities has allowed for the production of sequence information of more than 90 bacterial genomes for the public domain. Id.

In an embodiment, the at least one modified microorganism includes at least one vector including at least one genetic element for producing an agent, or initiating death in the microorganism. Various vectors can be utilized, as described herein, including at least one of a plasmid, bacteriophage, cosmid, artificial chromosome, or other vector. In an embodiment, the modified microorganism includes multiple vectors, some of which can be the same or different from the other vectors. In an embodiment, the modified microorganism includes at least one vector that is able to regulate initiation of death of the at least one modified microorganism, and also generate the at least one therapeutic agent or environmental medium treatment agent.

Vectors suitable for microbiological applications are well known in the art, and are routinely designed and developed for particular purposes. Some non-limiting published examples of vectors that have been used to transform bacterial strains include the following plasmids: pMW211, pBAD-DEST49, pDONRP4-P1R, pENTR-$P_{BAD}$, pENTR-DUAL, pENTR-term, pBR322, pDESTR4-R3, pBGS18-N9uc8, pBS24Ub, pUbNuc, pIXY154, pBR322DEST, pBR322DEST-$P_{BAD}$-DUAL-term, pJIM2093, pTG2247, pMEC10, pMEC46, pMEC127, pTX, pSK360, pACYC184, pBOE93, pBR327, pDW205, pKCL11, pKK2247, pMR60, pOU82, pR2172, pSK330, pSK342, pSK355, pUHE21-2, pEHLYA2-SD, See, for example, Stritzker, et al. Intl. J. Med. Microbiol. Vol. 297, pp. 151-162 (2007); Grangette et al., Infect. Immun. vol. 72, pp. 2731-2737 (2004), Knudsen and Karlstrom, App. and Env. Microbiol. pp. 85-92, vol. 57, no. 1 (1991), Rao et al., PNAS pp. 11193-11998, vol. 102, no. 34 (2005), each of which is incorporated herein by reference.

Therapeutic Agents and Environmental Medium Treatment Agents

Examples of the at least one therapeutic agent or environmental medium treatment agent produced by the at least one modified microorganism are described herein. As indicated, the at least one therapeutic agent is produced for at least one biological tissue, while the at least one environmental medium treatment agent is produced for at least one environmental medium. Thus, in certain instances, the at least one therapeutic agent or at least one environmental medium treatment agent are similar (e.g., mineral), and in other instances, they are different and correspond to the particular biological tissue, or environmental medium, respectively.

In an embodiment, the at least one therapeutic agent or environmental treatment agent is encoded by at least one vector. In an embodiment, the vector includes at least one of a plasmid, bacteriophage, cosmid, artificial chromosome, or other vector. In an embodiment, the vector encodes two or more therapeutic agents or environmental treatment agents. In an embodiment, the two or more therapeutic agents or environmental treatment agents are linked to different promoters. In an embodiment, as described herein, the vector includes at least one of an inducible promoter, inducible enhancer, or inducible repressor.

In an embodiment, the at least one modified microorganism produces at least one therapeutic agent or environmental medium treatment agent. In an embodiment, the at least one therapeutic agent or environmental medium treatment agent includes at least a portion of one of an organic or inorganic small molecule, proteinoid, nucleic acid, peptide, polypeptide, protein, glycopeptide, glycolipid, lipoprotein, lipopolysaccharide, sphingolipid, glycosphingolipid, glycoprotein, peptidoglycan, lipid, carbohydrate, metalloprotein, proteoglycan, vitamin, mineral, amino acid, polymer, copolymer, monomer, prepolymer, cell receptor, adhesion molecule, cytokine, chemokine, immunoglobulin, antibody, antigen, extracellular matrix component, cell ligand, oligonucleotide, element, hormone, or contrast agent.

In an embodiment, the polymer or co-polymer includes at least one of polyester, polylactic acid, polyglycolic acid, cellulose, nitrocellulose, urea, urethane, or other polymer. For example, in an embodiment, at least one microorganism that is capable of synthesizing at least one thermoplastic polymer (e.g., polyester) is utilized. See, for example, U.S. Pat. No. 5,663,063, which is incorporated herein by reference. For example, as described in U.S. Pat. No. 5,663,063, E. coli strains can be modified to produce polyhyroxybutyrate and polyhydroxyalkanoate polyesters. Id.

In an embodiment, at least one microorganism that is capable of degrading at least one polymer (e.g., aliphatic polyester) is utilized. See, for example, Suyama, et al., App. Env. Microbiol. vol. 64, no. 12, pp. 5008-5011 (1998), which is incorporated herein by reference. For example, in an embodiment, the at least one microorganism is capable of degrading at least one of poly(beta-hydroxyalkanoate), poly (epsilon-caprolactone), or poly(hexamethylene carbonate). Id.

In an embodiment, the polymer or co-polymer includes at least one of polyester, polylactic acid, polyglycolic acid, cellulose, nitrocellulose, urea, urethane, or other polymer, as described herein.

In an embodiment, the therapeutic agent or environmental medium treatment agent includes at least one of calcium, carbon, nitrogen, sulfur, nitrate, nitrite, copper, magnesium, selenium, boron, sodium, aluminum, phosphorus, potassium, titanium, chromium, manganese, iron, nickel, zinc, silver, barium, lead, vanadium, tin, strontium, or molybdenum.

In an embodiment, the at least one therapeutic agent or environmental medium treatment agent includes at least one enzyme able to convert at least one prodrug or precursor compound into an active state. In an embodiment, the at least one enzyme includes at least one of beta glucuronidase, cytosine deaminase, or nitroreductase. In an embodiment, the at least one therapeutic agent or environmental medium treatment agent includes at least one nutraceutical. In an embodiment, the at least one therapeutic agent or environmental medium treatment agent excludes nutraceuticals.

In an embodiment, the at least one therapeutic agent or environmental medium treatment agent is pH dependent. Thus, in certain embodiments, the agent can be administered to one particular location and remain inactive until conditions change that result in alteration of the pH of the location (or the modified microorganism travels to another location with a different pH), and the agent becomes active. The activity of the agent can be gradual (along a gradation), or immediate. As described herein, various formulations for the compositions disclosed can be provided, depending on the location and the therapeutic agent.

In an embodiment, the at least one therapeutic agent is capable of modulating at least one immune response. In an embodiment, wherein the at least one immune response includes at least one allergic or autoimmune response. In an embodiment, the at least one therapeutic agent is capable of inducing apoptosis in one or more cells of the at least one biological tissue. In an embodiment, the at least one administered therapeutic agent modulates the viability, proliferation, or metastasis of at least one tumor cell in the at least one biological tissue.

In an embodiment, the at least one therapeutic agent includes at least one of insulin, clacitonin, lutenizing hormone, parathyroid hormone, somatostatin, thyroid stimulating hormone, vasoactive intestinal polypeptide, tumor necrosis metabolite, endostatin, angiostatin, anti-angiogenic antithrombin II, fibronectin, prolactin, thrombospondin I, laminin, procollagen, collagen, integrin, steroid, corticosteroid, virus antigen, microorganism antigen, trefoil protein, or lipase.

The trefoil peptide can include, but not be limited to, TFF1 (also known as pS2, or breast cancer estrogen inducible gene), TFF2 (also known as SP, or spasmolytic peptide), or TFF3 (also known as ITF, or intestinal trefoil factor). See, for example, U.S. Patent Application Publication Nos. 20070110723, and 20070122427; each of which is incorporated herein by reference. See also, U.S. Pat. No. 7,220,418, which is incorporated herein by reference. The vaccine can include but not be limited to antigenic peptides, proteins, or carbohydrates. For example, the vaccine can include but not be limited to envelope proteins, capsid proteins, surface proteins, toxins, polysaccharides, oligosaccharides, or enzymes needed to make at least one thereof.

In an embodiment, the virus antigen includes at least one antigen from one or more of a double-stranded DNA virus, single-stranded DNA virus, double-stranded RNA virus, (+) single-strand RNA virus, (−) single-strand RNA virus, single-strand RNA-Reverse Transcriptase virus, or double-stranded DNA-Reverse Transcriptase virus. In an embodiment, the virus antigen includes at least one antigen of a virus from one or more of the family of Adenoviridae, Arenaviridae, Bunyaviridae, Calciviridae, Circoviridae, Coronaviridae, Filoviridae, Flaviviridae, Hepadnaviridae, Herpesviridae, Orthomyxoviridae, Papovaviridae, Papillomaviridae, Polyomaviridae, Paramyxoviridae, Parvoviridae, Picornaviridae, Poxviridae, Reoviridae, Retroviridae, Rhabdoviridae, Pseudoviridae, or Togaviridae. In an embodiment, the virus antigen includes at least one antigen from one or more of human immunodeficiency virus (HIV) type I, HIV-type 2, simian immunodeficiency virus (SIV), or feline leukemia virus. In an embodiment, the virus antigen includes at least one antigen from one or more of respiratory syncytial virus (RSV), influenza (flu), adenovirus, rhinovirus, enterovirus, poliovirus, rubella virus, paramyxovirus, herpes simplex virus type I (HSV-1), Herpes simplex virus 2 (HSV-2), rotavirus, neurotropic virus, coxsackie virus, hepatitis virus type A, hepatitis virus type B, hepatitis virus type C, or oncovirus. In an embodiment, the at least one antigen includes at least one antigen from one or more of *Brucella, Chlamydia, Citrobacter, Coxiella brunetii, Escherichia coli, Francisella tularensis, Haemophilius, Legionella, mycobacterium, Neisseria, Pseudomonas, Rickettsia, Salmonella, Shigella, Staphylococcus, Streptococcus, Candida, Cryptococcus, Aspergillus, Blastomyces, Histoplasma, Paracoccidioides, Nosema, Encephalitozoon, Torulopsis, Pneumocystis, Trypanosoma, Leishmania, Theileria, Plasmodium, Cryptosporidium*, or *Toxoplasma*.

In an embodiment, the at least one therapeutic agent includes at least one vaccine. In an embodiment, the at least one vaccine includes at least one of an antigenic peptide, antigenic protein, or antigenic carbohydrate. In an embodiment, the at least one vaccine includes at least one of an envelope protein, capsid protein, surface protein, toxin, polysaccharide, oligosaccharide, or enzyme needed to make at least one thereof. In an embodiment, the vaccine composition further comprises at least one adjuvant. In an embodiment, the at least one therapeutic agent includes at least one anti-inflammatory cytokine.

In an embodiment, at least one therapeutic agent includes at one of Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin-12, Interleukin-13, Interleukin-14, Interleukin-15, Interleukin-16, Interleukin-17, Interleukin-18, Interleukin-19, Interleukin-20, Interleukin-21, Interleukin-22, Interleukin-23, Interleukin-24, Interleukin-25, Interleukin-26, Interleukin-27, Interleukin-28, Interleukin-29, Interleukin-30, Interleukin-31, Interleukin-32, Interleukin-33, Interleukin-34, Interleukin-35, Interleukin-36, Interleukin-37, Interleukin-38, Interleukin-39, Interleukin-40, Interleukin-41, Interleukin-42, Interferon-γ, Interferon-α, Interferon-β, Transforming Growth factor, Granulocyte Macrophage-Colony Stimulating Metabolite, Macrophage-Colony Stimulating Metabolite, Scarecrow, Erythropoietin, Granulocyte-Colony Stimulating Metabolite, Leukemia Inhibitory Metabolite, Oncostatin M, Ciliary Neurotrophic Metabolite, Growth Hormone, Prolactin, Fibroblast Growth factor, Nerve Growth factor, Platelet Derived Growth factor, Epidermal Growth factor, Fas, Fas ligand, CD40, CD27, CD4, CD8, CD2, CD3, Tumor Necrosis Metabolite-α, or Tumor Necrosis Metabolite-β.

Chemokines are biochemical signaling molecules that act to attract other particular molecules, including but not limited to cells, to a specific site. In at least one embodiment, the therapeutic agent includes one or more chemokines. In at least one embodiment, the one or more chemokines include at least one of a CC chemokine, CXC chemokine, C chemokine, or CX3C chemokine. In an embodiment, the at least one therapeutic agent includes at least one of CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CCL29, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, CXCL18, CXCL19, CXCL20, CXCL21, CXCL22, XCL1, XCL2, XCL3, XCL4, XCL5, CX3CL1, CX3CL2, or CX3CL3.

In an embodiment, administration of the at least one therapeutic agent results in at least one of nucleic acid transcription, protein translation, cell division, apoptosis, necrosis, cytoskeletal rearrangement, cell differentiation, or secretion in the at least one biological tissue.

In an embodiment, the at least one therapeutic agent includes at least one prodrug or precursor compound. For example, the at least one prodrug or precursor compound includes at least one glucuronide prodrug, such as at least one glucuronide of epirubicin, 5-fluorouracil, 4-hydroxycyclophosphamide, or 5-fluorocytosine. In another example, the at least one prodrug or precursor compound includes 5-(aziridin-1-yl)-2,4-dinitrobenzamide. In an embodiment, the at least one therapeutic agent includes at least one prodrug. In an embodiment, at least one modified microorganism delivers at least one prodrug, while at least one other modified microorganism delivers at least one enzyme capable of converting the at least one prodrug into active form. For example, published studies demonstrating strains of recombinant *Saccharomyces cerevisiae* expressing plant P450 73A1 show that the enzyme is active and able to convert trans-cinnamic acid into p-coumaric acid in vivo. See, for example, Garrait, et al., Applied Env. Microbiol. vol. 73, no. 11, pp. 3566-3574 (2007), and Blanquet, et al., Applied Env. Microbiol. vol. 69, no. 5, pp. 2884-2892 (2003), each of which is incorporated herein by reference. In an embodiment, the at least one therapeutic agent or environmental medium treatment agent includes at least one converting enzyme responsive to the at least one prodrug or precursor compound. In an embodiment, the at least one therapeutic agent or environmental medium treatment agent includes at least one time-release formulation. In an embodiment, the at least one therapeutic agent or environmental medium treatment agent is pH dependent or temperature dependent.

In an embodiment, the at least one modified microorganism delivers at least two different therapeutic agents. In certain cases, the at least two different therapeutic agents are regulated by at least one different promoter. In an embodiment, at least one therapeutic agent includes at least one antigen, and at least one cytokine. In an embodiment, the at least one antigen includes tetanus toxin fragment. In an embodiment, the at least one cytokine includes at least one of IL-2 or IL-6. In an embodiment, the antigen is contained within the at least one modified microorganism, while the cytokine is secreted. See, for example, Steidler, et al. Infect. Immun. pp. 3183-3189, vol. 66, no. 7 (1998), and U.S. Pat. No. 6,605,286; each of which is incorporated herein by reference. In another example, published studies show secretion of human myelin basic protein (hMBP) or hMBP as a fusion protein with beta-glucuronidase from *E. coli*. The heterologous products are produced by *L. casei*. See, for example, Maassen, et al., Vaccine, Abstract, vol. 17, no. 17, pp. 2117-2128 (1999), which is incorporated herein by reference.

The at least one modified microorganism includes at least one heterologous genetic element encoding at least one therapeutic agent or environmental medium treatment agent by at least one of mode, including but not limited to synthesizing the at least one agent, expressing the at least one agent on its surface, or extracellular secretion of the at least one therapeutic agent or environmental medium treatment agent.

In an embodiment, the at least one modified microorganism includes at least one heterologous genetic element encoding at least one therapeutic agent and expresses at least a portion of the agent (e.g. antibody) on its surface. In an embodiment, the at least one modified microorganism expresses at least a portion of a carbohydrate-binding motif on its surface. In one example, the at least one modified microorganism expresses at least one of a heparin or mannose binding motif its surface.

Figure 4:
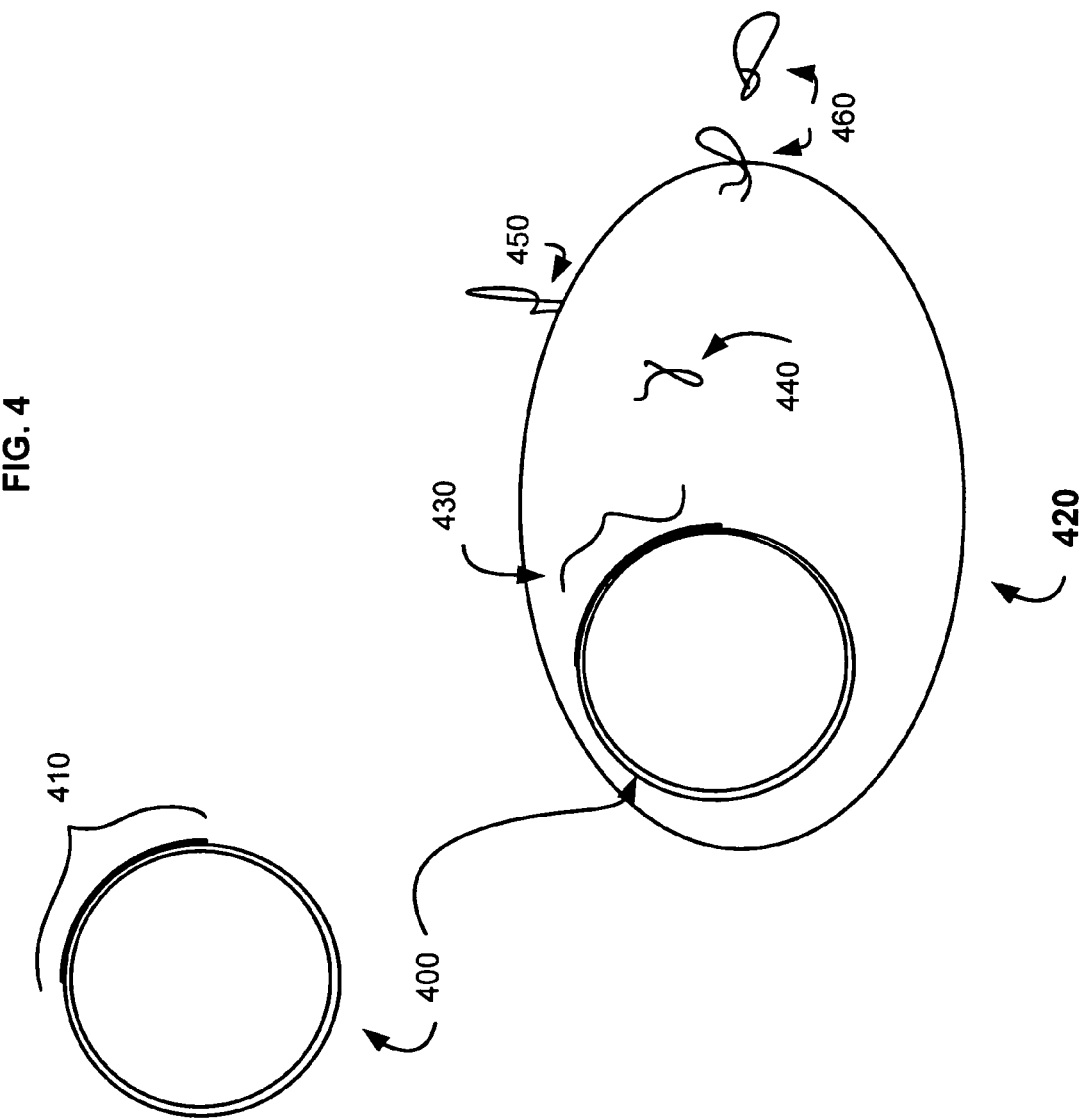
FIG. 4 illustrates a partial view of particular genetic elements utilized in various embodiments disclosed herein.

For example, as illustrated in FIG. 4, in an embodiment, a vector 400 including at least one heterologous genetic element 410 is placed into at least one microorganism 420 by methods known in the art (e.g., electroporation, transformation, etc.). Once incorporated into the microorganism 420, the heterologous genetic element 410 is transcribed, resulting in production of at least one transcript 430, which is converted intracellularly into at least one protein 440. In an embodiment, the protein can remain intracellularly 440 or be secreted into a periplasmic space (not shown). Thus, the protein is obtained through lysis of the microorganism 420. In an embodiment, the protein is expressed on the surface 450 of the microorganism 420. In an embodiment, the protein is secreted extracellularly 460.

In an embodiment, the at least one modified microorganism includes at least one synthetic protein scaffold positioned to modulate the stoichiometry of the synthesis of the at least one therapeutic agent or environmental medium treatment agent. For example, in an embodiment, the at least one synthetic protein scaffold is positioned to spatially or temporally recruit at least one protein or fragment thereof. For example, synthetic protein scaffolds that spatially recruit metabolic enzymes can be designed and modulate the stochiometry of a biosynthetic pathway. See, for example, Dueber et al., Nat. Biotech. vol. 27, no. 8, pp. 753-759 (2009), which is incorporated herein by reference. In one example, at least one flux of an enzymatic reaction of a particular biosynthetic pathway can be balanced to, for example, limit the accumulation of intermediates, optimize production levels, prevent loss of intermediates, protect unstable intermediates from degradation, circumvent unfavorable equilibria and kinetics imposed by bulk-phase metabolite concentration, etc. Id. In an embodiment, scaffolds provide a means for controlling design by physically separating catalytic activities from binding element, which allows modification (i.e., single interaction to each enzyme) to the enzyme needed for attaining modular control over complex formation. Id. Designing such scaffolds can be performed by tethering a short peptide ligand to the enzyme, for example an SH2 domain, SH3 domain, GTPase binding domain, etc. In one particular embodiment, a synthetic complex is designed by attaching a varying number of SH3 interaction ligands to the C terminus of one enzyme (e.g., synthase), and attaching an SH3 domain to the N terminus of another enzyme (e.g., reductase). Id.

In an embodiment, the at least one modified microorganism includes at least one riboregulated transcriptional cascade counter. See, for example, Friedland, et al., Science, vol. 324, pp. 1199-1202, (2009), which is incorporated herein by reference. In an embodiment, the at least one riboregulated transcriptional cascade counter is positioned to produce at least one product upon exposure to at least one inducer.

Various inducers are described herein. Several non-limiting examples include physical or chemical inducers, such as radiation, temperature, carbohydrate, peptide, protein, alcohol, antibiotic, steroid, metal, salicylic acid, ethylene, benzothiadiazole, or other compound. In an embodiment, the at least one antibiotic includes at least one of ampicillin, tetracycline, penicillin, pristinamycin, or other antibiotic. In an embodiment, multiple different inducers may be required for the various inducible genetic elements.

In an embodiment, the at least one riboregulated transcriptional cascade counter is positioned to produce at least one sequence of products upon exposure to at least one sequence of inducers. In an embodiment, the at least one riboregulated transcriptional cascade counter is positioned to produce at least one product that is different than at least one other consecutive product. In an embodiment, the at least one riboregulated transcriptional cascade counter is positioned to produce at least one first product upon exposure to at least one first inducer. In an embodiment, the at least one riboregulated transcriptional cascade is inducible to produce at least one second product upon exposure to at least one second inducer. In an embodiment, the at least one riboregulated transcriptional cascade is inducible to produce at least one third product upon exposure to at least one third inducer, etc. See Friedland, Ibid. In an embodiment, one or more of the first product, the second product, or the third product includes the at least one therapeutic agent or environmental medium treatment agent.

In an embodiment, the at least one modified microorganism is inducible to produce the at least one agent by at least one twin-arginine translocation system. See, for example, Widdick, et al., PNAS, vol. 103, no. 47, pp. 17927-17932 (2006), which is incorporated herein by reference. For example, in most bacteria, the general secretory pathway (Sec) is the predominant route for protein export. Id. Proteins exported via Sec are translocated across the membrane in an unfolded state through a membrane-embedded translocon, to which they are targeted by cleavable N-terminal signal peptides. Id. A second export pathway designated Tat (for twin-arginine translocation), transports prefolded protein substrates. Id. Proteins are targeted to the Tat pathway by tripartite N-terminal signal peptides, which contain a conserved twin-arginine motif in the N region of Tat signal peptides. Id. The motif is described as R-R-x-Φ-Φ, where Φ represents a hydrophobic amino acid. The consecutive arginine residues are almost invariant and believed to be important for transport by this pathway. Id. The Tat system is capable of producing large proteins, and proteins with lipid anchors, which are sometimes difficult to produce by way of the Sec system. Id. According to published studies, the twin arginine translocation system has been demonstrated to be usable in various microorganisms. See, for example, Maillard, et al., PNAS, vol. 104, no. 40, pp. 15641-15646; U.S. Pat. No. 7,447,595; each of which is incorporated herein by reference.

In an embodiment, the at least one modified microorganism includes a microorganism having one or more non-reverting mutations. For example, a non-reverting mutation can involve a polynucleotide of greater than about 1 nucleotide, greater than about 2 nucleotides, greater than about 3 nucleotides, greater than about 4 nucleotides, greater than about 5 nucleotides, greater than about 10 nucleotides, greater than about 15 nucleotides, greater than about 20 nucleotides, or any value therebetween.

In an embodiment, the non-reverting mutation blocks at least one biosynthetic pathway of the microorganism. For example, the non-reverting mutation can include one or more of a deletion, insertion, inversion, or any combination of these. Developing modified microorganisms containing non-reverting mutations is a routine practice, and is based on several non-limiting factors, including the ability to mutate a particular gene without destroying the viability of the microorganism, the nature of the at least one therapeutic agent that is to be delivered by the modified microorganism, the nature of the microorganism, and in some cases, the nature of the subject that will host the modified microorganism. For example, in an embodiment the mutated gene prevents production of at least one enzyme that is required for a biosynthetic pathway of a metabolite needed for replication or protein synthesis, without sacrificing viability of the microorganism (e.g., aro genes, pab genes, pur genes, etc.). See, for example, U.S. Pat. No. 4,837,151, which is incorporated herein by reference. Standard methods for making non-reverting mutants include, but are not limited to, introducing transposable elements, site directed mutagenesis, conjugational crossing, or other form of mutagenesis. The modified microorganism is produced by transduction, transformation, or other means.

In an embodiment, the at least one therapeutic agent is able to translocate to at least one other location in the biological tissue or subject. For example, in an embodiment, the at least one modified microorganism delivers at least one therapeutic agent to the gastro-intestinal region of a subject, where it is absorbed and utilized at a distant location in the same subject (e.g., lungs, heart, etc.). In an embodiment, the at least one therapeutic agent translocates systemically. In an embodiment, the at least one therapeutic agent translocates selectively to a location (e.g., by utilizing particular cell ligand-receptor interactions, oxygen or other gas levels, magnetic particles tagged to the microorganism, or other mechanism for directing the microorganism, etc.).

Likewise, in an embodiment, the at least one environmental medium treatment agent is able to translocate to at least one other location in the environmental medium. For example, in an embodiment, the at least one modified microorganism delivers at least one environmental medium treatment agent to the environmental medium and the environmental medium treatment agent spreads by osmosis, water flow, etc. to at least one other location in the environmental medium. In an embodiment, the translocation is directed (e.g., by water flow direction, etc.).

In an embodiment, the modified microorganism produces at least one environmental medium treatment agent or therapeutic agent that catalyzes the conversion of a prodrug to its active state. For instance, in an embodiment, at least one anaerobic microorganism is administered to a tumor that has a largely anaerobic environment. The anaerobic microorganism is allowed to proliferate and produce an enzyme or other factor. Prior to, during, or after administration of the at least one anaerobic microorganism, at least one prodrug is administered to the tumor (e.g., by way of a microorganism or other form of administration). The enzyme or other factor secreted by the at least one anaerobic microorganism converts the at least one prodrug to an active state (e.g., to a cytotoxic agent). For example, the at least one enzyme includes at least one of beta glucuronidase or cytosine deaminase. In an embodiment, the at least one prodrug includes at least one glucuronide prodrug. In an embodiment, the at least one glucuronide prodrug includes at least one glucuronide of epirubicin, 5-fluorouracil, 4-hydroxycyclophosphamide, or 5-fluorocytosine. See, for example, U.S. Pat. No. 6,652,849, which is incorporated herein by reference.

In another example, the enzyme includes nitroreductase, and the prodrug includes 5-(aziridin-1-yl)-2,4-dinitrobenzamide (CB1954). See, for example, U.S. Pat. No. 6,416,754, which is incorporated herein by reference.

In an embodiment, the composition is formulated for administration to at least one biological tissue by at least one route including peroral, topical, transdermal, epidermal, intravenous, intraocular, tracheal, transmucosal, intracavity, subcutaneous, intramuscular, inhalation, fetal, intrauterine, intragastric, placental, intranasal, interdermal, intradermal, enteral, parenteral, surgical, or injection. In an embodiment, the intracavity route includes at least one of oral, vaginal, uterine, rectal, nasal, peritoneal, ventricular, or intestinal. The delivery may include inhalation, depot injections, implants, or other mode of delivery by way of an apparatus.

In an embodiment, a composition includes a time-release formulation. In at least one embodiment, the composition includes at least one of an suspension, mixture, solution, sol, clathrate, colloid, emulsion, microemulsion, aerosol, ointment, capsule, micro-encapsule, powder, tablet, suppository, cream, device, paste, resin, liniment, lotion, ampule, elixir, spray, syrup, foam, pessary, tincture, detection material, polymer, biopolymer, buffer, adjuvant, diluent, lubricant, disintegration agent, suspending agent, solvent, light-emitting agent, colorimetric agent, glidant, anti-adherent, anti-static agent, surfactant, plasticizer, emulsifying agent, flavor, gum, sweetener, coating, binder, filler, compression aid, encapsulation aid, preservative, granulation agent, spheronization agent, stabilizer, adhesive, pigment, sorbent, nanoparticle, microparticle, or gel.

In an embodiment, the composition includes a lyophilized formulation. In an embodiment, the composition forms at least part of a food product. In an embodiment, the composition is formulated to be included with at least part of one or more of a food product, lip balm, lotion, ointment, sunscreen or sunblock, perfume, aftershave, shampoo or other hair products, nail polish, dentures or other oral implants, contact lens or other ocular implants, orifice insert, orifice spray or inhaler, sutures, surgical staples, dental floss, stents, shunts, bandages, absorbable mesh, or oral consumable.

The formulation of any of the compositions described herein may be formulated neat or may be combined with one or more acceptable carriers, diluents, excipients, and/or vehicles such as, for example, buffers, surfactants, preservatives, solubilizing agents, isotonicity agents, and stablilizing agents as appropriate. A pharmaceutically acceptable carrier, for example, may be approved by a regulatory agency of the state and/or Federal government such as, for example, the United States Food and Drug Administration (US FDA) or listed in the U.S. Pharmacopeia or other generally recognized pharmacopeia for use in animals, and more particularly in humans. Conventional formulation techniques generally known to practitioners are described in Remington: The Science and Practice of Pharmacy, 21$^{st}$ Edition, Lippincott Williams & Wilkins, Baltimore, Md. (2000), which is herein incorporated by reference.

Acceptable pharmaceutical carriers include, but are not limited to, the following: sugars, such as lactose, glucose and sucrose; starches, such as corn starch and potato starch; cellulose, and its derivatives, such as sodium carboxymethyl cellulose, ethyl cellulose, bovine serum albumin, keyhole limpet hemocyanin, tetanus toxoid, cellulose acetate, and hydroxymethylcellulose; polyvinylpyrrolidone; cyclodextrin and amylose; powdered tragacanth; malt; gelatin, agar and pectin; talc; oils, such as mineral oil, polyhydroxyethoxylated castor oil, peanut oil, cottonseed oil, safflower oil, sesame oil, olive oil, corn oil and soybean oil; polysaccharides, such as alginic acid and acacia; fatty acids and fatty acid derivatives, such as stearic acid, magnesium and sodium stearate, fatty acid amines, pentaerythritol fatty acid esters; and fatty acid monoglycerides and diglycerides; glycols, such as propylene glycol; polyols, such as glycerin, sorbitol, mannitol and polyethylene glycol; esters, such as ethyl oleate and ethyl laurate; buffering agents, such as magnesium hydroxide, aluminum hydroxide and sodium benzoate/benzoic acid; water; isotonic saline; Ringer's solution; ethyl alcohol; phosphate buffer solutions; other non-toxic compatible substances employed in pharmaceutical compositions. The pharmaceutical compositions are generally formulated as sterile, substantially isotonic and in full compliance with all Good Manufacturing Practice (GMP) regulations of the U.S. Food and Drug Administration.

In an embodiment, the composition further comprises at least one detection material associated with the at least one modified microorganism. In an embodiment, the at least one detection material includes at least one taggant, contrast agent, sensor, or electronic identification device. In an embodiment, the at least one electronic identification device includes at least one radio frequency identification device.

In an embodiment, the at least one sensor includes at least one biosensor. In an embodiment, the at least one biosensor includes at least one modified microorganism. In an embodiment, the at least one modified microorganism detects the at least one agent. For example, in an embodiment, a biosensor microorganism expresses green fluorescent protein (or another measurable material) upon exposure to the at least one agent. See, for example, Hansen et al., App. Env. Microbiol. vol. 67, no. 1, pp. 239-244 (2001), which is incorporated herein by reference. In an embodiment, the biosensor microorganism expresses a measurable material upon exposure to at least one byproduct of the modified microorganism. For example, as set forth in Hansen, et al., a modified microorganism expresses green fluorescent protein in the presence of tetracycline, which is produced by a naturally occurring bacterial strain. Id. As indicated, testing was conducted by inoculating soil with the biosensor microorganisms, and detecting the biosensor microoganisms by flow cytometry. Id. For example, induced biosensor bacteria were isolated using fluorescence-activated cell sorting (FACS) and examined by epifluorescence microscopy. Id.

In an embodiment, the at least one detection material includes at least one of a radioactive, luminescent, colorimetric or odorous substance. In an embodiment, the detection material includes at least one of a diamagnetic particle, ferromagnetic particle, paramagnetic particle, super paramagnetic particle, particle with altered isotope, or other magnetic particle. In an embodiment, the detection material includes at least one RNA or DNA device. In an embodiment, the detection material or a precursor thereof is encoded by the at least one heterologous genetic element encoding at least one therapeutic agent or environmental medium treatment agent. In an embodiment, the detection material includes the at least one therapeutic agent or environmental medium treatment agent, or a metabolite thereof.

In an embodiment, the detection material includes at least one nucleic acid device, such as a DNA or RNA device. In an embodiment, the nucleic acid device includes a single input-single output RNA device based on the assembly of three functional components: a sensor made of an RNA aptamer; an actuator made of a hammerhead ribozyme; and a transmitter made of a sequence that couples the sensor and actuator components. See, for example, Win and Smolke, Science, vol. 322, pp. 456-460 (2008), which is incorporated herein by reference. Such devices distributed between two primary conformations: one in which the input cannot bind the sensor, and the other in which the input can bind the sensor as a result of competitive hybridization events within the transmitter component. Id. Input binding shifts the distribution to favor the input-bound conformation as a function of increasing input concentration and is translated to a change in the activity of the actuator, where a "ribozyme-active" state results in self-cleavage of the ribozyme. Id.

In an embodiment, the detection material includes the at least one therapeutic agent, environmental medium treatment agent, or metabolite thereof.

In an embodiment, the at least one environmental medium includes at least one of a solid, liquid, or gas. In an embodiment, the at least one environmental medium includes at least one of water, soil, food product, or air or other gas. In an embodiment, the at least one environmental medium includes at least one of ground water, surface water, effluent, or wastewater. In an embodiment, the water includes at least one of a lake, river, stream, sludge, slurry, sewage, ocean, fountain, or other water. In an embodiment, the at least one environmental medium includes water contained in an at least partially enclosed space (e.g., septic tank, lagoon, dam, wastewater treatment vessel, etc.).

In an embodiment, the at least one environmental medium includes at least one of a structure or device. In an embodiment, the structure includes at least one of metal, concrete, cement, textiles, fabric, wood, mineral ore, or rock. In an embodiment, the device includes at least one of a patch, bandage, shunt, wound dressing, splint, computer mouse, telephone, mobile phone, writing instrument, article of clothing, blanket, pen-type injection device, other injection device, medical instrument, or other article of manufacture.

In an embodiment, the at least one modified microorganism degrades or converts at least one hydrocarbon source. For example, alkanes, alkenes, alkynes, polyalkenes, polyalkynes, chlorinated, volatile, or aliphatic hydrocarbons are common contaminants in soil, or ground water. Such hydrocarbons are a common constituent in solvents, degreasers, and other compounds. Other non-limiting examples of hydrocarbon compounds include chlorinated aliphatic hydrocarbons, chlorinated aromatic hydrocarbons, or non-chlorinated aromatic hydrocarbons. Non-limiting examples of hydrocarbon contaminants or other contaminants that can be utilized by at least one modified microorganism include methylene chloride, 1,1-dichloroethane, chloroform, 1,2-dichloropropane, dibromochloromethane, 1,1,2-trichloroethane, 2-chloroethylvinyl ether, tetrachloroethene (PCE), chlorobenzene, 1,2-dichloroethane, 1,1,1-trichloroethane, bromodichloromethane, trans-1,3-dichloropropene, cis-1,3-dichloropropene, bromoform, benzene, toluene, ethylbenzene, xylenes, chloromethane, bromomethane, vinyl chloride, chloroethane, 1,1-dichloroethene, trans-1,2-dichloroethene, trichloroethene (TCE), dichlorobenzenes, cis-1,2-dichloroethene, dibromomethane, 1,4-dichlorobutane, 1,2,3-trichloropropane, bromochloromethane, 2,2-dichloropropane, 1,2-dibromoethane, 1,3-dichloropropane, bromobenzene, chlorotoluenes, trichlorobenzenes, trimethylbenzenes, trans-1,4-dichloro-2-butene, butylbenzenes, methyl tertiary butyl ether, polychlorinated biphenyl, or polycyclic aromatic hydrocarbon. In another example, a particular contaminant includes, but is not limited to, heavy metals such as arsenic, antimony, beryllium, cadmium, chromium, copper, lead, mercury, iron, manganese, radium, nickel, selenium, silver, thallium, or zinc. In another example, a particular contaminant includes, but is not limited to, nitrogen-based aromatic compounds, pesticides, esters, ethers, aldehydes, amines, dioxins, herbicides, ketones, phenols, alcohols, sulfur-containing compounds, ethylene dibromide, chlorophnolic compounds, chlorate, cyanide, halogenated compounds, radioactive compounds, and other contaminants.

Bioremediation of an environmental medium, by removing contaminant hydrocarbons, heavy metals, or other substances from environmental media can be performed by utilizing hydrocarbon utilizing bacteria (e.g., methanotropic bacteria) or other microorganisms. For example, microbial oxidation of alkanes ($C_3$-$C_6$) have been shown to include a number of chemical processes, including terminal oxidation, and methyl ketone formation. See, for example, Blevins and Perry, J. Bacteriol. vol. 112, no. 1, pp. 513-518 (1972), which is incorporated herein by reference. The terminally oxygenated product may be catabolized further by alpha oxidation (i.e. removal of one carbon at each step), or by beta oxidation. Methyl ketones can be metabolized to the alpha-hydroxy ketone, as with acetone or acetol, or the methyl ketone can be subterminally oxidized to an acetate ester, which is cleaved to yield acetate and a primary alcohol. Id.

In an example, methane-utilizing bacteria can degrade TCE metabolically or cometabolically, either by introduction into the environmental medium directly or by introduction to batches of hydrocarbon-laden environmental medium in an at least partially enclosed space (e.g., a bioreactor). In an embodiment, the at least one modified microorganism utilizes the at least one hydrocarbon as a food source, and oxygen (or another element) as an electron acceptor. In an embodiment, microorganisms utilize enzymes that are capable of replacing halogen substituents in aliphatic and aromatic compounds with hydroxyl groups or hydrogen atoms. See, for example, Muller and Lingens, Abstract, Ang Chem Int Ed English, vol. 25, no. 9, pp. 779-789 (2003), which is incorporated herein by reference.

In an embodiment, at least one modified microorganism is contacted with the at least one substrate, such as an environmental medium (e.g., soil, water, etc.) to be treated. For example, the at least one modified microorganism can be contacted with the at least one substrate in combination with at least one of pumping and treating, air sparging, drilling, oil vapor extraction with activated carbon, etc. In an embodiment, at least a partial vacuum is maintained within the substrate to be treated in order to confine the hydrocarbon source, or assist an anaerobic modified microorganism. In an embodiment, a venting system provides additional oxygenation for degradation by the at least one modified microorganism.

In an embodiment, at least one modified microorganism is capable of metabolizing or co-metabolizing iron or manganese from at least one substrate. In an embodiment, at least one metal is oxidized and precipitated from the at least one substrate. In an embodiment, the at least one metal is precipitated by means including but not limited to pH change, redox potential change, metal reduction, or other means provided by the at least one modified microorganism. In an embodiment, chelated iron is released by the at least one modified microorganism.

In an embodiment, the at least one substrate includes at least one of rock, or mineral ore. In an embodiment, the mineral ore includes, but is not limited to, iron ore, copper ore, zinc ore, nickel ore, uranium ore, gold ore, silver ore, or other ores. For example, precious metals can be biooxidized from rock or mineral ore directly, or indirectly by the addition of an additive (e.g., hydrocarbon), and allowing microorganisms to oxidize the iron, sulfur, or other elements surrounding the precious metals (e.g., gold, silver, etc.). See, for example, U.S. Pat. No. 6,875,356, which is incorporated herein by reference. In an embodiment, at least one modified microorganism capable of bio-oxidizing compounds from rock or mineral ore is utilized to administer at least one agent (e.g., carbon, calcium, other minerals, etc.). In an embodiment, the at least one ore is leached to cause the dissolution of the metal from the ore. In an embodiment, the leached ore is biooxidized with a lixiviant, and the precious metals are recovered from the lixiviant.

In an embodiment, the precious metals are extracted from the mineral ore by the at least one modified microorganism, and at least one nutrient that encourage plant growth is delivered by the at least one modified microorganism. As described herein, in an embodiment the metal is extracted from the ore by direct application of the at least one modified microorganism, or through batch-processing amounts of the ore in an at least partially enclosed space (e.g., bioreactor).

In an embodiment, the at least one modified microorganism includes an endophytic microorganism. For example, endophytic microorganisms are commonly associated with plant roots, or other plant parts. Endophytes can also be identified by amplification (e.g., culturing, or (RT-)PCR amplification of nucleic acids) or direct sequencing of nucleic acids.

In an embodiment, the at least one environmental medium treatment agent includes at least one plant hormone. In an embodiment, the at least one agent includes at least one of an auxin, abscisic acid, cytokinin, ethylene, gibberellin, brassinolide, salicyclic acid, jasmonate, polyamine, plant peptide hormone, nitric oxide, strigolactone, or other compound. Plant hormones are capable of regulating various aspects of plant growth, plant differentiation, and plant development. For example, plant hormones regulate formation of flowers, stems, and leaves; shedding of leaves; development of fruit, and ripening of fruit, cold tolerance, pathogenic tolerance, overall growth, propagation, reproduction, as well as other processes. In an embodiment, the plant hormone includes a naturally occurring plant hormone. In an embodiment, the plant hormone includes a synthetic or artificial hormone. In an embodiment, at least one modified microorganism is capable of producing multiple plant hormones.

Methods of Administration of Modified Microorganisms to Biological Tissues

At least one embodiment disclosed herein includes one or more methods for administering at least one therapeutic agent to at least one biological tissue, comprising providing a composition to at least one biological tissue; wherein the composition includes at least one modified (e.g., auxotrophic) microorganism including at least one heterologous genetic element encoding at least one therapeutic agent. Various embodiments of compositions have been described herein.

For example, in an embodiment a method of administering at least one therapeutic agent to at least one biological tissue comprises: providing a composition to at least one biological tissue; wherein the composition includes at least one auxotrophic microorganism including at least one pH inducible heterologous genetic element encoding at least one therapeutic agent formulated for at least one biological tissue, and including at least one genetic element inducible to initiate death of the at least one auxotrophic microorganism; and the composition further including at least one metabolite required by the at least one auxotrophic microorganism.

As described herein, in an embodiment, the at least one treatment or therapy can be associated with preventative or prophylactic treatment, responsive treatment, or both. In an embodiment, the at least one composition provides an effective amount of at least one therapeutic agent in relation to at least one disease, condition, symptom or disorder. In an embodiment, the effective amount of at least one therapeutic agent is provided in relation to at least one disease, condition, symptom, or disorder.

In an embodiment, the effective amount of at least one therapeutic agent is provided in relation to at least one infection. In an embodiment, the effective amount of at least one therapeutic agent is provided in relation to at least one of inflammatory bowel disease, enteritis, colitis, cancer, gastrointestinal disorder, spondyloarthropathy, HIV/AIDS, Crohn's disease, ulcerative colitis, acute colitis, mucosal lesions, gastritis, Menetier's syndrome, gastro-esophageal reflux, peptic or duodenal ulcer, dyspepsia, dental caries, vaginal candidiosis, allergic reaction, lactose intolerance, lowering of cholesterol, atherosclerosis, prevention of infection, lowering blood pressure, diarrhea, fever, anemia, anorexia, abdominal cramps, autoimmune disease, metabolic defects, diabetes, promoting wound healing, decreasing scar formation, obesity, or malnutrition.

In an embodiment, the infection includes at least one of vaginal infection, oral infection, dental infection, urogenital infection, ear infection, eye infection, tonsillitis, ulcer, intestinal blockage or infection, skin infection, nail infection, sinus infection, urinary tract infection, kidney infection, pharyngitis, laryngitis, or bronchitis.

In an embodiment, the at least one metabolite includes an antimicrobial agent. In an embodiment, the at least one metabolite includes an antibiotic. In an embodiment, the at least one modified microorganism is resistant to the at least one metabolite. In an embodiment, the method further comprises administering at least one antibiotic to the at least one biological tissue or environmental medium prior to, during, or subsequent to administering the at least one modified (e.g., auxotrophic) microorganism. As described herein, in an embodiment the at least one modified microorganism is at least one of responsive or resistant to the at least one antibiotic.

In an embodiment, the at least one modified microorganism is administered directly to the at least one biological tissue where the at least one therapeutic agent is desired. In an embodiment, the at least one modified microorganism is administered indirectly at another location, and the at least one modified microorganism is translocatable to the at least one biological tissue where the at least one therapeutic agent is desired. The translocation can be conferred in a number of ways, including but not limited to homing by the modified microorganism (e.g., adhesion molecules, etc.), or external intervention (e.g., magnetic particles, electrical signaling, etc.). In an embodiment, more than one modified microorganisms are administered to at least one biological tissue where the at least one therapeutic agent is desired, and at least one of the more than one modified microorganisms remains in the at least one biological tissue, while others of the group may translocate to another location or biological tissue. For example, certain recombinant strains of *Lactobacillus* (e.g., *L. reuteri*) are capable of consistently and accurately reaching and adhering to target locations on the mucosa of the host, and expressing heterologous proteins. See, for example, U.S. Pat. No. 6,100,388, which is incorporated herein by reference.

For example, several *Lactobacillus* strains have been shown to translocate from the stomach into the intestinal tract without lysis. See, for example, Grangette, et al, Infect. and Immun. vol. 72, no. 5, pp. 2731-2737 (2004), and Wadolkowski, et al. Infect. and Immun. vol. 56, no. 5, pp. 1030-1035 (1998), each of which is incorporated herein by reference.

In another example, a host microorganism cell that includes a recombinant vaccine virus with a modified thymidine kinase gene and modified hemagglutinin gene allows for directing the microorganism to a particular biological tissue location (e.g., immunoprivileged sites, tumors, etc.) for delivery of particular products. See, for example, U.S. Patent Application No. 20050031643, which is incorporated herein by reference.

In another example, a host microorganism cell (e.g., an anaerobic cell) preferably colonizes avascular compartments of tumors for delivery of anti-tumor products. See, for example, U.S. Pat. No. 7,344,710, which is incorporated herein by reference.

In an embodiment, the at least one therapeutic agent is provided in an effective amount to shorten or terminate the life span of a subject (e.g., insects). For example, published reports indicate that the duration of an insect's life span can be cut in half by placing *Wolbachia* wMelPop in the insect. See, for example, Kambris, et al., Science vol. 326, pp. 134-136 (2009), which is incorporated herein by reference. In an embodiment, *Wolbachia* or another microorganism is utilized with at least one embodiment described hererin, for delivery of at least one therapeutic agent. Thus, in an embodiment, the composition including the modified microorganism is provided to an insect (e.g., fly, mosquito, etc.) in order to control the insect population.

In an embodiment, the method further comprises administering at least one antacid, proton pump inhibitor, alkaline substance, or other substance approximately prior to, during, or subsequent to administering the at least one composition to the at least one biological tissue, particularly in the case of therapeutic agents that are pH dependent. In an embodiment, the method further comprises administering at least one prodrug or precursor compound to the at least one biological tissue. Various prodrugs or precursor compounds are disclosed herein.

In an embodiment, the method further comprises administering at least one antibiotic to the at least one biological tissue prior to, during, or subsequent to administering the at least one auxotrophic microorganism. In an embodiment, the at least one auxotrophic microorganism is responsive to the at least one antibiotic. In an embodiment, the at least one auxotrophic microorganism is resistant to the at least one antibiotic. In an embodiment, the at least one antibiotic includes one or more of ciprofloxacin, penicillin, ampicillin, amikacin, gentamicin, kanamycin, neomycin, netilmicin, streptomycin, tobramycin, paromomycin, geldanamycin, herbimycin, loracarbef, ertapenem, doripenem, imipenem, meropenem, cefadroxil, cefazolin, cefalotin, cefalexin, cometabolite, cefamandole, cefoxitin, cefprozil, cefuroxime, cefixime, cefdinir, cefditoren, cefoperazone, cefotaxime, cefpodoxime, ceftazidime, cefibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, azlocillin, carbenicillin, cloxacillin, dicloxacillin, flucloxacillin, mezlocillin, meticillin, nafcillin, oxacillin, piperacillin, ticarcillin, bacitracin, colistin, polymyxin B, enoxacin, gatifloxacin, levofloxacin, lomefloxacin, moxifloxacin, norfloxacin, ofloxacin, trovafloxacin, grepafloxacin, sparfloxacin, mafenide, prontosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin, rifampicin, thiamphenicol, tridazole, or other antibiotic.

In at least one embodiment, the at least one biological tissue is located at least in one of in vitro, in vivo, in situ, in utero, ex vivo, in planta, or in silico. In an embodiment, the at least one biological tissue includes at least one of one mucosal surface. In an embodiment, the at least one biological tissue includes at least one of cartilage, skin, scalp, hair, nail, nail bed, teeth, eye, ear, ovary, oviduct, tongue, tonsil, adenoid, liver, bone, pancreas, stomach, duct, valve, smooth muscle, appendix, blood vessel, bone marrow, blood, lymph, heart, lung, brain, breast, kidney, bladder, urethra, ureter, gall bladder, uterus, prostate, testes, vas deferens, fallopian tubes, large intestine, small intestine, esophagus, oral cavity, nasal cavity, otic cavity, connective tissue, muscle tissue, adipose tissue, placental tissue, fetal tissue, or mucosa-associated lymphoid tissue (MALT).

In an embodiment, the at least one auxotrophic microorganism is in physical or chemical communication in vitro with one or more cells of the at least one biological tissue prior to in vivo administration of the at least one auxotrophic microorganism to the at least one biological tissue.

In at least one embodiment, the at least one biological tissue is at least partially located in a subject. In an embodiment, a subject includes, but is not limited to, a vertebrate or invertebrate, including a fish, reptile, mammal, amphibian, or bird. In at least one embodiment, the subject includes at least one human. In an embodiment, the at least one subject includes at least one of livestock, pet, zoo animal, undomesticated herd animal, wild animal, aquatic plant or animal, or product animal.

In an embodiment, the at least one subject includes at least one of a sheep, goat, frog, dog, cat, rat, mouse, vermin, monkey, horse, cow, pig, chicken, shellfish, fish, turkey, llama, alpaca, bison, buffalo, ape, primate, ferret, wolf, fox, coyote, deer, rabbit, guinea pig, yak, elephant, tiger, lion, cougar, chinchilla, mink, reindeer, elk, camel, fox, elk, deer, raccoon, donkey, or mule. In an embodiment, the at least one subject includes at least one anthozoan species. In an embodiment, the at least one subject includes at least one of a sea anemone, coral, mollusk, fish, whale, dolphin, porpoise, seal, otter, beaver, seabird, gull, pelican, albatross, duck, swan, or goose. In an embodiment, the at least one subject includes at least one insect (e.g., fly, mosquito, beetle, moth, butterfly, etc.). In an embodiment, the at least one subject includes at least one arachnid. In an embodiment, the at least one subject includes at least one crustacean.

In an embodiment, the subject includes a plant. In an embodiment, the at least one biological tissue includes one or more of a stalk, stem, leaf, root, plant, or tendril. In an embodiment, the at least one biological tissue includes at least one food product. In an embodiment, the at least one food product includes one or more animal, plant, fungal or other food product. In an embodiment, the food product includes meat. In an embodiment, the at least one biological tissue includes at least one cell mass or wound.

In an embodiment, the at least one composition is self-administered by the at least one subject. In an embodiment, the at least one composition is ingestable by the at least one subject. In an embodiment, the at least one composition is ingested by the at least one subject. In an embodiment, the at least one biological tissue includes at least one implantable or transplantable biological tissue. In an embodiment, the at least one biological tissue is transplanted or implanted into at least one subject. In an embodiment, the at least one biological tissue is from at least one donor or recipient. In an embodiment, the at least one biological tissue includes at least one bodily orifice of a subject.

In an embodiment, the subject is afflicted with or suspected of being afflicted with at least one symptom, affliction, disorder, disease or condition. As described herein, the at least one disease or condition may include one or more of a pathogenic infection, parasitic infection, autoimmune disease, sepsis, systemic inflammatory response syndrome, septic shock, multiple organ dysfunction syndrome, allergic reaction, or cancer. In at least one embodiment, the at least one inflammatory disease or condition includes one or more of anaphylaxis, viral infection, bacterial infection, plasmodium infection, protozoan infection, nematode infection, or other worm infection. In at least one embodiment, the at least one inflammatory disease or condition includes malaria. In at least one embodiment, the parasitic infection includes at least one infection or infestation of one or more of a phytoparasite, zooparasite, ectoparasite, endoparasite, or one or more of parasitic cysts, larvae, or eggs.

One embodiment relates to one or more methods of modulating the activity of intracellular signaling molecules. Any of the methods disclosed herein may include detecting in the subject, or tissues, at least one level of at least one biological signaling molecule that is associated with a disease, disorder, or condition described herein.

Detection of one or more of the biological signaling molecules can be by any method known in the art, including but not limited to analyzing one or more biological tissues or fluids from the subject. Analyzing one or more biological fluids can be performed by any of a variety of methods known in the art, including but not limited to utilizing one or more of thin-layer chromatography, mass spectrometry, nuclear magnetic resonance, polymerase chain reaction, reverse transcriptase, Northern blot, Western blot, microscopy, flow cytometry, antibody binding, enzyme-linked immunosorbent assay, radioactive absorption or release, microfluidic analysis, nucleic acid chip array analysis, protein chip array analysis, chemical sensor analysis (including arrays), biosensor analysis, cell counting, or cell sorting.

In at least one embodiment, the at least one biological signaling molecule includes but is not limited to, one or more nucleic acid, amino acid, peptide, polypeptide, protein, glycopeptide, glycoprotein, glycolipid, lipopolysaccharide, peptidoglycan, proteoglycan, lipid, metalloprotein, liposome, or carbohydrate. Carbohydrates may include, but not be limited to, oligosaccharides, glycans, glycosaminoglycans, or derivatives thereof.

In at least one embodiment, the at least one biological signaling molecule includes but is not limited to at least one cytokine, chemokine, cellular receptor, intracellular second messenger, protease, kinase, enzyme, cellular receptor ligand, transcription factor, or hormone.

A treatment regimen may include a therapeutically effective amount of one or more compositions described herein that includes modulators or analogs thereof. The treatment regimen may further include a schedule of changes in the dosage of the composition to maintain a desired level of one or more molecules related to a symptom, affliction, disorder, disease, or condition in one or more biological tissues or subjects. Such treatment may be individualized for the biological tissue or subject.

Treating or treatment that includes administration of at least one of the compositions included herein may prevent or delay the onset of symptoms, complications, or biochemical indicia of a disease, affliction, symptom, condition, or disorder, or alleviate the symptoms, arrest, or inhibit further development of the disease, symptom, affliction, condition, or disorder. Treatment or administration of at least one composition described herein may be prophylactic to prevent or delay the onset of a disease, disorder, symptom, affliction, or condition, or prevent the manifestation of clinical or subclinical symptoms thereof, or therapeutic suppression or alleviation of symptoms after the manifestation of the disease, condition, or disorder.

A treatment regimen may be continuous and uninterrupted, which indicates that there is no break in the treatment regimen during the treatment period. Continuous, uninterrupted administration of a combinational composition includes that the combination may be administered during the entire treatment period, e.g., at least once daily or on a continuous and uninterrupted basis. The treatment regimen may be given to maintain an in vivo therapeutic level or a determined cyclic level of the one or more agents of the at least one composition.

It is expected that the treatment period may vary depending, for example, on the symptoms to be treated. Physician evaluation along with patient interaction will assist in the determination of the duration of treatment. Adjustments in the treatment regimen may depend upon the individual's medical history, or genetic or proteomic information.

At least one embodiment relates to one or more methods based on a genetic or proteomic profile of the subject. In addition, medical evaluation regarding genetic profiling or genetic testing can be provided as a current determination of genetic risk factors, or as part of the subject's medical history. Genetic profiling or genetic testing can be used to design a treatment regimen and thus determine an optimal level individualized for the subject. A physician may use the genetic profile or genetic testing information to determine a genetic basis for needed treatment based on baseline or physiological levels of inflammatory agents.

In an embodiment, the at least one therapeutic agent modulates at least one immune response. In an embodiment, the at least one immune response includes at least one allergic or autoimmune response.

In an embodiment, the at least one therapeutic agent induces apoptosis in one or more cells of the at least one biological tissue (e.g., blood cells, tumor cells, bone cells, etc.). In an embodiment, the at least one therapeutic agent modulates at least one inflammation response. In an embodiment, the at least one therapeutic agent modulates the viability, proliferation, or metastasis of at least one tumor cell.

As set forth herein, the compositions disclosed are formulated by standard practice. In certain instances, in order to account for bioavailability, a formulation may be provided in rapid release, extended release or slow-release form. Likewise, liposomes, microsomes, or other vehicles or composition modifications allow for regulating the dosage by increasing or decreasing the rate of composition delivery, maintenance, decomposition, clearance, or other factors. For example, one particular therapeutic agent may have bioavailability properties that require it to be modified by standard techniques so that it can be administered simultaneously with another therapeutic agent. Similarly, in the instance where multiple therapeutic agents are included in a single composition, it may be necessary to modify one or more of the therapeutic agents by standard techniques.

In at least one embodiment the one or more biological signaling molecules are detected by one or more recognition molecules specific to the one or more biological signaling molecules. The recognition molecules may include, but not be limited to, an antibody, affibody, DNA-recognition molecule, aptamer, or other molecule.

An antibody may include an anti-idiotypic antibody, a heteroantibody, multiple antibodies, one or more antibody fragments, one or more antibody derivatives, one or more antibodies linked together, chimeric antibodies, humanized antibodies, human antibodies, recombinant antibodies, synthetic antibodies, or others.

Antibodies or fragments thereof may be generated against an agent, such as a receptor or ligand, using standard methods, for example, such as those described by Harlow & Lane (*Antibodies: A Laboratory Manual*, Cold Spring Harbor Laboratory Press; $1^{st}$ edition 1988), which is herein incorporated by reference). Alternatively, an antibody fragment directed against an agent may be generated using phage display technology (See, e.g., Kupper, et al. BMC Biotechnology Vol. 5, No. 4, (2005), which is herein incorporated by reference). An antibody or fragment thereof could also be prepared using in silico design (See e.g., Knappik et al., J. Mol. Biol. Vol. 296, pp. 57-86 (2000), which is herein incorporated by reference). In addition or instead of an antibody, the assay may employ another type of recognition element, such as a receptor or ligand binding molecule. Such a recognition element may be a synthetic element like an artificial antibody or other mimetic. (See e.g., U.S. Pat. No. 5,804,563 (Synthetic receptors, libraries and uses thereof), U.S. Pat. No. 6,797,522 (Synthetic receptors), U.S. Pat. No. 6,670,427 (Template-textured materials, methods for the production and use thereof), and U.S. Pat. No. 5,831,012, U.S. Patent Application 20040018508 (Surrogate antibodies and methods of preparation and use thereof); and Ye and Haupt, Anal Bioanal Chem. Vol. 378, pp. 1887-1897, (2004); Peppas and Huang, Pharm Res. Vol. 19, pp. 578-587 (2002), each of which is herein incorporated by reference).

In some instances, levels of particular biological signaling molecules may be assayed in a bodily fluid or tissue using gas or liquid chromatography with or without mass spectrometry.

A bodily fluid may include blood, lymph, saliva, urine, sweat, ascites, serum, urogenital secretion, bone marrow, a tissue secretion or excretion, or other fluid.

A level of one or more biological signaling molecules may also be assayed in a bodily fluid or tissue using a recombinant cell based assay or sensor. A sensor may include, for example a chemical sensor, biosensor, protein array, or microfluidic device.

Prior to determining a treatment regimen, additional information regarding the physiological status of the subject or biological tissue may be gathered and assessed. For example, information may be collected on a subject's medical history or familial history, including genetic or proteomic information. The individualized medical evaluation can include a genetic profile of the subject regarding genes, genetic mutations or genetic polymorphisms that indicate risk factors that affect risk of disease, or disease state. The medical evaluation can include information in a population database on disease risks, available drugs and formulations, documented population responses to drugs and formulations, or condition in relation to any possible therapeutic treatment derived from population databases.

In an embodiment, one or more polymorphisms are determined prior to administration of at least one composition described herein, which could allow for such composition to be tailored to a particular subject's genetic makeup.

A genetic polymorphism or mutation may indicate how a biological tissue or subject will respond to a particular treatment regimen. Genomic DNA used in genetic profiling may be isolated from any biological sample which contains the DNA of that subject or tissue, including but not limited to blood, saliva, cheek swab, epithelium, or other tissue. For example, genomic DNA may be extracted from whole blood or from isolated peripheral blood leukocytes isolated by differential centrifugation from whole blood using a commercial kit (See e.g., QIAmp DNA Blood Mini Kit, Qiagen, Valencia, Calif.) according to the manufacturer's instructions.

Medical evaluation of the subject or tissue for genetic or proteomic profiling or genetic or proteomic testing may be provided as a current determination of genetic risk factors in the subject or tissue, or as part of the subject's medical history. Genetic profiling or genetic testing may be determined by using a variety of methods including but not limited to restriction landmark genomic scanning (RLGS), Southern blot analysis combined with restriction fragment length polymorphism (RFLP), fluorescence in situ hybridization (FISH), enzyme mismatch cleavage (EMC) of nucleic acid heteroduplexes, ligase chain reaction (LCR) or polymerase chain reaction (PCR) based methods. Analysis of one or more single nucleotide polymorphisms (SNPs) may also be used for genetic profiling.

Restriction fragment landmark genomic scanning (RLGS) may be used to scan an entire mammalian genome. As such, genomic DNA is digested with restriction enzymes to generate large DNA fragments. The fragments are separated on an agarose gel, digested with one or more restriction enzymes within the agarose gel, and then separated in a second dimension by polyacrylamide gel electrophoresis (PAGE) (See e.g., Tawata, et al., Comb. Chem. High Throughput Screen. Vol. 3, pp. 1-9 (2000), which is herein incorporated by reference). The DNA may be labeled prior to digestion, or the fragments may be stained nonspecifically as with an intercalating dye, for example. The resulting pattern may be compared with pre-established norms to detect genetic mutations.

Restriction fragment length polymorphism (RFLP) is similar to restriction fragment landmark genomic scanning in that the genomic DNA is digested with specific restriction enzymes and separated on an agarose gel. The separated DNA is transferred to a membrane and the fragments are visualized using hybridization analysis and gene specific probes.

A variety of PCR related methods may be used for genetic profiling and may be used to detect both known and unknown mutations and polymorphisms (See e.g., Tawata, et al., Comb. Chem. High Throughput Screen. Vol. 3, pp. 1-9 (2000), which is herein incorporated by reference). For known mutations and polymorphisms, specific PCR oligonucleotide probes are designed to bind directly to the mutation or polymorphism or proximal to the mutation or polymorphism. For example, PCR may be used in combination with RFLP. In this instance, a DNA fragment or fragments generated by PCR with primers on either side of the mutation or polymorphism site are treated with restriction enzymes and separated by agarose gel electrophoresis. The fragments themselves may be detected using an intercalating dye such as, for example, ethidium bromide. An aberrant banding pattern may be observed if mutations exist within the restriction sites. PAGE may be used to detect single base differences in the size of a fragment.

Alternatively, PCR may be used in combination with DNA sequencing for genetic profiling. For example, PCR primers may be designed that bind to either side of a potential mutation site on the target DNA and generate a PCR fragment that spans a potential mutation site. The PCR fragment is either directly sequenced or subcloned into a cloning vector and subsequently sequenced using standard molecular biology techniques.

Alternatively, a mutation or polymorphism may be screened using comparative genomic hybridization (CGH) (See e.g., Pinkel & Albertson, Nat. Gen. Vol. 37:S11-S17 (2005), which is herein incorporated by reference). In this instance, "normal" genomic DNA and test genomic DNA are differentially labeled and hybridized to metaphase chromosomes or DNA microarrays. The relative hybridization signal at a given location is proportional to the relative copy number of the sequences in the reference and test genomes. Arrays may be generated using DNA obtained from, for example, bacterial artificial chromosomes (BACs) or PCR.

Analysis of one or more single nucleotide polymorphism (SNP) may be used for genetic profiling. A SNP is a DNA sequence variation in which a single nucleotide in the genomic sequence differs between members of a species (or between paired chromosomes of an individual). For a variation to be considered a SNP it must occur in at least 1% of the population. Most SNPs do not affect protein function, and/or are not responsible for a disease state, but they may serve as biological markers for pinpointing an altered protein or disease on the human genome map as they are often located near a gene found to be associated with a certain disease. Occasionally, a SNP may actually affect protein function and/or cause a disease and, therefore, can be used to search for and isolate a specific gene, e.g., a T to C mutation in the CYP17 gene which affects enzyme function. The pattern of SNPs in a subject's genomic DNA may be compared with information in databases in an association study to determine effect on protein function and/or risk of disease development. SNPs may be identified using PCR and DNA sequencing as described above. Alternatively, SNP genotyping may be done using high throughput array analysis (See e.g., Applied Bio-Systems, ABI PRISM, 3100 Genetic Analyzer with 22-cm Capillary Array; Syvanen, et al., Nat. Genet., Vol. 37, pp. S5-S10 (2005) which is herein incorporated by reference). A growing number of web-based databases are available for finding information regarding SNPs and protein function and/o disease associations (See e.g., International HapMap Project on the worldwide web at //snp.cshl.org; Nature 449:

851-861, 2007; National Center Biotechnology Information (NCBI) Single Nucleotide Polymorphisms, on the worldwide web at ncbi.nlm.nih.gov/projects/SNP/, which is herein incorporated by reference).

Methods of Administration of Modified Microorganisms to Environmental Media

In an embodiment, a method of administering at least one environmental medium treatment agent to at least one environmental medium comprises providing at least one composition to at least one environmental medium; wherein the at least one composition includes at least one modified microorganism including at least one heterologous genetic element encoding at least one environmental medium treatment agent; and at least one genetic element inducible to initiate death of the at least one modified microorganism. In an embodiment, the at least one composition includes an effective amount of the at least one environmental medium treatment agent.

As described herein, the effective amount of at least one environmental medium treatment agent is provided in relation to at least one intended outcome. For example, the effective amount of at least one environmental medium treatment agent is provided in relation to establishment or re-establishment of organisms in the at least one environmental medium. In an embodiment, the effective amount of at least one environmental medium treatment agent is provided in relation to revitalization of the at least one environmental medium associated with at least one of fire, flood, contamination, drought, deforestation, temperature change, chemical waste, agricultural waste or run-off, municipal waste, landfill gas or run-off, nuclear waste or run-off, or habitat change.

In an embodiment, the at least one environmental medium treatment agent includes at least one plant growth factor, nutrient, or other compound to the at least one environmental medium. For example, in an embodiment, the at least one environmental medium treatment agent assists in facilitating plant growth, biodegradation of biomass, remediation of contaminated or polluted environmental media, or other outcomes.

In an embodiment, at least one precursor compound is administered to the at least one environmental medium. The precursor compound can be in the form of the at least one environmental medium treatment agent, as described herein, or it can be administered prior to, or during administration of the at least one composition. In an embodiment, the at least one environmental medium treatment agent converts the at least one precursor compound into an active state. In an embodiment, the at least one environmental medium treatment agent translocates to another environmental medium. In an embodiment, the at least one environmental medium treatment agent is formulated to translocate to another environmental medium. In an embodiment, the at least one environmental medium treatment agent remains in the at least one environmental medium to which it is administered. For example, an environmental medium treatment agent administered to a water source (such as a lake or river) can translocate to the surrounding soil by way of osmosis, evaporation, fluid travel, or other mechanism.

In an embodiment, the composition provides an effective amount of at least one environmental medium treatment agent in relation to the at least one intended outcome. For example, the intended outcome includes, but is not limited to, establishment or re-establishment of organisms (e.g., plants, animals, microorganisms) in the at least one environmental medium where the composition is administered. In an embodiment, the environmental medium treatment agent provides an effective amount for revitalization of the environmental medium following destruction associated with at least one of fire, flood, contamination, drought, deforestation, temperature change, or habitat change.

In an embodiment, the method further comprises administering at least one antibiotic to the at least one environmental medium prior to, during, or subsequent to administering the at least one composition. Various antibiotics are described herein.

In an embodiment, the at least one modified microorganism is sensitive or responsive to the at least one antibiotic. In an embodiment, the at least one modified microorganism is resistant to the at least one antibiotic.

In an embodiment, the method further comprises obtaining at least one microorganism associated with the at least one environmental medium, and modifying it to produce the at least one auxotrophic microorganism. In an embodiment, the method further comprises obtaining genetic sequence information from the at least one microorganism. In an embodiment, the method further comprises amplifying the at least one microorganism prior to, during, or subsequent to modifying the at least one microorganism.

In an embodiment, the method further comprises detecting at least one of the presence, amount, concentration, or location of at least one of the at least one modified microorganism, the therapeutic agent or environmental medium treatment agent, or at least one metabolite utilizable by the at least one modified microorganism subsequent to administration of the composition. In an embodiment, the method further comprises selecting for administration an amount or type of composition. In an embodiment, the method further comprises selecting for administration an amount or type of at least one inducer or repressor of the heterologous genetic element encoding at least one environmental medium treatment agent. In an embodiment, the method further comprises selecting for administration an amount or type of at least one of an inducer or repressor of the at least one genetic element inducible to initiate death of the at least one modified microorganism.

In an embodiment, microorganisms are modified to produce at least one therapeutic agent (which may include an agent used as a responsive therapy, or prophylactic therapy, etc.). The modified microorganisms are retained in vivo by administration of at least one required factor as part of the modified microorganism composition.

In an embodiment, the method further comprises administering metabolite subsequent to administration of the composition. As such, if metabolite is administered as part of the initial composition, then the subsequent administration of metabolite will be in addition to the metabolite administered as part of the composition. In embodiments where the metabolite is not administered as part of the initial composition, then the subsequent administration of metabolite will be instead of the earlier administration.

In an embodiment, an oral composition is administered to a subject. In an embodiment, resident microbes are depleted by administering at least one antibiotic prior to, during, or subsequent to administration of the modified microorganism composition. For example, ciproflaxocin dosed at moderate levels for 5 days causes a reduced abundance of about 30% of the bacterial taxa in the human colon. See, for example, Dethlefsen et al, PLoS Biology vol. 6, pp. 2383-2400 (2008), which is incorporated herein by reference. In an embodiment, the modified microorganisms include live, commensal bacteria, archea, fungi, or other microbe given orally. As published, commensal bacteria are able to colonize the intestine following depletion of microorganisms by antibiotic treatment. See, for example, Wadolkowski, et al, Inf. Imm., vol. 56, pp.

1030-1035 (1988); and Rao, et al, PNAS, vol. 102, no. 34, pp. 11993-11998 (2005), each of which are incorporated herein by reference.

In an embodiment, at least one antacid or proton pump inhibitor (e.g. Pantozol, Altana Pharma BV, Hoofdorp, Netherlands) and a chocolate acid binder (e.g. Questran, Zambon, Amersfoort, Netherlands) are administered prior to, during, or subsequent to administration of the modified microorganism composition in order to improve viability during passage through the stomach. See, for example, Braat et al, Clin. Gastroenterol. Hepatol. vol. 4, pp. 754-759 (2006), which is incorporated by reference. For example, a bacterium such as *Eschericia coli* (*E. coli*), Nissile 1917 can be engineered using rDNA methods to produce proteins or peptides. See, for example, Rao et al, Ibid., and U.S. Pat. No. 7,341,860; each of which is incorporated herein by reference.

In an embodiment, the modified microorganism composition requires gene expression for production or delivery of the at least one therapeutic agent. Expression of genes encoding at least one therapeutic agent (e.g., protein, microbicide, antigen, tolerogen, etc.) is directed, for example, by a constitutive or inducible bacterial or other microbial promoter. For example, in an embodiment, the acid inducible P170, P3, or P1 promoter (isolated from *Lactoccus*) can be fused to genes encoding microbicide proteins and gene expression can be induced with low pH. See, for example, Madsen, et al., Ibid.

In an embodiment, the arabinose promoter ($P_{BAD}$) can be fused to heterologous genes encoding therapeutic proteins, or other therapeutic agents. Coexpression of araC, an arabinose operon regulatory protein, and provision of L-arabinose regulates expression of genes fused to the $P_{BAD}$ promoter. See, for example, U.S. Pat. No. 7,341,860, Ibid.

In an embodiment, gene constructs employ a constitutive promoter including, for example, promoter sequences derived from the bacterial thymidine synthase gene which continuously express at least one therapeutic agent, such as a cytokine. See, for example, Steidler et al, Nature Biotechnology vol. 21, pp. 785-789 (2003), which is incorporated herein by reference. For example, gene constructs directing expression of at least one therapeutic agent (e.g. antigenic, microbicidal or tolerogenic protein, etc.) can be incorporated into expression plasmids with drug-resistance selectable markers (e.g. ampicillin resistance marker, β-lactamase, or chloramphenicol resistance marker) and transfected or electroporated into bacteria, or other microbes. See, for example, Sambrook et al, Molecular Cloning: A Laboratory Manual, second ed., Cold Spring Harbor Laboratory Press, N.Y. (1989), which is incorporated by reference herein.

In an embodiment, a propionate inducible expression system is utilized, in order to provide a relatively homogenous expression in individual microorganism cells, and allow for highly regulatable expression. See, for example, Lee and Keasling, App. Env. Microbiol. vol. 71, no. 11, pp. 6856-6862 (2005), which is incorporated herein by reference. For example, expression vector pPro, described by Lee and Keasling, is capable of being regulated at the single cell level over a wide range of inducer concentrations in a dose-dependent manner. Id. Furthermore, since bacterial cells are permeable to the inducer proprionate (which is metabolized by 2-MC by native chromosomal expression), regulatable and consistent induction in all cells of the culture is attainable.

In certain instances, repression is equally important as induction (for example, in instances where the gene product is particularly toxic or difficult to maintain in the host microorganism). Since protein synthesis depends on translational efficiency as well as promoter strength, background expression may be reduced by using a weaker ribosome binding site sequence, or by decreasing the strength of the promoter by introducing nucleotide changes in the consensus promoter sequence (or by variations in the spacer sequence).

In an embodiment, gene constructs that direct protein expression can be integrated into bacterial or other microbial chromosomal DNA by homologous recombination using methods described in Steidler et al, Ibid.

In an embodiment, the modified microorganism is engineered or selected for by utilizing specific nutrient or metabolite requirements. For example deletion of the thymidine synthase gene in *Lactococcus lactis* (*L. Lactis*) by homologous recombination using recombinant DNA plasmids results in *L. lactis* clones that require thymidine for growth. See, for example, Steidler et al, Ibid. Since thymidine is present only at low levels in human colon, *L. lactis* thymidine auxotrophs survive less than two days following oral administration to human volunteers. See, for example, Braat et al, Ibid.

However, thymidine auxotrophs can survive longer than 200 hours in vitro when thymidine (10 μM) is provided in the media. Thus, one can control the growth and survival of thymidine auxotrophs in vivo by dosing and scheduling administration of thymidine prior to, during, or subsequent to administration of the modified microorganism composition. For example, in an embodiment, bacterial (or other microbial) auxotrophs are derived from standard bacterial strains (or other microbial strain) by deleting or mutating genes encoding enzymes or other proteins essential for bacterial (or other microbial) metabolism and growth. Methods for creating mutations, insertions and deletions (such as homologous recombination, recombinant DNA techniques, insertional mutagenesis, targeted gene deletion, etc.) in essential genes are described at, for example, U.S. Pat. No. 5,643,771, and Biswas et al, J. Bacteriology, vol. 175, pp. 3628-3635 (1993); each of which is incorporated herein by reference. For example, mutation or deletion of the β-aspartate semialdehyde dehydrogenase gene (Asd) in bacteria or other microbe precludes synthesis of diaminopimelic acid (DAP), an essential cell wall constituent that is not present in animal tissues. Without exogenous DAP, bacteria or other microbe that have a mutated or deleted Asd gene will undergo cell death and lysis (See, for example, U.S. Pat. No. 7,341,860, Ibid.), but providing DAP by oral administration allows Asd mutants to grow, colonize and survive on mucosal surfaces in vivo.

Measurement of modified microorganisms present in vivo can be done using the quantitative polymerase chain reaction (PCR) and primers specific for the microbial strain and the gene expression construct. For example, in an embodiment, stool samples from subjects given *L. Lactis*, engineered to express human IL-10, is assayed with PCR primers specific for the 16s ribosomal RNA of *L. lactis* and the human IL-10 expression construct (See, for example, Braat et al, Ibid.).

In an embodiment, the number of colony forming units (CFU) of *L. Lactis* is assessed by culturing stool samples on microbiological plates containing selective media. For example, fecal samples are suspended in minimal media and then selected on plates coated with antibodies specific for *L. Lactis*. Next, media containing essential nutrients is overlaid and the bacterial colonies arising are counted to determine the CFU present in the fecal sample (See, for example, Steidler et al, Ibid.). In an embodiment, PCR is conducted with colonies and primers specific for the bacteria or other microorganism, and gene expression construct (e.g. 16s ribosomal RNA and IL-10) to verify the identity of the colonies (See, for example, Braat et al, Ibid.).

In an embodiment, bacteria or other microorganisms are modified to deliver at least one therapeutic agent, while requiring an essential metabolite not usually present in biological tissues of the subject (or present at low concentrations). In vivo provision of essential nutrients or metabolites required by the bacteria, or other microorganisms allows for control of the survival and colonization of the bacterial or other microbial delivery, and allows for regulation of the schedule or dose of the at least one therapeutic agent. For example, thymidine synthase mutants of L. lactis (ThyA− L. Lactis) are dependent on exogenous thymidine for growth in vitro and in vivo.

In an embodiment, in vitro, no viable ThyA− L. Lactis are present after culture 72 hours in rich media devoid of thymidine, but in cultures containing 10 μM thymidine, the microbes survive beyond 200 hours. In vivo, only 4% of ThyA− L. Lactis auxotrophs survive after 4 hours in the mammalian intestine with only endogenous thymidine present (thymidine concentration is less than 0.075 μM in human ileal lavage; See, for example, Steidler et al, Ibid.).

In an embodiment, production of at least one therapeutic agent, for example, IL-10, by bacterial or other microbial auxotrophs are controlled by a constitutive promoter, such as the thymidine synthase promoter. Production of IL-10 depends in part on the growth and survival of the bacterial or other microbial auxotroph.

In an embodiment, an inducible promoter such as the $P_{BAD}$/araC promoter/regulator system (see, for example, U.S. Pat. No. 7,341,860, Ibid.), is used in conjunction with arabinose to regulate the production of IL-10. In an embodiment, production and delivery in situ is regulated by dosing and scheduling of arabinose administration, and by controlling bacterial or other microbe survival and growth through dosing and scheduling of thymidine administration. In an embodiment, the amount of protein delivered can be monitored by immunoassay of fecal samples. For example, human IL-10 derived from feces samples can be measured by enzyme linked immunosorbent assay (ELISA; Steidler et al, Ibid.). ELISA reagents and protocols for numerous cytokines including IL-10 are available, for example, from Invitrogen Corp., Carlsbad, Calif.

In an embodiment the production of a therapeutic agent, such as IL-10 and a suicide factor, such as Rel F, are controlled by a synthetic gene network engineered into a microorganism. For example, oral administration of an inducer molecule controls expression of IL-10. A synthetic gene network responsive to pulses of a metabolite (e.g., arabinose), is utilized, as described in Friedland et al., Science, vol. 324, pp. 1199-1202 (2009), which is incorporated herein by reference. In an embodiment, a gene network is constructed by combining transcriptional and translational regulatory elements. For example in an embodiment, the $P_{BAD}$ promoter, a transactivating noncoding RNA, a cis repressor sequence RNA, and a T7 RNA polymerase gene may be combined in a synthetic gene network to control the expression of multiple proteins as shown by Friedland et al., Ibid. In an embodiment, the regulatory elements cause one particular product to be produced with a first induction event (e.g., exposure to arabinose); a second particular product to be produced with a second induction event; a third particular product to be produced with a third induction event, etc. In this manner, the synthetic system allows for exhibiting the number of induction events that have occurred, or "counting" induction events. Id.

In an embodiment, a therapeutic agent (e.g., IL-10) may be delivered to a patient's intestine by ingestion of modified E. coli containing a plasmid encoding a synthetic gene network that responds to multiple pulses of an inducer molecule (e.g., arabinose) by the production of IL-10. The gene network may also contain suicide genes (e.g. rel F) that will cause cell death when they are expressed. See, for example, U.S. Pat. No. 6,610,529, which is incorporated herein by reference. The frequency and duration of arabinose pulsing determines the expression of genes (and their corresponding proteins) in the gene network, while the dose and schedule of oral arabinose administration determines the timing and duration of expression of the therapeutic agent and suicide gene, IL-10 and rel F, respectively. In an embodiment, synthetic gene networks with optimal pulse intervals of approximately 10-40 minutes and optimal pulse lengths of approximately 20-30 minutes are utilized. In an embodiment, gene networks with optimal pulse intervals and pulse lengths of approximately 2-12 hours are also utilized (see Friedland et al., Ibid.). For example, gene networks encoding IL-10 might require approximately two 10-minute pulses of arabinose separated by an interval of 20 minutes to optimally induce IL-10 expression, but rel F expression and cell death would only ensue following two 2-hour pulses with arabinose separated by 2 hours. In an embodiment, gene networks incorporate multiple inducers (e.g., arabinose, anhydrotetracycline and IPTG), and the expression of multiple genes in the network depends, for example, on the order, length and interval of pulsing with each of the inducers. See, Friedland et al., Ibid.

In an embodiment, microorganisms are modified to include at least one lethal or suicide gene to regulate population growth, and to prevent possible dissemination into the environment (e.g. via feces). For example, in an embodiment, the relF gene is controlled by a regulated promoter such as pLac that is repressed by a regulator protein, LacIq, unless isopropyl β-D-thiogalactoside (IPTG) is provided. To control growth of a modified microbial strain in vivo one can administer IPTG to induce relF expression and cause cell death. Alternatively the rel F gene can be controlled by the arabinose promoter/repressor. In this example expression of relF is regulated by the C2 repressor which, in turn, is regulated by the presence of arabinose. Thus, when arabinose levels are reduced C2 repressor levels decline and relF is expressed leading to bacterial cell death (see, for example, U.S. Pat. No. 6,610,529, which is incorporated herein by reference).

In an embodiment, mutually dependent strains of bacteria that signal via small molecules such as acyl-homoserine lactones (acyl-HSL), are modified to express heterologous target genes only when sufficient numbers of both bacterial strains (and acyl-HSL) are present. See, for example, Brenner et al, PNAS, vol. 104, pp. 17300-17304 (2007), which is incorporated herein by reference. For example, in an embodiment, two E. coli strains, modified to produce specific acyl-HSL, control the expression of target genes for each another.

In an embodiment, target gene expression is controlled by provision of exogenous acyl-homoserine lactone to the individual microbial strains. For example, administration of 3-oxododecanoyl-HSL (3OC12HSL) and butanoyl-HSL (C4HSL) in vivo can be used to control target protein production of E. coli strains engineered to be responsive to specific acyl-HSL molecules (see, for example, Brenner et al, Ibid.). In addition, survival of the engineered bacterial strains can be controlled by acyl-HSL-regulated expression of toxin (ccd B) and antitoxin (ccd A) genes, which cause cell death, or allow survival, respectively. See, for example, Balagadde et al, Mol. Sys. Biol., vol. 4, pp. 1-8 (2008), which is incorporated herein by reference. In an embodiment, the toxin-antitoxin includes at least one of masEF, chpBIK, relBE, yefM-yoeB, dinJ-yaf!, or ecnA-ecnB. See, Engleberg-Kulka, et al., PLOS Genetics, vol. 2, no. 10, 1518-1526 (2006), which is incorporated herein by reference.

Coadministration of multiple bacterial strains that express different target genes can be used to co-deliver multiple therapeutic agents. For example, localized co-expression of IL-10 and transforming growth factor beta by two bacterial strains can provide localized immunoregulatory therapy for inflammatory bowel disease.

In an embodiment, a bacterial strain that expresses an antigen derived from a viral pathogen, for example, E7 antigen from human papilloma virus type 16, is coadministered with a second bacterial strain that produces interleukin-12 (IL-12) to promote immunization. In an embodiment, the two bacterial strains are auxotrophs that are mutually dependent on each other for essential metabolites, such as amino acids or DAP.

In an embodiment, one or both auxotrophic strains are sustained in vivo by administering exogenous metabolites (e.g. histidine, arabinose, DAP, acyl-HSL, thymidine) to the host organism. In an embodiment, expression of the E7 gene and IL-12 is directed by the same or a different promoter. The promoter may be constitutive or inducible. For example, in an embodiment, E7 and IL-12 are fused to the lac operon promoter ($P_{lac}$) which is inducible with IPTG or lactose.

In an embodiment, bacterial or other microbial survival and target protein expression is regulated by administration of the same metabolite. For example, in an embodiment, the $P_{lac}$ promoter is used to regulate expression of a polycistronic transcript (see, for example, Brenner et al, Ibid.) that encodes a target protein and a survival factor. Providing lactose (or IPTG) to a subject hosting the bacterial or other microbial strain will not only sustain survival of the strain but also induce expression of the target protein.

Engineered or modified microorganisms, such as fungi, derived from generally regarded as safe (GRAS) species can be auxotrophic for essential metabolites and express protein encoding genes under the control of regulated promoters. For example, in an embodiment, *Saccharomyces cerevesiae* (*S. cerevesiae*) and *Saccharomyces boulardii* (*S. boulardii*) are GRAS organisms that are mutated and selected (See Abosereh et al, Res. J. Agric. Biol. Sci., vol. 2, pp. 478-482 (2006) which is incorporated by reference herein) to obtain clones that require amino acids (e.g., leucine, tryptophan, lysine, arginine), purines, or pyrimidines (e.g., adenine, thymidine). Growth and survival of yeast auxotrophs in vitro and in vivo is dependent on an essential metabolite (e.g., adenine), and if adenine is not present (or present at low levels) in a subject hosting the strain, then growth of the yeast auxotroph can be regulated by administering adenine to the subject. For example, the dose and schedule of adenine administration can control the proliferation and survival of the yeast adenine auxotrophs.

In an embodiment, yeast or other microbial strains are modified to express at least one therapeutic agent (e.g., protein). In an embodiment, yeast cloning vectors used for protein expression include but are not limited to yeast integrative plasmids, yeast episomal plasmids, and yeast centromeric plasmids that contain selectable markers based on metabolite requirements. In an embodiment, genes used as selectable markers include but are not limited to LEU2, URA3, and HIS3, which encode enzymes needed to biosynthesize leucine, uracil and histidine (for example, yeast vectors for protein expression are described in Glazer et al, Microbial Biotechnology: Fundamentals of Applied Microbiology, $2^{nd}$ edition, Cambridge University Press (2007), which is incorporated herein by reference. In an embodiment, transcription of heterologous genes is directed by a constitutive promoter (e.g., ADH1, TDH3) or a regulated promoter (e.g., GAL1, ADH2, PHO5, CUP-1, etc.).

In an embodiment, an engineered or modified yeast strain that requires two metabolites, for example, leucine and histidine, a selectable marker (e.g. LEU2) provides plasmid stability, while the metabolite (e.g., histidine or leucine) regulates growth and survival of the yeast strain. For example, in an embodiment, engineered *S. boulardii* is used for vaccination, wherein the strain requires leucine and histidine, and produces a heterologous protein. In an embodiment, the heterologous protein includes but is not limited to, hepatitis B surface antigen encoded on a yeast episomal plasmid containing LEU2, and under the control of the ADH1 constitutive promoter. In an embodiment, dosing and scheduling of histidine administration regulates the growth and survival of the engineered *S. boulardi* and, in turn, the production and delivery of hepatitis B surface antigen. In an embodiment, yeast or other microbial strains are engineered to express at least one suicide gene. For example, yeast or other microbe strain transformed with a recombinant plasmid encoding a nuclease (e.g. *Serratia marcescens* nuclease A) under the control of the *S. cerevesiae* ADH2 promoter, undergoes cell death when the nuclease A gene is expressed. Ordinarily, the ADH2 promoter is repressed by glucose, and when glucose levels are depleted, the ADH2 promoter/nuclease A gene is expressed, resulting in cell death. See, for example, Balan et al, Yeast, vol. 22, pp. 203-212 (2005) which is incorporated herein by reference. Thus, in a glucose poor environment (e.g. feces, intestine, soil, etc.) death of the modified yeast or other microorganism strain is induced.

In an embodiment, co-administration of at least two strains of modified auxotrophic microbes is performed, for example, in order to provide essential nutrients to each other. For example, in an embodiment, two yeast (*Saccharomyces cerevesiae*) auxotrophs, one that requires lysine, and a second that requires adenine, are modified or engineered to overproduce adenine and lysine, respectively. Conventional methods, such as mutation, selection and genetic crosses, can be employed to generate the mutants. See, for example, Shou et al, PNAS, vol. 104, pp. 1877-1882 (2007), which is incorporated herein by reference.

In an embodiment, growth of each of the yeast strains is dependent on the other strain to supply an essential metabolite (i.e., adenine or lysine). Coadministration of live yeast strains that are mutually dependent on each other for survival allows prolonged survival and colonization of both strains on mucosal surfaces (e.g. intestinal, vaginal, nasal, oral, bronchial, etc.). In an embodiment, the yeast strains are modified to express enzymes essential for overproduction of adenine and lysine under the control of regulated promoters such as the CUP-1 promoter derived from the metallothionein gene. (See, for example, Glazer et al, Ibid.) In an embodiment, transcription of genes fused to CUP-1 is induced by providing metal ions such as $Cu^{2+}$ and $Zn^{2+}$. For example, $ZnCl_2$ can be given orally to induce expression of $ADE4^{op}$ and $LYS21^{op}$, enzymes that mediate over-production of adenine and lysine, respectively, by modified yeast residing, for example, in the colon (see, for example, Shou et al, Ibid.). Withdrawl of $ZnCl_2$ from the diet lowers $Zn^{2+}$ levels, reduces expression of $ADE4^{op}$ and $LYS21^{op}$, and reduces production of adenine and lysine which, in turn, will lead to death of the engineered yeast strains.

In an embodiment, a microorganism, subh as a bacterial strain, is genetically modified to produce a therapeutic agent, such as an anti-fungal peptide. In an embodiment, the bacterial strain delivers the anti-fungal peptide to at least one biological tissue, such as plant leaves, stems, or roots to prevent the growth, inhibit the growth or reduce the viability of fungal plant pathogens. In an embodiment, the bacterial strain is also modified with an inducible genetic element to cause death of the bacteria when a factor is provided to induce a suicide gene. The composition including the modified microorganism and induction factor, is applied sequentially to the plants, and optionally their environment (e.g., soil or water), by spraying, dusting, or sprinkling the composition.

For example, bacteria known to inhabit the phylloplane (the surface of plant leaves) or the rhizosphere (the soil surrounding plant roots) may be used as microbial hosts for plasmid expression vectors directing the expression of an anti-fungal peptide. For example, *Pseudomonas fluorescens* strain SBW25 inhabits the leaves and roots of sugar beet plants and is competent for transformation with recombinant DNA plasmids. See, for example, Zhang, et al., Microbiol. vol. 152, pp. 1867-1875 (2006), which is incorporated herein by reference. In an embodiment, *P. fluorescens* may be transformed with a DNA plasmid that encodes an anti-microbial peptide or toxin and directs expression of the anti-microbial peptide or toxin. See, for example, U.S. Pat. No. 5,017,373; and U.S. Pat. No. 7,510,852, each of which is incorporated herein by reference.

In one example, a recombinant DNA plasmid encoding an antifungal peptide, PW2, and methods for its cloning and construction are described in U.S. Pat. No. 7,550,558, which is incorporated herein by reference. As indicated in the patent, peptide PW2 has anti-fungal activity against the following plant fungal pathogens: *Colletotrichum gossypii, Cephalosporioides, Alternaria macrospora, Colletotrichum ora, Bipolaris sorokiniana, Dreschslera tritici, Phoma sorghina, Pyricularia grisea, Colletotrichum, Gloeosporioides, Rhizoctonia solani* and *Fusarium solani*.

In an embodiment, genetically modified *P. fluorescens* are further modified to contain a suicide gene that may be induced at any time by providing a factor to the *P. fluorescens*, thus killing the bacteria, and stopping the production of the anti-fungal peptide In an embodiment, expression of gene(s) encoding the AlsS and AlsD enzymes is directed by at least one constitutive or inducible bacterial promoter. For example, in an embodiment, the inducible lac operon promoter is fused to at least one gene encoding at least one enzyme (e.g. AlsS, AlsD), and gene expression is induced with lactose or isopropyl β-D-thiogalactoside. See, for example, Rao, et al, PNAS USA vol. 102, no. 34, pp. 11993-11998 (2005), which is incorporated herein by reference.

In an embodiment, the arabinose promoter (pBAD) is fused to the at least one heterologous genetic element. For example, coexpression of araC, an arabinose operon regulatory protein, and providing L-arabinose regulates expression of genes fused to the pBAD promoter. See, for example, U.S. Pat. No. 7,341,860, which is incorporated herein by reference. In an embodiment, at least one heterologous genetic element employs at least one constitutive promoter, for example, at least one promoter sequence derived from the bacterial thymidine synthase gene is used to continuously express at least one enzyme or plant peptide hormone. See, Steidler et al, Nat. Biotech. vol. 21, pp. 785-789 (2003), which is incorporated herein by reference.

In an embodiment, the at least one heterologous genetic element directing expression of the at least one enzyme or plant peptide hormone is incorporated in at least one expression plasmid, or other vector. In an embodiment, the at least one expression plasmid, or other vector, includes at least one drug-resistance selectable marker (e.g. ampicillin resistance marker, β-lactamase, or chloramphenicol resistance marker). In an embodiment, the at least one expression plasmid or other vector is transfected or electroporated into at least one microorganism. Routine methods for gene transfer and components relating to selectable markers are described, for example, in Sambrook et al, Molecular Cloning: A Laboratory Manual, second ed., Cold Spring Harbor Laboratory Press, N.Y. (1989), which is incorporated herein by reference).

In an embodiment, the at least one heterologous genetic element that directs protein expression can be integrated into microorganism chromosomal DNA by homologous recombination by using standard procedures, for example, as described in Steidler et al, Ibid.

In an embodiment, the modified microorganism described herein, e.g. S lividans, is additionally transformed with at least one genetic element inducible to initiate death in the at least one modified microorganism. For example, in an embodiment, the at least one inducible genetic element encodes at least one lethal or suicide gene under the control of an inducible promoter. For example, bacteria may be engineered with the rel F gene to provide additional containment of the modified bacteria. In an embodiment, expression of the relF gene is controlled by an inducible promoter, such as pLac, that is repressed by an inducer, LacIq, unless isopropyl β-D-thiogalactoside (IPTG) is provided (see Rao et al, Ibid.). For example, in order to initiate death in the at least one modified microorganism, IPTG is administered to induce relF expression and cause cell death of the microorganism. In an embodiment, the rel F gene is expressed under the control of the arabinose promoter/repressor system. For example, in an embodiment, expression of relF is regulated by the C2 repressor which, in turn, is regulated by the presence of arabinose. When arabinose levels are reduced, C2 repressor levels decline and relF is expressed leading to microorganism cell death. See, for example, U.S. Pat. No. 6,610,529, which is incorporated herein by reference.

In an embodiment, modified S. lividans bacteria capable of producing acetoin are administered to at least one environmental medium. For example, in an embodiment, the at least one modified microorganism is sprayed onto soil as a spore suspension in water at a rate of approximately $10^6$-$10^8$ colony forming units (CFU) per gram of soil. For example, as shown by published studies, modified S. lividans innoculated at approximately $10^7$ CFU/gm soil and grown at 25° C. survive for at least approximately 90 days. See, for example, Crawford et al, Appl. Envir. Microbiol., vol. 59, pp. 508-518 (1993), which is incorporated herein by reference. In an embodiment, the survival of S. lividans is measured by diluting in water and spreading on plates containing at least one antibiotic to which the microorganism has been rendered resistant. For example, S. lividans strain TK23 is modified to be resistant to spectinomycin, while S. lividans transformed with the plasmid, pIJ702 is resistant to thiostrepton. See, for example, Crawford et al, Ibid.

In an embodiment, a method includes administering at least one composition including at least one modifiec microorganism encoding at least one environmental medium treatment agent, such as a plant peptide hormone, to at least one environmental medium (e.g., soil, water, etc.). In an embodiment, the at least one modified microorganism includes at least one inducible genetic element to initiate death of the at least one modified microorganism.

In an embodiment, the at least one modified microorganism encodes at least one plant peptide hormone (e.g., POLARIS), and at least one genetic element inducible to initiate death in the at least one modified microorganism (e.g., suicide factor, such as rel F), and each is controlled by a synthetic gene network of the microorganism. As shown in published studies, application of an inducer molecule regulates expression of POLARIS, a 36 amino acid peptide that functions in root growth and leaf vascularization. See, for example, Casson et al, Plant Cell, vol. 14, pp. 1705-1721 (2002), which is incorporated herein by reference. In an embodiment, the synthetic gene network is responsive to pulses of a metabolite (e.g., arabinose). See, for example, Friedland et al., Science, vol. 324, pp. 1199-1202 (2009), which is incorporated herein by reference.

In an embodiment, the gene network is constructed by combining transcriptional and translational regulatory elements. For example, in an embodiment, the pBAD promoter, a transactivating noncoding RNA, a cis repressor sequence RNA, and a T7 RNA polymerase gene are combined in a synthetic gene network to control the expression of multiple proteins as shown by Friedland et al., Ibid.

In an embodiment, at least one modified microorganism (e.g. Pseudomonas putida) including at least one heterologous genetic element encoding at least one environmental medium treatment agent, for example, a plant peptide hormone (e.g., POLARIS), to at least one environmental medium (e.g., soil, water, food products). In an embodiment, the at least one modified microorganism includes at least one plasmid encoding a synthetic gene network that responds to multiple pulses of an inducer molecule (e.g., arabinose, acid, etc.), by producing the at least one environmental medium treatment agent (e.g., POLARIS). The gene network further includes at least one genetic element inducible to initiate death in the at least one modified microorganism (e.g., a suicide gene, such as rel F), that induces bacterial cell death when it is expressed. See, for example, U.S. Pat. No. 6,610, 529, which is incorporated herein by reference.

In an embodiment, the frequency or duration of arabinose application determines the expression of the inducible genetic element (and the corresponding protein(s)) in the gene network, and the dose and schedule of arabinose application to the soil, or other environmental medium, determines the timing and duration of expression of POLARIS and rel F. As published, synthetic gene networks have optimal pulse intervals of approximately 10-40 minutes and optimal pulse lengths of approximately 20-30 minutes. Id. In an embodiment, gene networks with optimal pulse intervals and pulse lengths of approximately 2-12 hours are also described. Id. Other optimal pulse intervals can be determined for a particular system, according to the published guidelines. Id.

In an embodiment, a gene networks incorporates multiple inducers (e.g., arabinose, anhydrotetracycline and IPTG), and the expression of multiple genes in the network depends on the order, length, and interval of pulsing with each of the inducers. Id.

In an embodiment, at least one modified microorganism including at least one heterologous genetic element encoding at least one environmental medium treatment agent for the at least one environmental medium includes a substrate-regulated suicide gene system that responds to at least one environmental inducer, such as a xenobiotic or pollutant. For example, in an embodiment, the at least one modified microorganism includes three genetic elements: 1) a regulated promoter (e.g., pLac) fused to a suicide gene (e.g., gef), and 2) a TOL plasmid promoter (e.g., Pm) fused to the lad gene (encoding the Lac repressor), and 3) xylS2, a gene encoding a positive regulator of Pm that interacts with 3-methyl benzoate. See, for example, Ramos, et al., Biotech. vol. 12, pp. 1349-1356 (1994), which is incorporated herein by reference. In an embodiment, soil bacteria, for example, *P. putida*, modified to produce POLARIS under the control of a constitutive promoter (for example, the bacterial thymidine synthase promoter, according to Steidler et al, Ibid.) is transformed with a DNA cassette containing the pLac promoter fused to the gef gene and with a plasmid that contains the Pm promoter fused to lac I gene and encoding the xylS2 positive regulator of Pm. For example, genetic constructs and construction of recombinant bacterial strains can be performed utilizing routine procedures, some of which are described in Jensen et al, Appl. Env. Micro., vol. 59, pp. 3713-3717 (1993), which is incorporated herein by reference. In an embodiment, modified *P. putida* encoding POLARIS, and including at least one genetic element inducible to initiate death of the at least one microorganism, is grown in the presence of 3-methylbenzoate. In an embodiment, when 3-methylbenzoate is combined with the xylS2 gene product, positive regulation of Pm results, and leads to production of the Lac repressor which, in turn, represses the expression of the toxic gene, gef. According to published studies, *P. putida* strains including a substrate-regulated toxic gene system inoculated at approximately $10^6$ CFU/gm to nonsterile soil containing 0.08% (wt/vol.) 3-methyl benzoate are present at approximately $10^8$ CFU/gm of soil after approximately 14 days. See, for example, Jensen et al, Ibid. However, in control experiments without 3-methyl benzoate only approximately $10^2$ CFU/gm of soil survived after 14 days. Id.

Delivery Devices

In an embodiment, a delivery device comprising a composition described herein are disclosed. As indicated in FIG. 5, a delivery device 500 comprises a housing 505 including at least one reservoir containing at least one composition, the at least one composition including at least one first constituent including at least one auxotrophic microorganism including at least one pH inducible promoter operably coupled to at least one heterologous genetic element encoding at least one therapeutic agent, and at least one genetic element inducible to initiate death of the at least one auxotrophic microorganism; and 515 at least one second constituent including at least one metabolite required by the at least one auxotrophic microorganism; the reservoir 520 configured to receive, retain, and dispense at least a portion of the at least one composition; and at least one component 530 configured to administer the at least one composition to at least one biological tissue.

As indicated in FIG. 6, in an embodiment 600, the at least one composition further includes at least one pharmaceutically-acceptable carrier or excipient. In an embodiment 610, the at least one first constituent of the composition and the at least one second constituent of the composition are located in different reservoirs of the delivery device. In an embodiment 620, the device is implantable. In an embodiment 630, the device is implanted into a subject. In an embodiment 640, the device is external to a subject. In an embodiment 650, the device includes at least one component configured to administer the at least one composition to at least one biological tissue includes one or more ports. In an embodiment 660, the at least one of the one or more ports includes at least one outlet port or at least one inlet port. In an embodiment 670, each reservoir includes at least one separate port. In an embodiment 680, the delivery device includes at least one reservoir including at least one inducer formulated to induce at least one promoter operably coupled to the at least one genetic element inducible to initiate death of the at least one auxotrophic microorganism.

As indicated in FIG. 7, the delivery device further comprises 700 one or more controllable output mechanisms operably linked to the one or more ports to control dispensing of at least a portion of the at least one composition from the at least one reservoir. In an embodiment 710, the at least one controllable output mechanism includes at least one of a micropump, valve, or actuator. In an embodiment 720, the valve includes at least one of a one-way valve, or pressure settable valve. In an embodiment 730, the actuator includes at least one of a piezoelectric actuator, electrostatic actuator, thermal actuator, shape-memory alloy actuator, bioactuator, or magnetic actuator. In an embodiment 740, the at least one controllable output mechanism includes at least one thermal or nonthermal gate in communication with the at least one outlet of the at least one reservoir. In an embodiment 750, the delivery device further comprises at least one control circuitry configured to control the at least one controllable output mechanism. In an embodiment 760, the at least one control circuitry is configured to control the release of the at least two constituents of the composition. In an embodiment 770, the at least one of the rate of release, amount of release, or time of release of the at least two constituents of the composition are different for each constituent. In an embodiment 780, the at least one control circuitry is configured to generate and transmit an electromagnetic control signal configured to control the at least one controllable output mechanism. In an embodiment 790, the at least one control circuitry is configured to control the at least one controllable output mechanism for time-release of at least a portion of the at least one composition from the at least one reservoir.

As indicated in FIG. 8, in an embodiment 800, the at least one control circuitry is configured for variable programming control of the at least one controllable output mechanism. In an embodiment 810, the at least one control circuitry is configured to control release of the composition or a portion thereof in response to a signal from a sensor. In an embodiment 815, the at least one control circuitry is configured to control release of at least a portion of the composition in response to a signal from a sensor. In an embodiment 820, the at least one control circuitry is configured to control release of at least one inducer formulated to activate at least one promoter operably coupled to the at least one genetic element inducible to initiate death of the at least one auxotrophic microorganism. In an embodiment 830, the delivery device further comprises at least one injector. In an embodiment 840, the delivery device further comprises at least one transducer. In an embodiment 850, the delivery device further comprises at least one receiver. In an embodiment 860, the at least one receiver is configured to receive information from at least one distal or remote sensor. In an embodiment 870, the receiver is configured to obtain release instructions or authorization to release the at least one composition. In an embodiment 875, the receiver is configured to receive programming instructions or data for the controller. In an embodiment 880, the delivery device further comprises at least one transmitter. In an embodiment 885, the at least one transmitter is configured to transmit information regarding one or more of the date, time, presence or approximate quantity of one or more of at least a portion of the at least one composition, at least one constituent thereof, or at least one product thereof; at least one cell or substance associated with the at least one biological tissue; at least one metabolite associated with the at least one biological tissue; or at least one microorganism associated with the at least one biological tissue. In an embodiment 890, the delivery device further comprises at least one circuit.

As indicated in FIG. 9, in an embodiment 900, the delivery device further comprises at least one power source. In an embodiment 910, the delivery device further comprises at least one detection material. In an embodiment 915, the delivery device further comprises at least one reservoir for controlled release of the at least one detection material. In an embodiment 920, the at least one detection material includes at least one of a radioactive, luminescent, colorimetric or odorous substance. In an embodiment 930, the at least one detection material includes at least one of a taggant, contrast agent, sensor, or electronic identification device. In an embodiment 940, the at least one electronic identification device includes at least one radio frequency idientification device. In an embodiment 950, the at least one sensor includes at least one biosensor. In an embodiment 960, the at least one biosensor includes at least one modified microorganism. In an embodiment 970, the at least one sensor receives information associated with at least one of temperature, pH, inflammation, presence of at least one inducer, amount of at least one inducer, presence of at least one repressor, amount of at least one repressor, or biological response to the at least one composition. In an embodiment 980, the at least one detection material includes at least one of a diamagnetic particle, ferromagnetic particle, paramagnetic particle, super paramagnetic particle, particle with altered isotope, or other magnetic particle. In an embodiment 990, the at least one detection material is responsive to the presence of at least one of the at least one composition, at least one constituent thereof, or at least one product thereof; at least one cell or substance associated with the at least one biological tissue; the at least one metabolite, or at least one product thereof, or the at least one therapeutic agent, or a by-product thereof.

As indicated in FIG. 10, in an embodiment 1000, the at least one detection material is responsive to the approximate quantity of at least one of the at least one composition, at least one constituent thereof, or at least one product thereof; at least one cell or substance associated with the at least one biological tissue; or the at least one metabolite, or at least one product thereof. In an embodiment 1010, the at least one detection material is responsive to the approximate number of microorganisms producing the at least one therapeutic agent. In an embodiment 1020, the at least one detection material is responsive to at least one of: enzyme, acid, amino acid, peptide, polypeptide, protein, oligonucleotide, nucleic acid, ribo- nucleic acid, oligosaccharide, polysaccharide, glycopeptide, glycolipid, lipoprotein, sphingolipid, glycosphingolipid, glycoprotein, peptidoglycan, lipid, carbohydrate, metalloprotein, proteoglycan, chromosome, adhesion molecule, cytokine, chemokine, immunoglobulin, antibody, antigen, platelet, extracellular matrix, blood plasma, cell wall, hormone, organic compound, inorganic compound, salt, or cell ligand. In an embodiment 1030, the at least one detection material is responsive to at least one of: glucose, lactate, urea, uric acid, glycogen, oxygen, carbon dioxide, carbon monoxide, ketone, nitric oxide, nitrous oxide, alcohol, alkaloid, opioid, cannabinol, endorphin, epinephrine, dopamine, serotonin, nicotine, amphetamine, methamphetamine, anabolic steroid, hydrocodone, hemoglobin, heparin, clotting metabolite, tumor antigen, pH, albumin, ATP, NADH, $FADH_2$, pyruvate, sulfur, mercury, lead, creatinine, cholesterol, alpha-fetoprotein, chorionic gonadotropin, estrogen, progesterone, testosterone, thyroxine, melatonin, calcitonin, antimullerian hormone, adiponectin, angiotensin, cholecystokinin, corticotrophin-releasing hormone, erythropoietin, bilirubin, creatine, follicle-stimulating hormone, gastrin, ghrelin, glucagon, gonadotropin-releasing hormone, inhibin, growth hormone, growth hormone-releasing hormone, insulin, human placental lactogen, oxytocin, orexin, luteinizing hormone, leptin, prolactin, somatostatin, thrombopoietin, cortisol, aldosterone, estradiol, estriol, estrone, leukotriene, brain natriuretic peptide, neuropeptide Y, histamine, vitamin, mineral, endothelin, renin, enkephalin, DHEA, DHT, alloisoleucine, toxic substance, illegal substance, therapeutic agent, or any metabolite thereof.

As indicated in FIG. 11, in an embodiment 1100, the delivery device further comprises at least one memory mechanism for storing instructions for generating and transmitting an electromagnetic control signal. In an embodiment 1110, the delivery device further comprises at least one imaging apparatus capable of imaging the approximate quantity within a treatment region of one or more of the at least one composition, at least one constituent thereof, or at least one product thereof; at least one cell or substance associated with the at least one biological tissue; or the at least one metabolite, or at least one product thereof. In an embodiment 1120, the delivery device further comprises at least one reservoir for controlled release of at least one inducer or repressor of the at least one heterologous genetic element encoding at least one therapeutic agent. In an embodiment 1130, the delivery device further comprises at least one reservoir for controlled release of at least one inducer or repressor of the at least one genetic element inducible to initiate death of the at least one modified microorganism. In an embodiment 1140, the delivery device further comprises at least one memory location for recording information. In an embodiment 1150, the at least one memory location is configured to record information regarding at least one sensor. In an embodiment 1160, the at least one memory location is configured to record information regarding at least one of a sensed condition, history, or performance of the device. In an embodiment 1170, the at least one memory location is configured to record information regarding one or more of the date, time, presence or approximate quantity of at least one of the administered composition, constituent thereof, or product thereof; the at least one administered metabolite, or product thereof; or at least one cell or substance associated with the at least one biological tissue.

As indicated in FIG. 12, in an embodiment 1200, the at least one cell or substance associated with the at least one biological tissue includes at least one of an organic or inorganic small molecule, nucleic acid, amino acid, peptide, polypeptide, protein, glycopeptide, glycoprotein, glycolipid, lipopolysaccharide, peptidoglycan, proteoglycan, lipid, lipoprotein, sphingolipid, glycospingolipid, metalloprotein, metal, liposome, chromosome, nucleus, acid, base, buffer, protic solvent, aprotic solvent, carbohydrate, energy, arabinose, lactose, maltose, sucrose, glucose, xylose, xylan, nisin, L-arabinose, allolactose, D-glucose, D-xylose, D-galactose, ampicillin, tetracycline, penicillin, pristinamycin, retinoic acid, interferon, galactose, rhamnose, fructose, melibiose, starch, inunlin, lipopolysaccharide, arsenic, cadmium, hydrocarbon, chromium, mercury, antibiotic, oxygen, carbon dioxide, carbon monoxide, nitrogen, nitric oxide, vitamin, mineral, nitrous oxide, nitric oxide synthase, sulfur, gas, cytokine, chemokine, immunoglobulin, antibody, antigen, extracellular matrix, cell ligand, zwitterionic material, cationic material, oligonucleotide, nanotube, piloxymer, transfersome, gas, element, contaminant, radioactive particle, hormone, virus, enzyme, oligonucleotide, ribonucleic acid, oligosaccharide, polysaccharide, adhesion molecule, platelet, blood plasma, whole blood, cell wall, salt, cell ligand, lactate, urea, uric acid, glycogen, ketone, alcohol, alkaloid, opioid, cannabinol, endorphin, epinephrine, dopamine, serotonin, nicotine, amphetamine, methamphetamine, anabolic steroid, hydrocodone, hemoglobin, heparin, clotting metabolite, tumor antigen, pH, albumin, ATP, NADH, $FADH_2$, pyruvate, mercury, lead, creatinine, cholesterol, alpha-fetoprotein, chorionic gonadotropin, estrogen, progesterone, testosterone, thyroxine, melatonin, calcitonin, antimullerian hormone, adiponectin, angiotensin, cholecystokinin, corticotrophin-releasing hormone, erythropoietin, bilirubin, creatine, follicle-stimulating hormone, gastrin, ghrelin, glucagon, gonadotropin-releasing hormone, inhibin, growth hormone, growth hormone-releasing hormone, insulin, human placental lactogen, oxytocin, orexin, luteinizing hormone, leptin, prolactin, somatostatin, thrombopoietin, cortisol, aldosterone, estradiol, estriol, estrone, leukotriene, brain natriuretic peptide, neuropeptide Y, histamine, vitamin, mineral, endothelin, renin, enkephalin, DHEA, DHT, alloisoleucine, toxic substance, illegal substance, agent, hydrocarbon, arsenic, gold, silver, cadmium, strontium, mercury, lead, other heavy metals, chromium, antibiotic, gas, or any byproducts thereof, plant cell, animal cell, fungal cell, blood cell, muscle cell, nerve cell, fibroblast, adipose cell, stem cell, pluripotent cell, epithelial cell, skin cell, neoplastic cell, tumor cell, cell mass, or other biological tissue or organ cell.

As indicated in FIG. 13, in an embodiment 1300, the delivery device further comprises at least one information transmission mechanism configured to transmit information recorded by the at least one electronic memory location. In an embodiment 1310, the device is located in or is substantially in the form of one or more of a spray apparatus, pump apparatus, bioreactor, or drilling apparatus. In an embodiment 1320, the device is located in or is substantially in the form of one or more of a patch, oral inhaler, nasal spray or other orifice spray, orifice insert, chewing gum, iontophoretic apparatus, oral consumable, ocular or otic dropper or spray, stent, shunt, consumer product, food product, food package, lip balm, lotion, ointment, sunscreen or sunblock, perfume, aftershave, shampoo or other hair products, nail polish, dentures or other oral implants, contact lens or other ocular implants, orifice insert, orifice spray or inhaler, sutures, surgical staples, dental floss, stents, shunts, bandages, absorbable mesh, or oral consumable. In an embodiment 1330, the delivery device further comprises at least one reservoir for controlled release of at least one inducer or repressor of the at least one heterologous genetic element encoding at least one therapeutic agent. In an embodiment 1340, the delivery device further comprises at least one reservoir for controlled release of at least one inducer or repressor of the at least one genetic element inducible to initiate death of the at least one modified microorganism. In an embodiment 1350, the delivery device further comprises a controller configured to respond to the at least one sensor. In an embodiment 1360, the at least one sensor is configured to sense information related to at least one of the at least one biological tissue, the therapeutic agent, or the composition or a consitutuent thereof. In an embodiment 1370, the information related to the at least one biological tissue includes at least one of temperature, pH, inflammation, or other characteristic.

As indicated in FIG. 14, in an embodiment, a delivery device 1400 comprises a housing 1410 including at least one reservoir containing at least one composition, the at least one composition including at least one modified microorganism including at least one heterologous genetic element encoding at least one environmental medium treatment agent, and at least one genetic element inducible to initiate death of the at least one modified microorganism; the reservoir 1420 configured to receive, retain, and dispense at least a portion of the at least one composition, and at least one component 1430 configured to administer the at least one composition to at least one environmental medium.

As indicated in FIG. 15, in an embodiment 1500, at least one composition further comprises at least one metabolite required by the at least one modified microorganism. In an embodiment 1510, the device including at least one component configured to administer the at least one composition to at least one environmental medium includes one or more ports. In an embodiment 1520, the at least one of the one or more ports includes at least one outlet port or at least one inlet port. In an embodiment 1530, each reservoir includes at least one separate port. In an embodiment 1535, the delivery device includes at least one reservoir including at least one inducer formulated to induce at least one promoter operably coupled to the at least one genetic element inducible to initiate death of the at least one auxotrophic microorganism. In an embodiment 1538, the delivery device further comprises one or more controllable output mechanisms operably linked to the one or more ports to control dispensing of at least a portion of the at least one composition from the at least one reservoir. In an embodiment 1540, the at least one controllable output mechanism includes at least one of a micropump, valve, injector, or actuator. In an embodiment 1550, the valve includes at least one of a one-way valve, or pressure settable valve. In an embodiment 1560, the actuator includes at least one of a piezoelectric actuator, electrostatic actuator, thermal actuator, shape-memory alloy actuator, bioactuator, or magnetic actuator. In an embodiment 1570, the at least one controllable output mechanism includes at least one thermal or nonthermal gate in communication with the at least one outlet of the at least one reservoir. In an embodiment 1580, the delivery device further comprises at least one control circuitry configured to control the at least one controllable output mechanism.

As indicated in FIG. 16, in an embodiment 1600, the at least one control circuitry is configured to control the at least one controllable output mechanism for time-release of at least a portion of the at least one composition from the at least one reservoir. In an embodiment 1610, the at least one control circuitry is configured for variable programming control of the at least one controllable output mechanism. In an embodiment 1620, the at least one control circuitry is configured to control the release of at least a portion of the composition. In an embodiment 1625, the at least one control circuitry is configured to control the release of at least a portion of the composition in response to a signal from a sensor. In an embodiment 1628, the at least one control circuitry is configured to control release of at least one inducer formulated to activate att least one promoter operably coupled to the at least one genetic element inducible to initiate death of the at least one modified microorganism. In an embodinient 1630, the delivery device further comprises at least one reservoir for controlled release of at least one inducer or repressor of the at least one heterologous genetic element encoding at least one environmental medium treatment agent. In an embodiment 1650, the delivery device further comprises at least one transducer. In an embodiment 1660, the delivery device further comprises at least one receiver. In an embodiment 1670, the at least one receiver is configured to obtain release instructions or authorization to release the at least one composition. In an embodiment 1680, the receiver is configured to receive programming instructions or data for the controller. In an embodiment 1685, the receiver is configured to receive information from at least one distal or remote sensor. In an embodiment 1690, the delivery device further comprises at least one transmitter.

As indicated in FIG. 17, in an embodiment 1700, the at least one transmitter is configured to transmit information regarding one or more of the date, time, presence or approximate quantity of one or more of the at least one composition, at least one constituent thereof, or at least one product thereof; at least one cell or substance associated with at least one environmental medium; at least one metabolite associated with the at least one environmental medium; or at least one organism associated with the at least one environmental medium. In an embodiment 1710, the delivery device includes at least one reservoir including at least one inducer formulated to induce at least one promoter operably coupled to the at least one genetic element inducible to initiate death of the at least one modified microorganism. In an embodiment 1720, the delivery device further comprises at least one power source. In an embodiment 1730, the delivery device further comprises at least one detection material. In an embodiment 1740, the delivery device further comprises at least one reservoir for controlled release of the at least one detection material. In an embodiment 1750, the at least one detection material includes at least one of a taggant, contrast agent, sensor, or electronic idenfication device. In an embodiment 1760, the at least one electronic identification device includes at least one radio frequency identification device. In an embodiment 1770, wherein the at least one sensor includes at least one biosensor. In an embodiment 1780, the at least one biosensor includes at least one modified microorganism. In an embodiment 1790, the at least one sensor receives information associated with at least one of temperature, pH, presence of at least one inducer, amount of at least one inducer, presence of at least one repressor, amount of at least one repressor, or environmental response to administration of the at least one composition.

As indicated in FIG. 18, in an embodiment 1800, wherein the at least one sensor is configured to sense information related to at least one of the environmental medium, the environmental treatment medium agent, or the composition or a constituent thereof. In an embodiment 1810, the information related to the at least one environmental medium includes at least one of temperature, pH, soil content, water content, mineral content, organic or inorganic matter content, or other characteristic. In an embodiment 1820, the delivery device further comprises a controller configured to respond to the at least one sensor. In an embodiment 1830, the at least one detection material includes at least one of a radioactive, luminescent, colorimetric or odorous substance. In an embodiment 1840, the at least one detection material includes at least one of a diamagnetic particle, ferromagnetic particle, paramagnetic particle, super paramagnetic particle, particle with altered isotope, or other magnetic particle. In an embodiment 1850, the at least one detection material is responsive to the presence of at least one of the at least one composition, at least one constituent thereof, or at least one product thereof; at least one cell or substance associated with the at least one environmental medium; at least one metabolite associated with the environmental medium; or at least one organism associated with the at least one environmental medium. In an embodiment 1860, the at least one organism associated with the at least one environmental medium includes at least one of a plant, animal, fungus, or microorganism. In an embodiment 1870, the at least one detection material is responsive to the approximate quantity of one or more of the at least one composition, at least one constituent thereof, or at least one product thereof; at least one cell or substance associated with the at least one environmental medium; at least one metabolite associated with the at least one environmental medium; or at least one organism associated with the at least one environmental medium.

As indicated in FIG. 19, in an embodiment 1900, the at least one organism associated with the at least one environmental medium includes at least one of a plant, animal, fungus, or microorganism. In an embodiment 1910, the at least one detection material is responsive to the approximate number of microorganisms producing the at least one treatment agent, or an environmental medium substance. In an embodiment 1920, the environmental medium substance includes one or more of an enzyme, acid, amino acid, peptide, polypeptide, protein, oligonucleotide, nucleic acid, ribonucleic acid, oligosaccharide, polysaccharide, glycopeptide, glycolipid, lipoprotein, sphingolipid, glycosphingolipid, glycoprotein, peptidoglycan, lipid, carbohydrate, metalloprotein, proteoglycan, chromosome, adhesion molecule, cytokine, chemokine, immunoglobulin, antibody, antigen, extracellular matrix, cell wall, hormone, organic compound, inorganic compound, salt, cell ligand, glucose, lactate, urea, uric acid, glycogen, oxygen, carbon dioxide, carbon monoxide, ketone, nitric oxide, nitrous oxide, alcohol, alkaloid, opioid, cannabinol, endorphin, epinephrine, dopamine, serotonin, nicotine, amphetamine, methamphetamine, pH, albumin, ATP, NADH, $FADH_2$, pyruvate, sulfur, mercury, lead, creatinine, cholesterol, estrogen, progesterone, testosterone, calcitonin, ghrelin, glucagon, inhibin, growth hormone, growth hormone-releasing hormone, insulin, vitamin, mineral, DHEA, DHT, alloisoleucine, toxic substance, illegal substance, hydrocarbon, arsenic, gold, silver, cadmium, strontium, mercury, lead, other heavy metals, chromium, antibiotic, gas, or any by-products thereof, a microorganism, plant cell, animal cell, fungal cell, plant, animal, fungus, or other organism. In an embodiment 1925, the at least one detecton material is responsive to the approximate number of microorganisms producing the at least one environmental medium treatment agent. In an embodiment 1930, the delivery device further comprises at least one memory mechanism for storing instructions for generating and transmitting an electromagnetic control signal. In an embodiment 1940, the delivery device further comprises at least one imaging apparatus capable of imaging the approximate quantity within a treatment region of one or more of the at least one composition, at least one constituent thereof, or at least one product thereof; at least one organism associated with the at least one environmental medium; at least one metabolite associated with the at least one environmental medium; or at least one cell or substance associated with the at least one environmental medium.

As indicated in FIG. 20, in an embodiment 2000, the delivery device further comprises at least one memory location for recording information. In an embodiment 2010, the at least one memory location is configured to record information regarding at least one sensor. In an embodiment 2020, the at least one memory location is configured to record information regarding at least one of a sensed condition, history, or performance of the device. In an embodiment 2030, the at least one memory location is configured to record information regarding one or more of the date, time, presence or approximate quantity of dispensing of one or more of the at least one composition, at least one constituent thereof, or at least one product thereof; at least one cell or substance associated with the at least one environmental medium; at least one organism associated with the at least one environmental medium; or at least one metabolite associated with the at least one environmental medium. In an embodiment 2040, the delivery device further comprises at least one information transmission mechanism configured to transmit information recorded by the at least one electronic memory location. In an embodiment 2050, the device is located in or is substantially in the form of one or more of a patch, tarp, insert, mesh, netting, or at least one disposable or biodegradable product. In an embodiment 2060, the device is located in or is substantially in the form of one or more of a food package, disposable package, bioreactor, spray apparatus, pump apparatus, or drilling apparatus. In an embodiment 2070, the delivery device further comprises at least one reservoir for controlled release of at least one inducer or repressor of the at least one heterologous genetic element encoding at least one environmental medium treatment agent. In an embodiment 2080, the delivery device further comprises at least one reservoir for controlled release of at least one inducer or repressor of the at least one genetic element inducible to initiate death of the at least one modified microorganism.

With regard to the figures, FIG. 1 illustrates at least one treatment area 100 that includes at least one environmental medium 110, for administration of at least one environmental medium treatment agent. In an embodiment, the treatment area corresponds to remediation of at least one compound, such as an element or contaminant, from the environmental medium. In an embodiment, the at least one composition including at least one modified microorganism is capable of converting at least one contaminant or other compound in the environmental medium into elements, or other extractable components (e.g., converting hydrocarbon or converting nitrogen-containing compounds). In an embodiment, the at least one environmental medium treatment agent binds to at least one compound in the environmental medium (e.g., binding elements, polymers, etc.). In an embodiment, the treatment area corresponds to an area deficient in nutrients (e.g., lawn, garden, golf course, other agricultural area). For example, as shown, a treatment area 100 may include at least one environmental medium 110 in proximity to an industrial area 120 or other area of high concentration of pollutants (e.g., gas station 130). In an embodiment, the environmental medium treatment agent provides at least one plant growth factor or other agent to encourage revitalization of the area 170. In at least one embodiment, the at least one environmental medium 110, is treated directly (e.g., drilling, spraying, sparging, patching or tarping) with the at least one environmental medium treatment agent.

In an embodiment, the at least one delivery device is in the form of a bioreactor 140. The bioreactor 140 can stand alone or be part of a system, as described herein. Furthermore, in an embodiment, the bioreactor 140 includes gas injectors (e.g., oxygen, hydrocarbon, etc.) to facilitate remediation of the at least one environmental medium, or to increase production of the at least one environmental medium treatment agent. For example, flow through or batch type reactors may be used. Flow rates into the system can be adjusted depending on the levels of contaminants or other compounds in the flow stream. In an embodiment, cycles are alternated between microbial growth with contaminant degradation and production of the at least one environmental medium treatment agent. For example, in an embodiment, the modified microorganisms are provided with at least one metabolite (e.g., air, oxygen, hydrocarbon, carbohydrate, etc.), which encourages production of the at least one environmental medium treatment agent and, in some instances, growth of the microorganisms. Subsequently, the environmental medium 110 to be treated is passed through the reactor for administration of the at least one environmental medium treatment agent and, in some instances, bioremediation of the at least one environmental medium.

Figure 2:
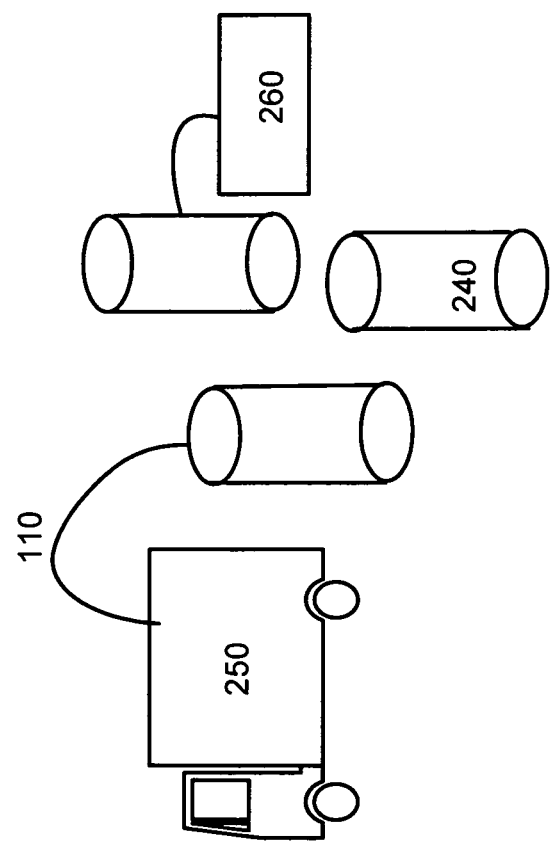
FIG. 2 illustrates a partial view of various embodiments disclosed herein.

As indicated in FIG. 2, in an embodiment, the environmental medium 110 is brought to the bioreactor 240 for treatment, or treated environmental medium 110 is removed from the bioreactor, for example by a vehicle 250. In an embodiment, the environmental medium 110 is treated in a system that provides the environmental medium to be treated, or collects the already treated environmental medium 260.

Figure 44:
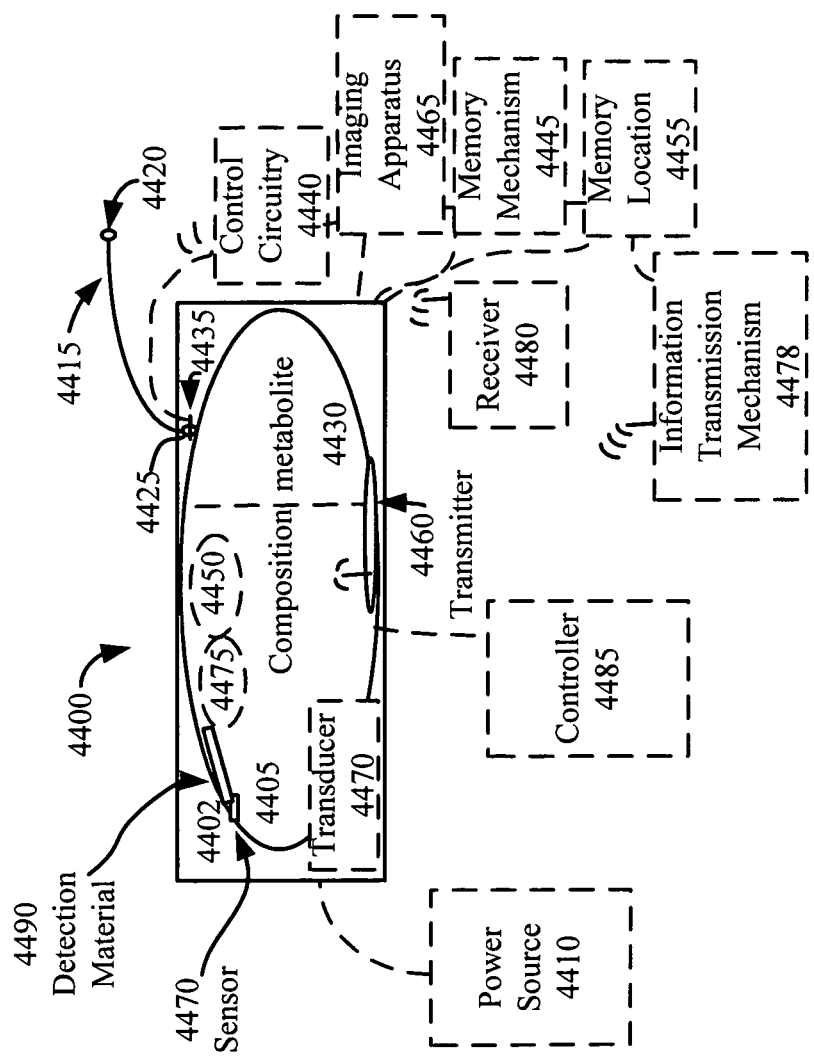
FIG. 44 illustrates a partial view of various embodiments of a delivery device including a composition disclosed herein.

As indicated in FIG. 44, and as disclosed in other figures and text herein, in an embodiment, a delivery device 4400, includes a housing 4402 including at least one reservoir 4405 containing at least one composition disclosed herein, and at least one component 4415 configured to administer the at least one composition to at least one substrate (e.g., biological tissue, environmental medium, etc.). In an embodiment, the delivery device includes one or more ports. For example, the one or more ports include but are not limited to at least an inlet port 4425, an outlet port 4420, or both. In an embodiment, at least one controllable output mechanism 4435 is operably linked to the one or more ports to control dispensing of at least a portion of the at least one composition. In an embodiment, the delivery device further comprises at least one control circuitry 4440 configured to generate and transmit an electromagnetic control signal configured to control the at least one controllable output mechanism 4435. In an embodiment, the delivery device further comprises at least one reservoir 4475 for controlled release of at least one inducer or repressor of the at least one heterologous genetic element encoding at least one environmental medium treatment agent. In an embodiment, the delivery device further comprises at least one reservoir 4450 for controlled release of at least one inducer or repressor of the at least one genetic element inducible to initiate death of the at least one modified microorganism. In an embodiment, the delivery device further comprises a transducer 4470. In an embodiment, the delivery device further comprises a transmitter 4460. In an embodiment, the delivery device further comprises a receiver 4480. In an embodiment, the delivery device further comprises a power source 4410.

In an embodiment, the delivery device further comprises at least one detection material 4490. In an embodiment, the detection material includes at least one of a taggant, contrast agent, sensor 4470, or electronic identification device. In an embodiment, the delivery device optionally includes separate reservoirs 4430 for separate constituents of the composition (e.g., metabolite, or other constituent). In an embodiment, the delivery device further comprises a controller 4485 configured to respond to the at least one sensor 4470. In an embodiment, the delivery device further comprises an imaging apparatus 4465. In an embodiment, the delivery device further comprises a memory mechanism 4445 for storing instructions for generating and transmitting an electromagnetic control signal. In an embodiment, the delivery device further comprises at least one memory location 4455 for recording information. In an embodiment, the delivery device further comprises an information transmission mechanism 4478 configured to transmit information recorded by the at least one electronic memory location.

Computer-Implemented Methods and Systems Thereof

In an embodiment, the method includes isolating at least one microorganism from the at least one substrate, modifying the at least one microorganism, and placing the modified microorganism back into the at least one original substrate, or into at least one other substrate. In an embodiment, modifying the at least one microorganism includes obtaining at least some genetic sequence from the at least one microorganism, and altering at least a portion of the genetic sequence of the at least one microorganism. In an embodiment, modifying the at least one microorganism includes chemically altering the at least one microorganism. In an embodiment, the at least one modified microorganism is amplified prior to placing into at least one substrate. In an embodiment, the amplification of the at least one modified microorganism includes amplifying the modified microorganism in vitro.

Isolating and sequencing microorganisms from substrates (e.g., biological tissues, environmental media, etc.) can be done according to standard techniques. For example, samples of the substrate are isolated and used to inoculate appropriate cultures, or microorganisms can be sequenced directly from the substrate sample. See, for example, U.S. Pat. No. 5,888,396, which is incorporated herein by reference. For example, rapid detection and quantitative assessment of specific microbial species in environmental samples can be conducted utilizing species-specific PCR primer sets. See, for example, Wilson, et al., Abstract, J. Micro. Meth., vol. 39, no. 1, pp. 59-78 (1999). For example, PCR primers can be developed for the 16S RNA gene, which is a highly variable region. These primers can be paired with a universal set of PCR primers chosen from highly conserved neighboring sequences in the same gene. Id. Amplification products can be verified and validated by utilizing, for example, hemi-nested PCR and with ligase chain reaction (LCR) techniques. Id.

As indicated by various testing measures, microorganism production of various proteins or other agents is measurable. For example, incorporation of radiolabeled leucine or thymidine into protein indicates that the mean turnover time for bacteria at approximately 22° C. is approximately 4.3 days. See, for example, Baath, Abstract, Biol. Fertil. Soils, vol. 17, pp. 147-153 (1994); Buesing and Gessner, Abstract, Microb. Ecol. vol. 45, pp. 291-301 (2003), each of which is incorporated herein by reference. In an embodiment, microbial growth rates can be estimated by measuring protein synthesis. Id. In an embodiment, production of the at least one agent by the at least one modified microorganism can be measured by radiolabeling a component (e.g., amino acid), as described. Id.

In an embodiment, the modified microorganism includes at least one heterologous genetic element, which may include an element isolated from another species or another organism (e.g., plant or animal). In an embodiment, the modified microorganism includes multiple heterologous genetic elements. In an embodiment, at least one of the multiple heterologous genetic elements is located on a separate locus from another element. In an embodiment, at least one of the multiple heterologous genetic elements is located on a separate vector from another element. In an embodiment, at least one of the multiple htereologous genetic elements is under the control of a promoter that is different from another element.

In an embodiment, the at least one modified microorganism includes at least one genetic element for one or more monooxygenase enzymes. For example, monooxygenase enzymes are utilized in biological cells for degradation of food or pharmaceutical drugs. In soil microbes, monooxygenase enzymes are utilized for degradation of contaminants. At least one gene has been isolated that encodes a methane monooxygenase enzyme (MMO) associated with the first step in methane oxidation by at least some methanotropic bacteria. See, for example, U.S. Pat. No. 5,316,940, which is incorporated herein by reference. For example, soluble methane monooxygenase (sMMO) constitutive mutant strains of M trichosporium (ATCC 55314) are capable of degrading chlorinated hydrocarbons in the presence of copper, which is normally suppressed in the presence of copper. Id. In an embodiment described herein, such mutants, or other modified microorganisms, are further modified to produce at least one agent (e.g., carbon, calcium, plant growth factors, etc.). In another embodiment, the cytochromes OmcA or OmcB are included in the at least one modified microorganism. See, for example, Myers and Myers, App. Env. Microbiol. vol. 68, no. 11, pp. 5585-5594 (2002), which is incorporated by reference. In an embodiment, the monooxygenase enzymes are involved in the biotransformation of at least one agent, including a therapeutic agent or environmental contaminant. See, for example, Hoensch, et al., Gut, vol. 20, pp. 666-672 (1979), which is incorporated herein by reference.

Furthermore, strains of Candida tropicalis are capable of growing on fatty acids or alkanes as the sole source of carbon and energy due to their cytochrome P450 monooxygenase enzymes. See, for example, Eschenfeldt, et al., App Env Microbiol. vol. 69, no. 10, pp. 5992-5999 (2003), which is incorporated herein by reference. Thus, either prokaryotic and eukaryotic microorganisms can be modified to utilize hydrocarbons as an energy source.

In an embodiment, at least one computer-implemented algorithm is utilized to predict at least one modified microorganism population suited for the particular substrate, or agent. In an embodiment, at least one computer-implemented algorithm is utilized to predetermine multiple populations of microorganisms for modification for a particular substrate or agent.

The disclosure further provides kits including at least one composition or method disclosed herein. Any particular kit may also contain instructional material teaching the methodologies and uses of the composition or method, as described herein.

The methods and therapeutic compositions are further described with reference to the following examples; however it is to be understood that the methods and compositions are not limited to such examples.

As indicated in FIG. 21, in an embodiment, a system 2100 comprises at least one computer device 2105, at least one delivery device 2110 configured to retain and dispense at least a portion of at least one composition to at least one biological tissue; 2115 and a recordable medium including one or more instructions that when executed on the computing device cause the computing device to regulate dispensing of at least a portion of the at least one composition, 2120 wherein the at least one composition includes at least one first constituent including at least one auxotrophic microorganism including at least one pH inducible promoter operably coupled to at least one heterologous genetic element encoding at least one therapeutic agent, and including at least one genetic element inducible to initiate death of the at least one auxotrophic microorganism; and at least one second constituent including at least one metabolite required by the at least one auxotrophic microorganism.

As indicated in FIG. 22, in an embodiment 2200, the at least one computing device includes at least one computing device located on or in the at least one delivery device. In an embodiment 2210, the at least one computing device includes at least one computing device located remotely from the at least one delivery device. In an embodiment 2220, the at least one computing device includes one or more of a desktop computer, workstation computer, or computing system. In an embodiment 2230, the at least one computing system includes one or more of a cluster of processors, a networked computer, a tablet personal computer, a laptop computer, a mobile device, a mobile telephone, or a personal digital assistant computer. In an embodiment 2240, the system further comprises one or more instructions that when executed on the at least one computing device cause the at least one computing device to generate at least one output to a user. In an embodiment 2250, wherein the at least one output includes at least one graphical illustration of one or more of the at least one composition, at least one constituent thereof, or at least one product thereof; at least one cell or substance associated with the at least one biological tissue; the at least one metabolite, or at least one product thereof; at least one property of the delivery device; or at least one property of dispensing the at least one delivery device. In an embodiment 2260, wherein the at least one output includes at least one protocol for generating the at least one auxotrophic microorganism. In an embodiment 2270, wherein the at least one output includes at least one protocol for making the at least one composition. In an embodiment 2280, wherein the at least one output includes at least one protocol for administering the at least one composition to the at least one biological tissue.

As indicated in FIG. 23, in an embodiment 2300, the user includes at least one entity. In an embodiment 2310, the entity includes at least one person, or computer. In an embodiment 2320, the output includes output to a user readable display. In an embodiment 2340, the user readable display includes a human readable display. In an embodiment 2350, the user readable display includes one or more active displays. In an embodiment 2360, the user readable display includes one or more passive displays. In an embodiment 2370, the user readable display includes one or more of a numeric format, graphical format, or audio format. In an embodiment 2380, the system further comprises one or more instructions for making the at least one composition. In an embodiment 2390, the system further comprises one or more instructions for inducing the at least one pH inducible promoter operably coupled to at least one heterologous genetic element encoding at least one therapeutic agent. In an embodiment 2395, the system further comprises one or more instructions for inducing the at least one genetic element inducible to initiate death of the at least one auxotrophic microorganism. In an embodiment 2398, the composition further comprises at least one repressor operably coupled to the at least one heterologous genetic element encoding at least one therapeutic agent.

As indicated in FIG. 24, in an embodiment 2400, the system further comprises one or more instructions for selecting the composition, or a constituent thereof. In an embodiment 2420, the system further comprises one or more instructions for administering the at least one composition or a constituent thereof to at least one biological tissue. In an embodiment 2430, the system further comprises one or more instructions for receiving information related to one or more biological tissue indicators prior to, during, or subsequent to administering the at least one composition to the at least one biological tissue. In an embodiment 2440, the information related to one or more biological tissue indicators includes information from at least one of an assay, image, or gross assessment of the at least one biological tissue prior to, during, or subsequent to administering the at least one composition. In an embodiment 2450, the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In an embodiment 2460, the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation.

As indicated in FIG. 25, in an embodiment 2500, one or more instructions for receiving information related to one or more biological tissue indicators relate to one or more of: administering the at least one composition, at least one constituent thereof, or at least one product thereof; administering the at least one metabolite, cell or tissue formation, cell or tissue growth, cell or tissue apoptosis, cell or tissue necrosis, cell division, cytoskeletal rearrangement, cell or tissue secretion, cell or tissue differentiation, status of the at least one microorganism of the at least one composition, status of the at least one composition, status of the at least one therapeutic agent, status of the at least one metabolite, or depletion of the at least one metabolite. In an embodiment 2510, the at least one biological tissue is located in at least one of in situ, in vitro, in vivo, in utero, in planta, in silico, or ex vivo. In an embodiment 2520, the at least one biological tissue is at least partially located in at least one subject. In an embodiment 2530, the at least one subject includes at least one of an invertebrate or vertebrate animal. In an embodiment 2540, the at least one subject includes at least one of a reptile, mammal, amphibian, bird, or fish. In an embodiment 2550, the at least one subject includes at least one human. In an embodiment 2560, the at least one subject includes at least one plant. In an embodiment 2570, one or more instructions for obtaining genetic sequence information from at least one microorganism isolated from the at least one biological tissue.

As indicated in FIG. 26, in an embodiment 2600, the system further comprises comprising one or more instructions for modifying the at least one microorganism isolated from the at least one biological tissue. In an embodiment 2610, the system further comprises one or more instructions for amplifying the at least one microorganism isolated from the at least one biological tissue. In an embodiment 2620, the system further comprises one or more instructions for reinstating the at least one microorganism isolated from the at least one biological tissue subsequent to modification. In an embodiment 2630, the system further comprises one or more instructions for predetermining at least one microorganism type for modifying to produce at least one therapeutic agent based on at least one feature of the at least one biological tissue. In an embodiment 2640, the at least one feature of the at least one biological tissue includes at least one property of one or more microorganism populations associated with the at least one biological tissue.

As indicated in FIG. 27, a computer-implemented method 2700, comprises 2710 one or more instructions for regulating dispensing at least one composition from at least one delivery device to at least one biological tissue, the at least one composition including at least one auxotrophic microorganism including at least one pH inducible heterologous genetic element encoding at least one therapeutic agent formulated for at least one biological tissue, and including at least one genetic element inducible to initiate death of the at least one auxotrophic microorganism; and at least one metabolite required by the at least one auxotrophic microorganism. In an embodiment 2720, the computer-implemented method further comprises generating at least one output to a user. In an embodiment 2730, the at least one output includes at least one graphical illustration of one or more of the at least one composition, at least one constituent thereof, or at least one product thereof; the at least one metabolite, or at least one product thereof; at least one cell or substance associated with the at least one biological tissue; at least one property of the at least one delivery device; or at least one property of dispensing the at least one delivery device. In an embodiment 2740, the at least one output includes at least one protocol for generating the at least one auxotrophic microorganism. In an embodiment 2750, the at least one output includes at least one protocol for making the at least one composition. In an embodiment 2760, the at least one output includes at least one protocol for administering the at least one composition to the at least one biological tissue.

As indicated in FIG. 28, in an embodiment 2800, the user includes at least one entity. In an embodiment 2810, the entity includes at least one person, or computer. In an embodiment 2820, the at least one output includes at least one output to a user readable display. In an embodiment 2830, the user readable display includes a human readable display. In an embodiment 2840, the user readable display includes one or more active displays. In an embodiment 2850, the user readable display includes one or more passive displays. In an embodiment 2860, the user readable display includes one or more of a numeric format, graphical format, or audio format. In an embodiment 2870, the computer-implemented method further comprises one or more instructions for making the at least one composition. In an embodiment 2880, the computer-implemented method further comprises one or more instructions to dispense the at least one composition or a constituent thereof to at least one biological tissue.

As indicated in FIG. 29, in an embodiment 2900, the computer-implemented method further comprises one or more instructions for dispensing at least one inducer formulated to induce the at least one genetic element inducible to initiate death of the at least one auxotrophic microorganism. In an embodiment 2910, the computer-implemented method further comprises receiving information related to one or more biological tissue indicators prior to, during, or subsequent to administering the at least one composition or a constituent thereof, to the at least one biological tissue. In an embodiment 2920, the computer-implemented method further comprises one or more instructions for dispensing the at least one composition or a constituent thereof, to the at least one biological tissue in response to the one or more biological tissue indicators. In an embodiment 2930, the computer-implemented method further comprises one or more instructions for dispensing at least one inducer formulated to induce the at least one genetic element inducible to initiate death of the at least one auxotrophic microorganism, to the at least one biological tissue in response to the one or more biological tissue indicators. In an embodiment 2940, the receiving information related to one or more biological tissue indicators includes information from at least one of an assay, image, or gross assessment of the at least one biological tissue prior to, during, or subsequent to administering the at least one composition. In an embodiment 2950, the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In an embodiment 2960, the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation.

As indicated in FIG. 30, in an embodiment 3000, the one or more biological tissue indicators relate to one or more of: administration of the at least one therapeutic agent, or a constituent thereof, or product thereof; administration of the at least one composition, or constituent thereof, or product thereof; administration of the at least one metabolite, administration of the at least one auxotrophic microorganism, cell or tissue formation, cell or tissue growth, cell or tissue apoptosis, cell or tissue necrosis, cell division, cytoskeletal rearrangement, cell or tissue secretion, cell or tissue differentiation, status of the at least one microorganism of the at least one composition, status of the at least one composition, status of the at least one therapeutic agent, status of the at least one metabolite, or depletion of the at least one metabolite. In an embodiment 3010, the at least one biological tissue is located in at least one of in situ, in vitro, in vivo, in utero, in planta, in silico, or ex vivo. In an embodiment 3020, the at least one biological tissue is at least partially located in at least one subject. In an embodiment 3030, the at least one subject includes at least one of an invertebrate or vertebrate animal. In an embodiment 3040, the at least one subject includes at least one of a reptile, mammal, amphibian, bird, or fish. In an embodiment 3050, the at least one subject includes at least one human. In an embodiment 3060, the at least one subject includes at least one plant. In an embodiment 3070, the computer-implemented method further comprises obtaining genetic sequence information from at least one microorganism isolated from the at least one biological tissue.

As indicated in FIG. 31, in an embodiment 3100, the computer-implemented method further comprises one or more instructions for modifying the at least one microorganism isolated from the at least one biological tissue. In an embodiment 3110, the computer-implemented method further comprises one or more instructions for amplifying the at least one microorganism isolated from the at least one biological tissue. In an embodiment 3120, the computer-implemented method further comprises one or more instructions for reinstating the at least one microorganism isolated from the at least one biological tissue subsequent to modification. In an embodiment 3130, the computer-implemented method further comprises one or more instructions for predeterming at least one microorganism type for modifying to produce at least one therapeutic agent based on at least one feature of the at least one biological tissue. In an embodiment 3140, the at least one feature of the at least one biological tissue includes at least one property of one or more microorganism populations associated with the at least one biological tissue.

As indicated in FIG. 32, in an embodiment, a computer program product 3200, comprises 3210 a recordable medium bearing one or more instructions for regulating dispensing of at least one delivery device, wherein the delivery device includes at least one composition, wherein the at least one composition includes at least one auxotrophic microorganism including at least one pH inducible heterologous genetic element encoding at least one therapeutic agent formulated for at least one biological tissue, and including at least one genetic element inducible to initiate death of the at least one auxotrophic microorganism; at least one metabolite required by the at least one auxotrophic microorganism; and generating at least one output. In an embodiment 3220, the recordable medium includes a computer-readable medium. In an embodiment 3230, the recordable medium includes a communications medium. In an embodiment 3240, the computer program product further comprises one or more instructions for receiving information related to one or more biological tissue indicators prior to, during, or subsequent to administering the at least one composition. In an embodiment 3250, the one or more biological tissue indicators relate to one or more of: administration of the at least one therapeutic agent, or a consitutent thereof; administration of the at least one composition, or constituent thereof, or product thereof; administration of the at least one metabolite, administration of the at least one auxotrophic microorganism, cell or tissue formation, cell or tissue growth, cell or tissue apoptosis, cell or tissue necrosis, cell division, cytoskeletal rearrangement, cell or tissue secretion, cell or tissue differentiation, status of the at least one microorganism of the at least one composition, status of the at least one composition, status of the at least one therapeutic agent, status of the at least one metabolite, or depletion of the at least one metabolite. In an embodiment 3260, the computer program product further comprises one or more instructions for obtaining genetic sequence information from at least one microorganism isolated from the at least one biological tissue.

As indicated in FIG. 33, in an embodiment 3300, the computer program product further comprises one or more instructions for modifying the at least one microorganism isolated from the at least one biological tissue. In an embodiment 3310, the computer program product further comprises one or more instructions for amplifying the at least one microorganism isolated from the at least one biological tissue. In an embodiment 3320, the computer program product further comprises one or more instructions for reinstating the at least one microorganism isolated from the at least one biological tissue subsequent to modification. In an embodiment 3330, the computer program product further comprises one or more instructions for predeterming at least one microorganism type for modifying to produce at least one therapeutic agent based on at least one feature of the at least one biological tissue. In an embodiment 3340, the at least one feature of the at least one biological tissue includes at least one property of one or more microorganism populations associated with the at least one biological tissue.

In an embodiment 3350, the output includes at least one protocol for making the at least one composition. In an embodiment 3360, the output includes at least one protocol for generating the at least one auxotrophic microorganism. In an embodiment 3370, the output includes at least one protocol for administering the at least one composition to at least one biological tissue. In an embodiment 3380, the output includes at least one graphical illustration of one or more of the at least one composition, at least one constituent thereof, or at least one product thereof; the at least one metabolite, or at least one product thereof; at least one cell or substance associated with the at least one biological tissue; at least one property of the at least one delivery device; or at least one property of dispensing the at least one delivery device. In an embodiment 3390, the computer program product further comprises one or more instructions for displaying results of the processing.

As indicated in FIG. 34, in an embodiment, a system 3400, comprises 3405 at least one computing device; 3410 at least one delivery device configured to retain and dispense at least one composition to at least one environmental medium; and 3415 a recordable medium including one or more instructions that when executed on the computing device cause the computing device to regulate dispensing of at least a portion of the at least one composition; 3420 wherein the at least one composition includes at least one modified microorganism including at least one heterologous genetic element encoding at least one environmental medium treatment agent; and at least one genetic element inducible to initiate death of the at least one modified microorganism.

As indicated in FIG. 35, in an embodiment 3500, the at least one computing device includes at least one computing device located on or in the at least one delivery device. In an embodiment 3510, the at least one computing device includes at least one computing device located remotely from the at least one delivery device. In an embodiment 3520, the at least one computing device includes one or more of a desktop computer, workstation computer, or computing system. In an embodiment 3530, the at least one computing system includes one or more of a cluster of processors, a networked computer, a tablet personal computer, a laptop computer, a mobile device, a mobile telephone, or a personal digital assistant computer. In an embodiment 3540, the system further comprises one or more instructions that when executed on the at least one computing device cause the at least one computing device to generate at least one output to a user. In an embodiment 3550, the at least one output includes at least one graphical illustration of one or more of the at least one composition, at least one constituent thereof, or at least one product thereof; at least one cell or substance associated with the at least one environmental medium; or the at least one property of dispensing the at least one delivery device. In an embodiment 3560, the at least one output includes at least one protocol for generating the at least one modified microorganism. In an embodiment 3570, the at least one output includes at least one protocol for making the at least one composition. In an embodiment 3580, the at least one output includes at least one protocol for administering the at least one composition to the at least one environmental medium.

As indicated in FIG. 36, in an embodiment 3600, the user includes at least one entity. In an embodiment 3610, the entity includes at least one person, or computer. In an embodiment 3620, the output includes an output to a user readable display. In an embodiment 3640, the user readable display includes a human readable display. In an embodiment 3650, the user readable display includes one or more active displays. In am embodiment 3660, the user readable display includes one or more passive displays. In an embodiment 3670, the user readable display includes one or more of a numeric format, graphical format, or audio format. In an embodiment 3680, the at least one environmental medium includes at least one of water, soil, food product, or air or other gas. In an embodiment 3690, the at least one environmental medium includes at least one of ground water, surface water, effluent, or wastewater. In an embodiment 3695, the water includes at least one of a lake, river, stream, sewage, sludge, slurry, sediment, ocean, fountain, or other water. In an embodiment 3696, the at least one environmental medium includes at least one of metal, concrete, cement, textiles, fabric, wood, mineral ore, or rock. In an embodiment 3697, the at least one environmental medium treatment agent includes at least one plant hormone. In an embodiment 3698, the at least one plant hormone includes at least one of an auxin, abscisic acid, cytokinin, ethylene, gibberellin, brassinolide, salicyclic acid, jasmonate, polyamine, plant peptide hormone, nitric oxide, strigolactone, or other compound.

As indicated in FIG. 37, in an embodiment 3700, the system further comprises one or more instructions for obtaining genetic sequence information from at least one microorganism isolated from the at least one environmental medium. In an embodiment 3710, the system further comprises one or more instructions for modifying the at least one microorganism isolated from the at least one environmental medium. In an embodiment 3720, the system further comprises one or more instructions for amplifying the at least one microorganism isolated from the at least one environmental medium. In an embodiment 3730, the system further comprises one or more instructions for reinstating the at least one microorganism isolated from the at least one environmental medium subsequent to modification. In an embodiment 3740, the system further comprises one or more instructions for predeterming at least one microorganism type for modifying to produce at least one environmental medium treatment agent based on at least one feature of the at least one environmental medium. In an embodiment 3750, the at least one feature of the at least one environmental medium includes at least one property of one or more microorganism populations associated with the at least one environmental medium. In an embodiment 3760, the system further comprises one or more instructions for making the at least one composition. In an embodiment 3770, the system further comprises one or more instructions for inducing at least one inducible promoter operably coupled to at least one heterologous genetic element encoding at least one environmental medium treatment agent. In an embodiment 3780, the system further comprises one or more instructions for inducing the at least one genetic element inducible to initiate death of the at least one modified microorganism. In an embodiment 3790, the system further comprises one or more instructions for selecting the composition, or a constituent thereof. In an embodiment 3795, the system further comprises one or more instructions for administering the at least one composition or a constituent thereof to at least one environmental medium.

As indicated in FIG. 38, in an embodiment 3800, a computer-implemented method comprises 3810 one or more instructions for regulating dispensing of at least one composition from at least one delivery device to at least one environmental medium, the at least one composition including at least one modified microorganism including at least one heterologous genetic element encoding at least one environmental medium treatment agent; and at least one genetic element inducible to initiate death of the at least one modified microorganism. In an embodiment 3820, the computer-implemented method further comprises generating at least one output to a user. In an embodiment 3830, the at least one output includes at least one graphical illustration of one or more of the at least one composition, at least one constituent thereof, or at least one product thereof; at least one metabolite utilizable by the at least one modified microorganism; at least one property of the at least one delivery device; or at least one property of dispensing of the at least one delivery device. In an embodiment 3840, the at least one output includes at least one protocol for generating the at least one modified microorganism. In an embodiment 3850, the at least one output includes at least one protocol for making the at least one composition. In an embodiment 3860, the at least one output includes at least one protocol for administering the at least one composition to the at least one environmental medium.

As indicated in FIG. 39, in an embodiment 3900, the user includes at least one entity. In an embodiment 3910, the entity includes at least one person, or computer. In an embodiment 3920, the output includes an output to a user readable display. In an embodiment 3930, the user readable display includes a human readable display. In an embodiment 3940, the user readable display includes one or more active displays. In an embodiment 3950, the user readable display includes one or more passive displays. In an embodiment 3960, the user readable display includes one or more of a numeric format, graphical format, or audio format. In an embodiment 3970, the computer-implemented method further comprises one or more instructions for making the at least one composition. In an emboeiment 3980, the computer-implemented method further comprises one or more instructions to dispense at least a portion of the at least one composition or a constituent thereof, to at least one environmental medium.

As indicated in FIG. 40, in an embodiment 4000, the computer-implemented method further comprises one or more instructions for dispensing at least a portion of at least one inducer formulated to induce the at least one genetic element inducible to initiate death of the at least one modified microorganism. In an embodiment 4010, the computer-implemented method further comprises receiving information related to one or more environmental medium indicators prior to, during, or subsequent to administering the at least one composition or a constituent thereof, to the at least one environmental medium. In an embodiment 4020, the computer-implemented method further comprises one or more instructions for dispensing at least a portion of the at least one composition or constituent thereof, to the at least one environmental medium in response to the one or more environmental medium indicators. In an embodiment 4030, the computer-implemented method further comprises one or more instructions for dispensing at least a portion of at least one inducer formulated to induce the at least one genetic element inducible to initiate death of the at least one modified microorganism, to the at least one environmental medium in response to the one or more biological tissue indicators.

In an embodiment 4040, the computer-implemented method the receiving information related to one or more environmental medium indicators includes information from at least one of an assay, image, or gross assessment of the at least one environmental medium prior to, during, or subsequent to administering the at least one composition.

In an embodiment 4050, the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In an embodiment 4060, the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation.

As indicated in FIG. 41, in an embodiment 4100, the one or more environmental medium indicators relate to one or more of: administration of the at least one composition, at least one constituent thereof, or at least one product thereof; administration of at least one metabolite utilizable by the at least one modified microorganism; administration of the at least one modified microorganism; status of the at least one modified microorganism of the at least one composition; status of the at least one composition; status of the at least one environmental medium treatment agent; or status of at least one metabolite utilizable by the at least one modified microorganism; or depletion of at least one metabolite utilizable by the at least one modified microorganism. In an embodiment 4110, the computer-implemented method further comprises obtaining genetic sequence information from at least one microorganism isolated from the at least one environmental medium. In an embodiment 4120, the computer-implemented method further comprises one or more instructions for modifying the at least one microorganism isolated from the at least one environmental medium. In an embodiment 4130, the computer-implemented method further comprises one or more instructions for amplifying the at least one microorganism isolated from the at least one environmental medium. In an embodiment 4140, the computer-implemented method further comprises one or more instructions for reinstating the at least one microorganism isolated from the at least one environmental medium subsequent to modification. In an embodiment 4150, the computer-implemented method further comprises one or more instructions for predeterming at least one microorganism type for modifying to produce at least one environmental medium treatment agent based on at least one feature of the at least one environmental medium. In an embodiment 4160, the at least one feature of the at least one environmental medium includes at least one property of one or more microorganism populations associated with the at least one environmental medium.

As indicated in FIG. 42, in an embodiment 4200, a computer program product comprises 4210 a recordable medium bearing one or more instructions for regulating dispensing of at least one delivery device, wherein the delivery device includes at least one composition, wherein the at least one composition includes at least one modified microorganism including at least one heterologous genetic element encoding at least one environmental medium treatment agent; at least one genetic element inducible to initiate death of the at least one modified microorganism; and generating at least one output. In an embodiment 4220, the recordable medium includes a computer-readable medium. In an embodiment 4230, the recordable medium includes a communications medium. In an embodiment 4233, the computer program product further comprises one or more instructions for obtaining genetic sequence information from at least one microorganism isolated from the at least one environmental medium.

In an embodiment 4235, the computer program product further comprises one or more instructions for displaying results of the processing. In an embodiment 4240, the computer program product further comprises one or more instructions for receiving information related to one or more environmental medium indicators prior to, during, or subsequent to administering the at least one composition. In an embodiment 4250, the one or more environmental medium indicators include one or more of: administration of the at least one composition, or constituent thereof, or product thereof; administration of at least one metabolite utilizable by the modified microorganism; administration of the at least one modified microorganism; status of the at least one modified microorganism of the at least one composition; status of the at least one composition; status of the at least one environmental medium treatment agent; or status of at least one metabolite utilizable by the modified microorganism; or depletion of at least one metabolite utilizable by the modified microorganism.

As indicated in FIG. 43, in an embodiment 4300, the output includes at least one protocol for making the at least one composition. In an embodiment 4310, the output includes at least one protocol for generating the at least one modified microorganism. In an embodiment 4320, the output includes at least one protocol for administering the at least one composition to at least one environmental medium. In an embodiment 4330, the output includes at least one graphical description of one or more of the at least one composition, constituent thereof, or product thereof; information related to at least one organism associated with the at least one environmental medium; or information related to at least one cell or substance associated with the at least one environmental medium. In an embodiment 4340, the computer program product further comprises one or more instructions for obtaining genetic sequence information from at least one microorganism isolated from the at least one environmental medium. In an embodiment 4350, the computer program product further comprises one or more instructions for modifying the at least one microorganism isolated from the at least one environmental medium.

In an embodiment 4360, the computer program product further comprises one or more instructions to dispense the at least one composition or a constituent thereof to at least one environmental medium. In an embodiment 4370, the computer program product further comprises one or more instructions for amplifying the at least one microorganism isolated from the at least on environmental medium. In an embodiment 4380, the computer program product further comprises one or more instructions for reinstating the at least one microorganism isolated from the at least one environmental medium subsequent to modification. In an embodiment 4390, the computer program product further comprises one or more instructions for predetermining at least one microorganism type for modifying to produce at least one environmental medium treatment agent based on at least one feature of the at least one environmental medium. In an embodiment 4395, the at least one feature of the at least one environmental medium includes at least one property of one or more microorganism populations associated with the at least one environmental medium.

PROPHETIC EXAMPLES

Example 1

Compositions Including Modified Microorganisms for the Delivery of a Therapeutic Agent Microorganisms are modified to produce at least one therapeutic agent (which may include an agent used as a responsive therapy, or prophylactic therapy, etc.). The modified microorganisms are retained in vivo by administration of at least one required factor as part of the modified microorganism composition.

The composition is given orally, following depleting resident microbes by administering ciproflaxocin dosed at moderate levels for 5 days. See, for example, Dethlefsen et al, PLoS Biology vol. 6, pp. 2383-2400 (2008), which is incorporated herein by reference. The modified microorganisms include live, commensal bacteria given orally, and are allowed to colonize the intestine following depletion of resident microorganisms by antibiotic treatment. See, for example, Wadolkowski, et al, Inf. Imm., vol. 56, pp. 1030-1035 (1988); and Rao, et al, PNAS, vol. 102, no. 34, pp. 11993-11998 (2005), each of which are incorporated herein by reference.

At least one antacid or proton pump inhibitor (e.g. Pantozol, Altana Pharma BV, Hoofdorp, Netherlands) and a cholate acid binder (e.g. Questran, Zambon, Amersfoort, Netherlands) are administered inconjunction with administration of the modified microorganism composition in order to improve viability during passage through the stomach. See, for example, Braat et al, Clin. Gastroenterol. Hepatol. vol. 4, pp. 754-759 (2006), which is incorporated herein by reference.

Example 2

Compositions Including Modified Microorganisms for the Delivery of a Therapeutic Agent

*Eschericia coli* (*E. coli*), Nissile 1917 is modified using rDNA methods to allow the bacteria to produce heterologous proteins or peptides. See, for example, Rao et al, Ibid., and U.S. Pat. No. 7,341,860; each of which is incorporated herein by reference. Expression of genes encoding the therapeutic agent (e.g., protein, microbicide, antigen, tolerogen, etc.) is directed by an inducible bacterial promoter (e.g., the acid inducible P170, P3, or P1 promoter (isolated from *Lactoccus*) and inducible by low pH). See, for example, Madsen, et al., Ibid.

Example 3

Compositions Including Modified Microorganisms for the Delivery of a Therapeutic Agent

*Eschericia coli* (*E. coli*), Nissile 1917 is modified using rDNA methods to allow the bacteria to produce heterologous proteins or peptides. See, for example, Rao et al, Ibid., and U.S. Pat. No. 7,341,860; each of which is incorporated herein by reference. The arabinose promoter ($P_{BAD}$) is fused to heterologous genes encoding therapeutic proteins or other therapeutic agents. Coexpression of araC, an arabinose operon regulatory protein, and provision of L-arabinose regulates expression of genes fused to the $P_{BAD}$ promoter. See, for example, U.S. Pat. No. 7,341,860, Ibid., which is incorporated herein by reference.

Example 4

Compositions Including Modified Microorganisms for the Delivery of a Therapeutic Agent

*Eschericia coli* (*E. coli*), Nissile 1917 is modified using rDNA methods to allow the bacteria to produce heterologous proteins or peptides. See, for example, Rao et al, Ibid., and U.S. Pat. No. 7,341,860; each of which is incorporated herein by reference. The heterologous gene constructs employ a constitutive promoter derived from the bacterial thymidine synthase gene which continuously expresses at least one therapeutic agent, such as a cytokine. See, for example, Steidler et al, Nature Biotechnology vol. 21, pp. 785-789 (2003), which is incorporated herein by reference.

That is, the heterologous gene construct encoding IL-2 is incorporated into an expression plasmid that also contains drug-resistance selectable markers (e.g. ampicillin resistance marker, β-lactamase, or chloramphenicol resistance marker) and transfected or electroporated into bacteria. See, for example, Sambrook et al, Molecular Cloning: A Laboratory Manual, second ed., Cold Spring Harbor Laboratory Press, N.Y. (1989), which is incorporated by reference herein.

Example 5

Compositions Including Modified Microorganisms for the Delivery of a Therapeutic Agent A propionate inducible expression system is utilized with transformed bacteria in order to provide a relatively homogenous expression in individual microorganism cells, and allow for highly regulatable expression. See, for example, Lee and Keasling, App. Env. Microbiol. vol. 71, no. 11, pp. 6856-6862 (2005), which is incorporated herein by reference. Expression vector pPro, as described by Lee and Keasling, is capable of being regulated at the single cell level over a wide range of inducer concentrations in a dose-dependent manner. Id. Furthermore, since bacterial cells are permeable to the inducer proprionate (which is metabolized by 2-MC by native chromosomal expression), regulatable and consistent induction in all cells of the culture is attainable.

Example 6

Compositions Including Modified Microorganisms for the Delivery of a Therapeutic Agent The bacteria are modified from standard bacterial strains by deleting or mutating genes encoding enzymes or other proteins essential for bacterial metabolism and growth by conventional standards (such as homologous recombination, recombinant DNA techniques, insertional mutagenesis, targeted gene deletion, etc.). See, for example, U.S. Pat. No. 5,643,771, and Biswas et al, J. Bacteriology, vol. 175, pp. 3628-3635 (1993); each of which is incorporated herein by reference.

Deletion of the thymidine synthase gene in *Lactococcus lactis* (*L. Lactis*) by homologous recombination using recombinant DNA plasmids results in *L. lactis* clones that require thymidine for growth. See, for example, Steidler et al, Ibid.

Subsequently, the *L. lactis* thymidine negative mutants are selected for by identifying which clones require thymidine for growth (e.g., through media supplementation). See, for example, Steidler et al, Ibid. Thymidine is present only at low levels in human colon, such that *L. lactis* thymidine auxotrophs survive less than two days following oral administration to human volunteers. See, for example, Braat et al, Ibid. However, thymidine auxotrophs survive longer than 200 hours in vitro when thymidine (10 µM) is provided, as published. Thus, the growth and survival of thymidine auxotrophs in vivo is regulated by dosing and scheduling administration of thymidine prior to, during, or subsequent to administration of the *L. lactis* and thymidine composition.

Example 7

Compositions Including Modified Microorganisms for the Delivery of a Therapeutic Agent Mutation or deletion of the β-aspartate semialdehyde dehydrogenase gene (Asd) in bacteria precludes synthesis of diaminopimelic acid (DAP), an essential cell wall constituent that is not present in animal tissues. Without exogenous DAP, bacteria that have a mutated or deleted Asd gene will undergo cell death and lysis (See, for example, U.S. Pat. No. 7,341, 860, Ibid.), but providing DAP by oral administration allows Asd mutants to grow, colonize and survive on mucosal surfaces in vivo. Id.

Example 8

Compositions Including Modified Microorganisms for the Delivery of a Therapeutic Agent Measurement and detection of the mutant bacteria that are present in vivo is conducted using quantitative polymerase chain reaction (PCR) and primers specific for the microbial strain and the gene expression construct. Stool samples from subjects given L. Lactis, modified to express human IL-10, is detectable with PCR primers specific for the 16s ribosomal RNA of L. lactis and the human IL-10 expression construct (See, for example, Braat et al, Ibid.).

Example 9

Compositions Including Modified Microorganisms for the Delivery of a Therapeutic Agent The number of colony forming units (CFU) of L. Lactis is assessed by culturing stool samples on microbiological plates containing selective media. Briefly, fecal samples are suspended in minimal media and then selected on plates coated with antibodies specific for L. Lactis. Next, media containing essential nutrients (including thymidine) is overlaid and the bacterial colonies arising are counted to determine the CFU present in the fecal sample (See, for example, Steidler et al, Ibid.).

Since thymidine synthase mutants of L. lactis (ThyA⁻ L. Lactis) are dependent on exogenous thymidine for growth in vitro and in vivo, no viable ThyA⁻ L. Lactis are present after culture 72 hours in rich media devoid of thymidine, but in cultures containing 10 µM thymidine, the microbes survive beyond 200 hours. In vivo, only 4% of ThyA⁻ L. Lactis auxotrophs survive after 4 hours in the mammalian intestine with only endogenous thymidine present (thymidine concentration is less than 0.075 µM in human ileal lavage; See, for example, Steidler et al, Ibid.).

Example 10

Compositions Including Modified Microorganisms for the Delivery of a Therapeutic Agent Production of at least one therapeutic agent, IL-10, by L. lactis (ThyA⁻ L. Lactis) is controlled by an inducible promoter, $P_{BAD}$/araC promoter/regulator system (see, for example, U.S. Pat. No. 7,341,860, Ibid.). The inducible promoter is used in conjunction with arabinose to regulate the production of IL-10 in the microorganism. In an embodiment, production and delivery in situ is regulated by dosing and scheduling of arabinose administration, while bacterial survival and growth is regulated through dosing and scheduling of thymidine administration.

The amount of IL-10 delivered is monitored by immunoassay of fecal samples. For example, human IL-10 derived from feces samples is measured by enzyme linked immunosorbent assay (ELISA; Steidler et al, Ibid.). ELISA reagents and protocols for numerous cytokines including IL-10 are available, for example, from Invtrogen Corp., Carlsbad, Calif.

Example 11

Compositions Including Modified Microorganisms for the Delivery of a Therapeutic Agent Production of a suicide factor, Rel F, is regulated by a synthetic gene network engineered into a microorganism. Briefly, oral administration of an inducer molecule (arabinose) controls expression of IL-10. A synthetic gene network responsive to pulses of a metabolite (e.g., arabinose), is utilized, as described in Friedland et al., Science, vol. 324, pp. 1199-1202 (2009), which is incorporated herein by reference. The gene network is constructed by combining transcriptional and translational regulatory elements. The $P_{BAD}$ promoter, a transactivating noncoding RNA, a cis repressor sequence RNA, and a T7 RNA polymerase gene are combined in a synthetic gene network to control the expression of multiple proteins as shown by Friedland et al., Ibid. The regulatory elements cause one particular product to be produced with a first induction event (e.g., exposure to arabinose); a second particular product to be produced with a second induction event; a third particular product to be produced with a third induction event, etc. In this manner, the synthetic system allows for exhibiting the number of induction events that have occurred, or "counting" induction events. Id.

Thus, the therapeutic agent (e.g., IL-10) is delivered to a patient's intestine by ingestion of modified E. coli containing a plasmid encoding a synthetic gene network that responds to multiple pulses of an inducer molecule (e.g., arabinose) by the production of IL-10. The gene network also contains suicide genes (e.g. Rel F) that will cause cell death when they are expressed. See, for example, U.S. Pat. No. 6,610,529, which is incorporated herein by reference. The frequency and duration of arabinose pulsing determines the expression of genes (and their corresponding proteins) in the gene network, while the dose and schedule of oral arabinose administration determines the timing and duration of expression of the therapeutic agent and suicide gene, IL-10 and Rel F, respectively.

The synthetic gene networks for therapeutic agent production utilize optimal pulse intervals of approximately 10-40 minutes and optimal pulse lengths of approximately 20-30 minutes, while synthetic gene networks for suicide gene expression utilize optimal pulse intervals and pulse lengths of approximately 2-12 hours (see Friedland et al., Ibid.). For example, gene networks encoding IL-10 utilize approximately two 10-minute pulses of arabinose separated by an interval of 20 minutes to optimally induce IL-10 expression, while Rel F expression and cell death ensue following two 2-hour pulses with arabinose separated by 2 hours.

Synthetic gene networks incorporating multiple inducers (e.g., arabinose, anhydrotetracycline and IPTG), and the expression of multiple genes in the network can be employed that utilize variations of the order, length and interval of pulsing with each of the inducers. See, Friedland et al., Ibid.

Example 12

Compositions Including Modified Microorganisms for the Delivery of a Therapeutic Agent Modified E. coli including a plasmid encoding the Rel F gene regulated by a promoter, such as pLac that is repressed by a regulator protein, LacIq, unless isopropyl β-D-thiogalactoside (IPTG) is provided. Thus, in order to control the growth of the modified E. coli strain in vivo, IPTG is administered to induce Rel F expression and cause cell death. Alternatively the Rel F gene can be controlled by the arabinose promoter/repressor. Thus, expression of Rel F is regulated by the C2 repressor which, in turn, is regulated by the presence of arabinose. When arabinose levels are reduced, C2 repressor levels decline, resulting in Rel F expression and leading to bacterial cell death (see, for example, U.S. Pat. No. 6,610,529, which is incorporated herein by reference).

Example 13

Compositions Including Modified Microorganisms for the Delivery of a Therapeutic Agent In an embodiment, mutually dependent strains of bacteria that signal via small molecules, such as acyl-homoserine lactones (acyl-HSL), are modified to express heterologous target genes only when sufficient numbers of both bacterial strains (and acyl-HSL) are present. See, for example, Brenner et al, PNAS, vol. 104, pp. 17300-17304 (2007), which is incorporated herein by reference. Thus, two *E. coli* strains, modified to produce specific acyl-HSL, control the expression of target genes for each other, while target gene expression is controlled by providing exogenous acyl-homoserine lactone to the individual microbial strains.

Administration of 3-oxododecanoyl-HSL (3OC12HSL) and butanoyl-HSL (C4HSL) in vivo is used to regulate target protein production of the two *E. coli* strains (see, for example, Brenner et al, Ibid.). In addition, survival of the two strains is regulated by acyl-HSL-regulated expression of a toxin (ccd B) gene (causes cell death), and an antitoxin (ccd A) gene (allows survival). See, for example, Balagadde et al, Mol. Sys. Biol., vol. 4, pp. 1-8 (2008), which is incorporated herein by reference. The toxin-antitoxin includes at least one of masEF, chpBIK, relBE, yefM-yoeB, dinJ-yafl, or ecnA-ecnB. See, Engleberg-Kulka, et al., PLOS Genetics, vol. 2, no. 10, 1518-1526 (2006), which is incorporated herein by reference.

Coadministration of multiple bacterial strains that express different target genes are used to co-deliver multiple therapeutic agents. For example, localized co-expression of IL-10 and transforming growth factor beta (TGF-β) by separate bacterial strains, provide localized immunoregulatory therapy for conditions such as inflammatory bowel disease.

Example 14

Compositions Including Modified Microorganisms for the Delivery of a Therapeutic Agent A bacterial strain that expresses an antigen derived from a viral pathogen, for example, E7 antigen from human papilloma virus type 16, is coadministered with a second bacterial strain that produces interleukin-12 (IL-12) to promote immunization. The two bacterial strains are auxotrophs that are mutually dependent on each other for essential metabolites, such as amino acids or DAP.

One or both auxotrophic strains are sustained in vivo by administering exogenous metabolites (e.g. histidine, arabinose, DAP, acyl-HSL, thymidine) to the host organism. In an embodiment, expression of the E7 gene and IL-12 is directed by the same or a different promoter. For example, E7 and IL-12 are fused to the lac operon promoter ($P_{lac}$), which is inducible with IPTG or lactose.

Example 15

Compositions Including Modified Microorganisms for the Delivery of a Therapeutic Agent Modified fungi, derived from generally regarded as safe (GRAS) species can be auxotrophic for essential metabolites and express protein-encoding genes under the control of regulated promoters. For example, in an embodiment, *Saccharomyces cerevesiae* (*S. cerevesiae*) and *Saccharomyces boulardii* (*S. boulardii*) are GRAS organisms that are mutated and selected (see, for example, Abosereh et al, Res. J. Agric. Biol. Sci., vol. 2, pp. 478-482 (2006), which is incorporated by reference herein) to obtain clones that require amino acids (e.g., leucine, tryptophan, lysine, arginine), purines, or pyrimidines (e.g., adenine, thymidine). Growth and survival of yeast auxotrophs in vitro and in vivo is dependent on an essential metabolite (e.g., adenine), and if adenine is not present (or present at low levels) in a subject hosting the strain, then growth of the yeast auxotroph is regulated by administering adenine to the subject. For example, the dose and schedule of adenine administration controls the proliferation and survival of the yeast adenine auxotrophs.

Yeast cloning vectors used for protein expression include but are not limited to yeast integrative plasmids, yeast episomal plasmids, and yeast centromeric plasmids that contain selectable markers based on metabolite requirements. Genes used as selectable markers include but are not limited to LEU2, URA3, and HIS3, which encode enzymes needed to biosynthesize leucine, uracil and histidine (for example, yeast vectors for protein expression are described in Glazer et al, Microbial Biotechnology: Fundamentals of Applied Microbiology, $2^{nd}$ edition, Cambridge University Press (2007), which is incorporated herein by reference. Transcription of heterologous genes is directed by a constitutive promoter (e.g., ADH1, TDH3) or a regulated promoter (e.g., GAL1, ADH2, PHO5, CUP-1, etc.).

Example 16

Compositions Including Modified Microorganisms for the Delivery of a Therapeutic Agent Modified yeast strain that requires two metabolites, for example, leucine and histidine, a selectable marker (e.g. LEU2) provides plasmid stability, while the metabolite (e.g., histidine or leucine) regulates growth and survival of the yeast strain. For example, in an embodiment, modified *S. boulardii* is used for vaccination, wherein the strain requires leucine and histidine, and produces a heterologous protein, hepatitis B surface antigen encoded on a yeast episomal plasmid containing LEU2, and under the control of the ADH1 constitutive promoter. Dosing and scheduling of histidine administration regulates the growth and survival of the modified *S. boulardi* and, in turn, the production and delivery of hepatitis B surface antigen.

Example 17

Compositions Including Modified Microorganisms for the Delivery of a Therapeutic Agent A modified yeast strain transformed with a recombinant plasmid encoding a nuclease (e.g. *Serratia marcescens* nuclease A) under the control of the *S. cerevesiae* ADH2 promoter, undergoes cell death when the nuclease A gene is expressed. Ordinarily, the ADH2 promoter is repressed by glucose, and when glucose levels are depleted the ADH2 promoter/nuclease A gene is expressed, resulting in cell death. See, for example, Balan et al, Yeast, vol. 22, pp. 203-212 (2005) which is incorporated herein by reference. Thus, death of the modified yeast strain is induced in a glucose poor environment (e.g. feces, intestine, soil, etc.).

Example 18

Compositions Including Modified Microorganisms for the Delivery of a Therapeutic Agent Co-administration of two yeast (*Saccharomyces cerevesiae*) auxotrophs, one that requires lysine, and a second that requires adenine, are modified to over-produce adenine and lysine, respectively. The mutants are generated using conventional methods, such as mutation, selection and genetic crosses. See, for example, Shou et al, PNAS, vol. 104, pp. 1877-1882 (2007), which is incorporated herein by reference.

Co-administration of live yeast strains that are mutually dependent on each other for survival allows prolonged survival and colonization of both strains on mucosal surfaces (e.g. intestinal, vaginal, nasal, oral, bronchial, etc.). The yeast strains are modified to express enzymes essential for overproduction of adenine and lysine under the control of regulated promoters, CUP-1 promoter derived from the metallothionein gene. (See, for example, Glazer et al, Ibid.)

Transcription of genes fused to CUP-1 is induced by providing metal ions such as $Cu^{2+}$ and $Zn^{2+}$. For example, $ZnCl_2$ can be given orally to induce expression of $ADE4^{op}$ and $LYS21^{op}$, enzymes that mediate over-production of adenine and lysine, respectively, by modified yeast residing, for example, in the colon (see, for example, Shou et al, Ibid.). Withdrawal of $ZnCl_2$ from the diet lowers $Zn^{2+}$ levels, reduces expression of $ADE4^{op}$ and $LYS21^{op}$, and reduces production of adenine and lysine which, in turn, leads to death of the modified yeast strains.

Example 19

Compositions and Methods of Administering Therapeutic Agents to Plants

*Pseudomonas fluorescens* strain SBW25 inhabits the leaves and roots of sugar beet plants and is competent for transformation with recombinant DNA plasmids. See, for example, Zhang, et al., Microbiol. vol. 152, pp. 1867-1875 (2006), which is incorporated herein by reference. *P. fluorescens* is transformed with a DNA plasmid that encodes an anti-microbial peptide, PW2. See, for example, U.S. Pat. No. 5,017,373; and U.S. Pat. No. 7,510,852, each of which is incorporated herein by reference. PW2, and methods for its cloning and construction are described in U.S. Pat. No. 7,550,558, which is incorporated herein by reference. As published, PW2 has anti-fungal activity against the following plant fungal pathogens: *Colletotrichum gossypii, Cephalosporioides, Alternaria macrospora, Colletotrichum ora, Bipolaris sorokiniana, Dreschslera tritici, Phoma sorghina, Pyricularia grisea, Colletotrichum, Gloeosporioides, Rhizoctonia solani* and *Fusarium solani*.

Thus, the modified *P. fluorescens* strain delivers the anti-fungal peptide PW2 to at least one biological tissue, such as plant leaves, stems, or roots to prevent the growth, inhibit the growth or reduce the viability of fungal plant pathogens.

The *P. fluorescens* strain is also modified with an inducible genetic element (e.g., Rel F) to initiate death of the bacteria when a factor is provided to induce the suicide gene. The composition including the modified microorganism and induction factor is applied sequentially to the plants, and optionally to their environment (e.g., soil or water), by spraying, dusting, sprinkling, or otherwise applying the composition to the selected area. Expression of the Rel F gene is controlled by a regulated promoter such as pLac that is repressed by a regulator protein, LacIq, unless isopropyl β-D-thiogalactoside (IPTG) is provided.

Thus, in order to control growth of the modified microbial strain, IPTG (available from Sigma-Aldrich Corp., St. Louis, Mo.) is applied to the plant or soil areas where the composition has also been applied or translocated, in sufficient amount to induce Rel F expression and leading to death of the microorganism(s). IPTG is applied by spraying, dusting, sprinkling or other application. An IPTG solution containing approximately 3 mM IPTG is used to induce expression of the repressed pLac promoter. See, for example, Sambrook, Fritsch & Maniatis, Molecular Cloning: A Laboratory Manual, Second Edition (1989) Cold Spring Harbor Laboratory Press, Cold Spring Harbor, N.Y. which is incorporated herein by reference.

Example 20

Compositions and Methods of Administering Therapeutic Agents to Plants

*Pseudomonas* known to inhabit the phylloplane (the surface of plant leaves) or the rhizosphere (the soil surrounding plant roots) are used as microbial hosts for plasmid expression vectors directing the expression of an anti-fungal peptide, PW2.

Modified *Pseudomonas* strains are stable within the rhizosphere of wheat and barley plants for approximately 1 month at a level of approximately $1.0 \times 10^5$ to $23 \times 10^5$ CFU/cm of root and is capable of stably expressing recombinant genes for approximately 29 days, according to published reports. See, for example, Shim et al., Appl. Envir. Microbiol. vol. 66, pp. 4673-4678 (2000), which is incorporated herein by reference. For example, modified microorganism compositions are applied in the field by spraying, dusting, soaking, soil injection, seed coating, seedling coating, or the like. Bacterial suspensions for application to plants are approximately $10^6$ to $10^{10}$ cells/ml and the volume applied per hectacre is approximately 10 ml to 100,000 ml or more. Administration of bacterial suspensions to a plant part is at approximately $10^3$ to $10^6$ cells/cm$^2$.

Example 21

Compositions and Methods of Administering Environmental Medium Treatment Agents to Environmental Media A modified microorganism includes at least one heterologous genetic element encodes at least one plant growth factor, for example, acetoin (3-hydroxy-2-butanone) and 2,3-butanediol in the environmental medium (e.g., soil), for example, in order to promote the growth of plants. According to published studies, naturally occurring plant-growth promoting rhizobacteria, which are capable of producing acetoin, increase leaf growth in *Arabidopsis thaliana* by more than 100% relative to control bacteria not capable of producing acetoin. See, for example, Ryu et al, PNAS, USA, vol. 100, pp. 4927-4932 (2003), which is incorporated herein by reference.

Thus, a bacterium that lives in the soil, *Streptomyces lividans*, is transformed with at least one genetic element (i.e. gene, promoter element, regulatory sequence, etc.) that encodes at least one enzyme required to produce at least one plant growth factor. For example, *S. lividans* (ATCC #69441; available from American Type Culture Collection, Manassas, Va.) is modified by transformation with a plasmid (e.g. pIJ702) containing at least one enzyme gene required to produce at least one plant growth factor (e.g., acetoin, gibbrellin, 2,3-butanediol, etc.). Transformation of the microorganism can be conducted utilizing standard procedures. See, for example, Wang et al, J. Biotech., vol. 13, pp. 131-144 (1990); and Sambrook et al, Molecular Cloning: A Laboratory Manual, second ed., Cold Spring Harbor Laboratory Press, N.Y. (1989), each of which is incorporated herein by reference.

For example, *S. lividans* bacteria are modified to express the acetolactate synthase (AlsS) and acetolactate decarboxylase (AlsD) genes which act on pyruvate, a common metabolite, to yield acetoin. See, for example, Taghavi et al, Appl. Envir. Microb. vol. 75, no. 3, pp. 748-757 (2009), which is incorporated herein by reference. Cloning and expression of an AlsS gene in *S. lividans* is conducted utilizing standard procedures. See, for example, Smith et al, PNAS, USA, vol. 86, pp. 4179-4183 (1989); and Swindell et al, Appl. Envir. Microbiol., vol. 62, no. 7, pp. 2641-2643 (1996), each of which is incorporated herein by reference.

Expression of genes encoding the AlsS and AlsD enzymes is directed by the inducible lac operon promoter fused to at least one gene encoding at least one enzyme (e.g. AlsS, AlsD), and gene expression is induced with lactose or isopropyl β-D-thiogalactoside. See, for example, Rao, et al, PNAS, USA vol. 102, no. 34, pp. 11993-11998 (2005), which is incorporated herein by reference.

The expression plasmid includes at least one drug-resistance selectable marker (e.g. ampicillin resistance marker, β-lactamase, or chloramphenicol resistance marker). Routine methods for gene transfer and components relating to selectable markers are described, for example, in Sambrook et al, Molecular Cloning: A Laboratory Manual, second ed., Cold Spring Harbor Laboratory Press, N.Y. (1989), which is incorporated herein by reference.

*S. lividans*, is additionally transformed with at least one genetic element inducible to initiate death in the at least one modified microorganism. For example, the at least one inducible genetic element encodes at least one lethal or suicide gene (Rel F) under the control of an inducible promoter, such as pLac. The inducible promoter pLac is repressed by an inducer, LacIq, unless isopropyl β-D-thiogalactoside (IPTG) is provided (see Rao et al, Ibid.). Thus, in order to initiate death in the modified *S. lividans*, IPTG is administered to induce Rel F expression and initiate cell death.

The composition including modified *S. lividans* bacteria transformed with the genetic element encoding acetoin is sprayed onto soil as a spore suspension in water at a rate of approximately $10^6$-$10^8$ colony forming units (CFU) per gram of soil. As shown by published studies, modified *S. lividans* innoculated at approximately $10^7$ CFU/gm soil and grown at 25° C. survive for at least approximately 90 days. See, for example, Crawford et al, Appl. Envir. Microbiol., vol. 59, pp. 508-518 (1993), which is incorporated herein by reference.

The survival of *S. lividans* is measured by diluting in water and spreading on plates containing at least one antibiotic to which the microorganism has been rendered resistant. For example, *S. lividans* strain TK23 is modified to be resistant to spectinomycin, while *S. lividans* transformed with the plasmid, pIJ702 is resistant to thiostrepton. See, for example, Crawford et al, Ibid.

Example 22

Compositions and Methods of Administering Environmental Medium Treatment Agents to Environmental Media A method includes administering at least one composition including at least one modified microorganism encoding at least one environmental medium treatment agent, such as a plant peptide hormone, to at least one environmental medium (e.g., soil, water, etc.). In an embodiment, the at least one modified microorganism includes at least one inducible genetic element to initiate death of the at least one modified microorganism.

*Pseudomonas putida* is modified to include at least one genetic element encoding at least one plant peptide hormone (e.g., POLARIS), and at least one genetic element inducible to initiate death in the at least one modified microorganism (e.g., Rel F), and each is controlled by a synthetic gene network of the microorganism. As shown in published studies, application of an inducer molecule regulates expression of POLARIS, a 36 amino acid peptide that functions in root growth and leaf vascularization. See, for example, Casson et al, Plant Cell, vol. 14, pp. 1705-1721 (2002), which is incorporated herein by reference. The synthetic gene network is responsive to pulses of a metabolite (e.g., arabinose). See, for example, Friedland et al., Science, vol. 324, pp. 1199-1202 (2009), which is incorporated herein by reference.

Thus, the synthetic gene network is constructed by combining transcriptional and translational regulatory elements including the pBAD promoter, a transactivating noncoding RNA, a cis repressor sequence RNA, and a T7 RNA polymerase gene. See, for example, Friedland et al., Ibid.

The frequency or duration of arabinose application determines the expression of the inducible genetic element (and the corresponding protein(s)) in the synthetic gene network, and the dose and schedule of arabinose application to the soil determines the timing and duration of expression of POLARIS and Rel F. As published, synthetic gene networks have optimal pulse intervals of approximately 10-40 minutes and optimal pulse lengths of approximately 20-30 minutes. Id. Additionally, synthetic gene networks with optimal pulse intervals and pulse lengths of approximately 2-12 hours are also described. Id. Other optimal pulse intervals can be determined for a particular system, according to the published guidelines. Id.

Thus, synthetic gene networks incorporating multiple inducers (e.g., arabinose, anhydrotetracycline and IPTG), and the expression of multiple genes in the network depends on the order, length, and interval of pulsing with each of the inducers. Id.

Example 22

Compositions and Methods of Administering Environmental Medium Treatment Agents to Environmental Media

*P. putida*, a bacteria commonly found in soil, is modified to include three genetic elements: 1) a regulated promoter (e.g., pLac) fused to a suicide gene (e.g., gef), and 2) a TOL plasmid promoter (e.g., Pm) fused to the lad gene (encoding the Lac repressor), and 3) xylS2, a gene encoding a positive regulator of Pm that interacts with 3-methyl benzoate. See, for example, Ramos, et al., Biotech: vol. 12, pp. 1349-1356 (1994), which is incorporated herein by reference. P. putida is modified to produce POLARIS under the control of a constitutive promoter (for example, the bacterial thymidine synthase promoter, according to Steidler et al, Ibid.) is transformed with a DNA cassette containing the pLac promoter fused to the gef gene. The strain is also transformed with a plasmid that contains the Pm promoter fused to lad gene and encoding the xylS2 positive regulator of Pm. Genetic constructs and construction of recombinant bacterial strains is conducted by routine procedures, some of which are described in Jensen et al, Appl. Env. Micro., vol. 59, pp. 3713-3717 (1993), which is incorporated herein by reference.

Modified P. putida encoding POLARIS, and including at least one genetic element inducible to initiate death of the P. putida, is grown in the presence of 3-methylbenzoate. When 3-methylbenzoate is combined with the xylS2 gene product, positive regulation of Pm results, and leads to production of the Lac repressor. The Lac repressor represses the expression of the toxic gene, gef. According to published studies, P. putida strains including a substrate-regulated toxic gene system inoculated at approximately $10^6$ CFU/gm to nonsterile soil containing 0.08% (wt/vol.) 3-methyl benzoate are present at approximately $10^8$ CFU/gm of soil after approximately 14 days. See, for example, Jensen et al, Ibid. However, in control experiments without 3-methyl benzoate only approximately $10^2$ CFU/gm of soil survived after 14 days. Id.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

All publications and patent applications cited in this specification are herein incorporated by reference to the extent not inconsistent with the description herein and for all purposes as if each individual publication or patent application were specifically and individually indicated to be incorporated by reference for all purposes.

What is claimed is:

1. A composition, comprising:
    at least two modified microorganisms that are mutually dependent and express at least one environmental medium treatment agent only after satisfying a population threshold, at least one modified microorganism including at least one heterologous genetic element encoding at least one-environmental medium treatment agent including at least one of nitroreductase; and at least one modified microorganism including at least one heterologous genetic element encoding at least one environmental medium treatment agent including an enzyme required to produce at least one plant growth factor;
    and wherein each of the at least two modified microorganisms include
    at least one genetic element operably coupled to at least one promoter or enhancer and inducible to initiate death of the at least one modified microorganism; and
    at least one sensor including an RNA aptamer, a hammerhead ribozyme actuator, and a transmitter including a sequence that couples the sensor and actuator.

2. The composition of claim 1, wherein the at least one genetic element inducible to initiate death of the at least two modified microorganisms includes at least one heterologous genetic element.

3. The composition of claim 1, wherein the at least one plant growth factor includes at least one plant hormone.

4. The composition of claim 3, wherein the at least one plant hormone includes at least one of an auxin, abscisic acid, cytokinin, ethylene, gibberellin, brassinolide, salicyclic acid, jasmonate, polyamine, plant peptide hormone, nitric oxide, or strigolactone.

5. The composition of claim 1, wherein the at least one genetic element inducible to initiate death of the at least two modified microorganisms includes at least one of an inducible promoter, inducible enhancer, or inducible repressor.

6. The composition of claim 1, further including at least one metabolite utilizable by at least one of the at least two modified microorganisms.

7. The composition of claim 6, wherein the at least one metabolite includes at least one inducer of the heterologous genetic element encoding at least one environmental medium treatment agent.

8. The composition of claim 6, wherein the at least one metabolite includes at least one repressor of at least one of the heterologous genetic elements encoding at least one environmental medium treatment agent.

9. The composition of claim 6, wherein the at least one metabolite includes at least one inducer of at least one genetic element inducible to initiate death of at least one of the two modified microorganisms.

10. The composition of claim 6, wherein the at least one metabolite includes at least one repressor of the at least one genetic element inducible to initiate death of at least one of the two modified microorganisms.

11. The composition of claim 6, wherein the at least one metabolite includes a time-release formulation.

12. The composition of claim 6, wherein the at least one metabolite is pH-dependent.

13. The composition of claim 6, wherein the at least metabolite is temperature dependent.

14. The composition of claim 6, wherein the at least one metabolite includes the at least one environmental medium treatment agent.

15. The composition of claim 6, wherein the at least one metabolite is provided or produced by the at least one environmental medium.

16. The composition of claim 6, wherein the at least one metabolite is provided by at least one biological cell.

17. The composition of claim 1, wherein the at least one genetic element inducible to initiate death of either of the modified microorganisms includes at least one genetic element inducible to initiate programmed cell death.

18. The composition of claim 1, wherein the at least one modified microorganism includes at least one of a prokaryote or a eukaryote.

19. The composition of claim 1, wherein the at least one modified microorganism includes at least one of bacteria, protozoa, rotifers, algae, archaeon, or fungi.

20. The composition of claim 1, wherein the at least one modified microorganism includes at least one of a non-pathogenic strain, transgenic microorganism, magnetotactic microorganism, anaerobic microorganism or aerobic microorganism, food grade strain, obligate microorganism, attenuated microorganism strain, facultative anaerobe, non-invasive strain, probiotic, colonizing microorganism, element-modifying microorganism, photosynthetic microorganism.

21. The composition of claim 20, wherein the at least one element-modifying microorganism includes at least one of a nitrogen-fixing microorganism, nitrifying microorganism, denitrifying microorganism, hydrocarbon-utilizing microorganism, dechlorinating microorganism, or a sulfate-reducing microorganism.

22. The composition of claim 1, wherein the at least one environmental medium treatment agent is pH dependent.

23. The composition of claim 1, wherein the composition includes at least one time-release formulation.

24. The composition of claim 23, wherein the time-release formulation includes at least one of a suspension, mixture, solution, sol, clathrate, colloid, emulsion, microemulsion, aerosol, ointment, capsule, micro-encapsule, cream, paste, resin, liniment, lotion, foam, polymer, buffer, lubricant, suspending agent, solvent, stabilizer, or gel.

25. The composition of claim 1, wherein the at least one environmental medium treatment agent is encoded by at least one vector.

26. The composition of claim 1, further including at least one detection material associated with each of the at least two modified microorganisms.

27. The composition of claim 26, wherein the at least one detection material includes at least one, sensor, contrast agent, or electronic identification device.

28. The composition of claim 27, wherein the at least one sensor includes at least one biosensor.

29. The composition of claim 27, wherein the at least one electronic identification device includes at least one radio frequency identification device.

30. The composition of claim 26, wherein the at least one detection material includes at least one of a radioactive, luminescent, colorimetric or odorous substance.

31. The composition of claim 26, wherein the detection material includes at least one of a diamagnetic particle, ferromagnetic particle, paramagnetic particle, super paramagnetic particle, particle with altered isotope, or other magnetic particle.

32. The composition of claim 26, wherein the detection material includes at least one of a DNA or RNA device.

33. The composition of claim 26, wherein the detection material or a precursor thereof is encoded by the at least one heterologous genetic element encoding at least one environmental medium treatment agent.

34. The composition of claim 26, wherein the detection material includes the at least one environmental medium treatment agent or a metabolite thereof.

* * * * *

UNITED STATES PATENT AND TRADEMARK OFFICE
CERTIFICATE OF CORRECTION

Page 1 of 1

PATENT NO.        : 8,852,916 B2
APPLICATION NO.   : 12/657607
DATED             : October 7, 2014
INVENTOR(S)       : Roderick A. Hyde et al.

It is certified that error appears in the above-identified patent and that said Letters Patent is hereby corrected as shown below:

In the Claims

Column 85, Lines 35-36, Claim 13:

"... wherein the at least metabolite is temperature dependent" should read

-- wherein the at least one metabolite is temperature dependent --

Column 86, Line 31, Claim 27:

". . . includes at least one, sensor, contrast agent, . . ." should read

-- includes at least one sensor, contrast agent, --

Signed and Sealed this
Twenty-seventh Day of January, 2015

Michelle K. Lee
*Deputy Director of the United States Patent and Trademark Office*